(12) United States Patent
Mitchell et al.

(10) Patent No.: US 9,844,410 B2
(45) Date of Patent: Dec. 19, 2017

(54) FLASH VAPORIZATION SURGICAL SYSTEMS

(71) Applicant: PRECISE LIGHT SURGICAL, INC., Sunnyvale, CA (US)

(72) Inventors: Gerald Mitchell, Los Altos, CA (US); Kenneth Arnold, Corralitos, CA (US)

(73) Assignee: PRECISE LIGHT SURGICAL, INC., Sunnyvale, CA (US)

( * ) Notice: Subject to any disclaimer, the term of this patent is extended or adjusted under 35 U.S.C. 154(b) by 41 days.

(21) Appl. No.: 14/537,413

(22) Filed: Nov. 10, 2014

(65) Prior Publication Data
US 2015/0057647 A1    Feb. 26, 2015

Related U.S. Application Data

(60) Division of application No. 13/092,847, filed on Apr. 22, 2011, now Pat. No. 8,881,735, which is a
(Continued)

(51) Int. Cl.
*A61B 18/20* (2006.01)
*A61B 18/22* (2006.01)
(Continued)

(52) U.S. Cl.
CPC ............ *A61B 18/22* (2013.01); *A61B 34/25* (2016.02); *A61B 2017/00199* (2013.01);
(Continued)

(58) Field of Classification Search
CPC .......... A61B 18/22; A61B 2018/00607; A61B 2018/00625; A61B 2018/00696;
(Continued)

(56) References Cited

U.S. PATENT DOCUMENTS

| 4,887,600 A | 12/1989 | Watson et al. |
| 4,965,803 A | 10/1990 | Esterowitz et al. |

(Continued)

FOREIGN PATENT DOCUMENTS

| EP | 0164751 A2 | 12/1985 |
| EP | 0214712 A1 | 3/1987 |

(Continued)

OTHER PUBLICATIONS

Japanese Office Action in related JP Application No. 2013-506350, dated Oct. 20, 2014, 10 pages (including unconfirmed English Translation).
(Continued)

*Primary Examiner* — Ahmed Farah
(74) *Attorney, Agent, or Firm* — Haynes Beffel & Wolfeld LLP

(57) ABSTRACT

A laser can produce pulses of light energy to eject a volume of the tissue, and the energy can be delivered to a treatment site through a waveguide, such as a fiber optic waveguide. The incident laser energy can be absorbed within a volume of the target tissue with a tissue penetration depth and pulse direction such that the propagation of the energy from the tissue volume is inhibited and such that the target tissue within the volume reaches the spinodal threshold of decomposition and ejects the volume, for example without substantial damage to tissue adjacent the ejected volume.

21 Claims, 41 Drawing Sheets

Related U.S. Application Data continuation-in-part of application No. PCT/US2009/065002, filed on Nov. 18, 2009.

(60) Provisional application No. 61/370,727, filed on Aug. 4, 2010, provisional application No. 61/327,060, filed on Apr. 22, 2010, provisional application No. 61/115,793, filed on Nov. 18, 2008.

(51) Int. Cl.
*A61B 34/00* (2016.01)
*A61B 18/00* (2006.01)
*A61B 17/00* (2006.01)

(52) U.S. Cl.
CPC .............. *A61B 2018/00607* (2013.01); *A61B 2018/00696* (2013.01); *A61B 2018/00714* (2013.01); *A61B 2018/2244* (2013.01)

(58) Field of Classification Search
CPC ........... A61B 2018/00702; A61F 9/008; A61F 9/00802; A61F 9/00821; A61F 9/00814; A61F 9/00823; A61F 9/00827
USPC .............. 606/3–18; 607/88–92; 128/898
See application file for complete search history.

(56) References Cited

U.S. PATENT DOCUMENTS

| | | | |
|---|---|---|---|
| 5,151,909 A * | 9/1992 | Davenport | B23K 26/06 359/326 |
| 5,390,204 A | 2/1995 | Yessik et al. | |
| 5,422,899 A | 6/1995 | Freiberg et al. | |
| 5,459,745 A | 10/1995 | Esterowtiz et al. | |
| 5,520,679 A | 5/1996 | Lin | |
| 5,591,161 A | 1/1997 | Negus et al. | |
| 5,621,745 A | 4/1997 | Yessik et al. | |
| 5,748,655 A | 5/1998 | Yessik et al. | |
| 5,782,822 A | 7/1998 | Telfair et al. | |
| 5,832,013 A | 11/1998 | Yessik et al. | |
| 5,984,916 A | 11/1999 | Lai | |
| 6,074,382 A | 6/2000 | Asah et al. | |
| 6,086,580 A | 7/2000 | Mordon et al. | |
| 6,090,102 A | 7/2000 | Telfair et al. | |
| 6,091,749 A | 7/2000 | Hoffmaster et al. | |
| 6,122,300 A | 9/2000 | Freiberg et al. | |
| 6,156,030 A | 12/2000 | Neev | |
| 6,159,204 A | 12/2000 | Hibst | |
| 6,258,082 B1 | 7/2001 | Lin | |
| 6,309,352 B1 | 10/2001 | Oraevsky et al. | |
| 6,325,792 B1 | 12/2001 | Swinger et al. | |
| RE37,504 E | 1/2002 | Lin | |
| 6,482,199 B1 | 11/2002 | Neev | |
| 6,484,052 B1 | 11/2002 | Visuri et al. | |
| 6,503,268 B1 | 1/2003 | Neuberger et al. | |
| 6,547,780 B1 | 4/2003 | Sinofsky | |
| 6,554,825 B1 | 4/2003 | Murray et al. | |
| 6,575,964 B1 | 6/2003 | Hobart et al. | |
| 6,592,611 B1 | 7/2003 | Zawada | |
| 6,618,620 B1 | 9/2003 | Freundlich et al. | |
| 6,743,221 B1 | 6/2004 | Hobart et al. | |
| 6,749,602 B2 | 6/2004 | Sierra et al. | |
| 6,751,490 B2 | 6/2004 | Esenaliev et al. | |
| 6,986,764 B2 | 1/2006 | Davenport et al. | |
| 6,998,567 B2 | 2/2006 | Yeik | |
| 8,029,501 B2 | 10/2011 | Miller | |
| 8,202,268 B1 | 6/2012 | Wells et al. | |
| 8,353,899 B1 | 1/2013 | Wells et al. | |
| 8,394,359 B1 | 3/2013 | O'Neil | |
| 8,636,726 B1 | 1/2014 | Wells et al. | |
| 8,881,735 B2 | 11/2014 | Mitchell et al. | |
| 2001/0001818 A1 | 5/2001 | Hibst | |
| 2001/0016732 A1 | 8/2001 | Hobart et al. | |
| 2003/0109860 A1 | 6/2003 | Black | |
| 2003/0216719 A1 | 11/2003 | Debenedictis et al. | |
| 2004/0082940 A1 | 4/2004 | Black et al. | |
| 2004/0151217 A1 | 8/2004 | Yeik | |
| 2004/0182416 A1 | 9/2004 | Allen et al. | |
| 2004/0195221 A1 | 10/2004 | Haglund, Jr. et al. | |
| 2005/0049582 A1 | 3/2005 | DeBenedictis et al. | |
| 2005/0224460 A1 | 10/2005 | Hutson et al. | |
| 2005/0288653 A1 | 12/2005 | Lai et al. | |
| 2006/0016790 A1 | 1/2006 | Yeik | |
| 2006/0153254 A1 | 7/2006 | Franjic et al. | |
| 2006/0153265 A1 | 7/2006 | Geiger et al. | |
| 2006/0195072 A1 | 8/2006 | Miller | |
| 2007/0265606 A1 | 11/2007 | DeBenedictis et al. | |
| 2007/0276359 A1 * | 11/2007 | Segal | A61N 5/06 606/11 |
| 2007/0299486 A1 | 12/2007 | Hoenig et al. | |
| 2008/0015556 A1 | 1/2008 | Chan et al. | |
| 2008/0086118 A1 | 4/2008 | Lai et al. | |
| 2009/0069871 A1 | 3/2009 | Mahadevan-Jansen et al. | |
| 2009/0118720 A1 | 5/2009 | Black et al. | |
| 2009/0227992 A1 | 9/2009 | Nir et al. | |
| 2010/0100084 A1 | 4/2010 | Girard et al. | |
| 2010/0305555 A1 | 12/2010 | Hutson et al. | |
| 2011/0196355 A1 | 8/2011 | Mitchell et al. | |
| 2011/0215076 A1 | 9/2011 | Littlewood et al. | |
| 2012/0232534 A1 * | 9/2012 | Rink | A61B 18/24 606/3 |
| 2014/0200511 A1 | 7/2014 | Boyden et al. | |
| 2015/0014891 A1 | 1/2015 | Amatucci et al. | |
| 2015/0238259 A1 | 8/2015 | Albeck et al. | |

FOREIGN PATENT DOCUMENTS

| | | |
|---|---|---|
| EP | 2119 408 A1 | 11/2009 |
| WO | 99/38572 A2 | 8/1999 |
| WO | 2008008499 A2 | 1/2008 |
| WO | 2010059734 A1 | 5/2010 |

OTHER PUBLICATIONS

Albagli D. et al., "Inertially Confined Ablation of Biological Tissue," Lasers in the Life Sciences 6(1), pp. 55-68, 1994.

Apitz I. et al., "Material ejection in nanosecond Er:YAG laser ablation of water, liver, and skin," Appl. Phys. A 81, 329-338, 2005.

Dingus R.S. et al., "Gruneisen-stress induced ablation of biological tissue," SPIE vol. 1427 Laser-Tissue Interaction II, pp. 45-54, 1991.

Esenaliev R.O. et al., "Studies of Acoustical and Shock Waves in the Pulsed Laser Ablation of Biotissue," Lasers in Surgery and Medicine 13:470-484, 1993.

European Search Report dated May 8, 2014 in Application No. 11772818.8, 6 pages.

Extended European Search Report dated Jun. 24, 2013 in EP09828174.4, 7 pages.

International Search Report dated Jan. 12, 2010 in PCT/US09/65002.

ISR dated Jan. 6, 2012 in PCT/US2011/033677.

Jacques S.L., "Role of tissue optics and pulse duration on tissue effects during high-power laser irradiation," Applied Optics 32:13, 2447-2454, 1993.

Kolev N.I., Chapter 13, "Bubble growth in superheated liquid," of vol. 2, Multiphase Flow Dynamics 2, Thermal and Mechanical Interactions, 2d ed., Springer, 2004.

Mikic B.B. et al., "On Bubble Growth Rates," Int. J. Heat Mass Transfer, vol. 13, Pergamon Press, UK, pp. 657-666, 1970.

Oraevsky A. A. et al., "Pulsed Laser Ablation of Soft Tissues, Gels, and Aqueous Solutions at Temperatures Below 100.degree. C.," Lasers in Surgery and Medicine 18:231-240, 1996.

Oraevsky A.A. et al., "Mechanism of laser ablation for aqueous media irradiated under confined-stress conditions," J. Appl. Phys. 78(2), 1281-1290, 1995.

Payne B., "The Role of Chromophore on Pulsed Laser Ablation of Biological Tissue," Jan. 17, 1997, M.S. thesis, MIT, 67 pp.

Plesset M.S. et al. "Bubble Dynamics and Cavitation," Ann. Rev. Fluid Mech. 9:145-85, 1977.

Plesset M.S. et al., "The Growth of Vapor Bubbles in Superheated Liquids", J. Appl. Phys. 25(4):493-500, 1954.

(56) References Cited

OTHER PUBLICATIONS

Robinson A.J. et al., "The dynamics of spherical bubble growth," Int. J. Heat Mass Transfer 47:5101-5113, 2004.
Venugopalan V. et al., "Thermodynamic Response of Soft Biological Tissues to Pulsed Infrared-Laser Irradiation," Biophysical Journal 70:2981-2993, 1996.
Venugopalan V. et al., Erratum Eq. 9 for Biophys. J. 70:2981-2993, 1996; at Biophys. J. 71:3530, 1996.
Vogel A. et al., "Mechanisms of Pulsed Laser Ablation of Biological Tissues," Chem. Rev. 103(2), 577-644, 2003.
Duan, et al., "Room temperature efficient actively Q-switched Ho:YAP laser," Mar. 16, 2009, vol. 17, No. 6, Optics Express.
El-Sherif et al., "Soft and hard tissue ablation with short-pulse high peak power and continuous thulium-silica fibre lasers," Lasers in Medical Science, vol. 18, No. Issue 3, Sep. 2003, pp. 139-147.
Fried et al. "High-Power Laser Vaporization of the Canine Prostate Using a 110 W Thulium Fiber Laser at 1.91 mm," Lasers in Surgery and Medicine 36:52-56 (Jan. 2005).
Jelinkova et al., "Diode-Pumped Tm:YAP Laser for Eye Microsurgery," Proc. of SPIE vol. 6871, 68721N, (Mar. 2008).
Li et al., High Efficiency 2.05-um CW and AO Q-Switched Operation of Diode End-Pumped Tm,Ho:GdV04 Laser, Laser Physics, Nov. 2008, vol. 18, No. 12, pp. 1512-1516.
Office Action dated Apr. 10, 2014 in related U.S. Appl. No. 13/092,847, 8 pages.
Office Action from 14/537,413 dated May 16, 2016, 24 pages.
Vogel et al., Minimization of thermomechanical side effects and increase of ablation efficiency in IR ablation by use of multiply Q-switched laser pulses, Proc. SPIE vol. 4617A, Laser Tissue Interaction XIII, 2002.

* cited by examiner

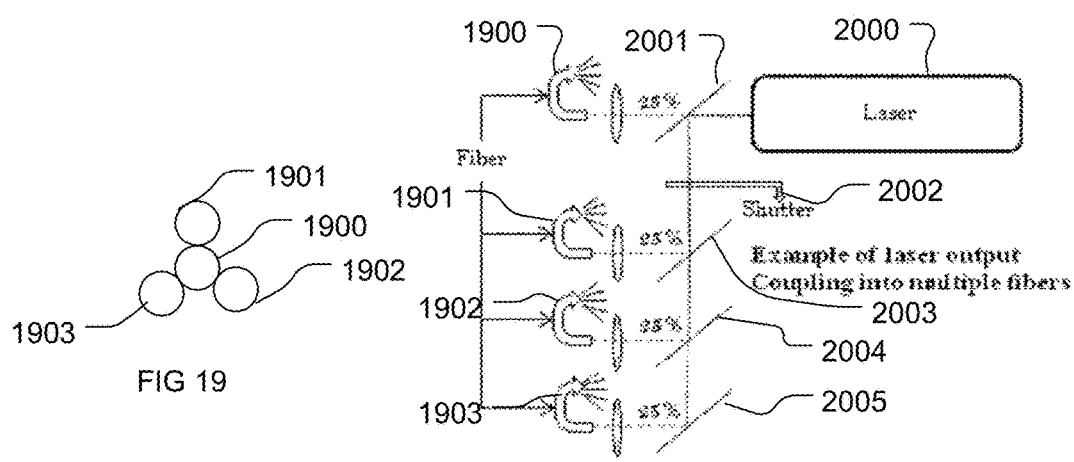
FIG 19
FIG 20
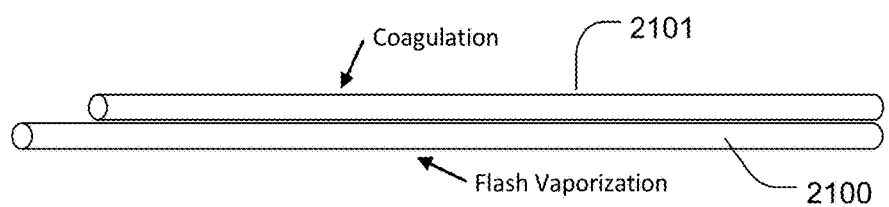
FIG 21

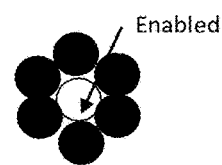
FIG 22
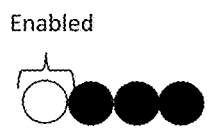  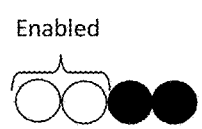  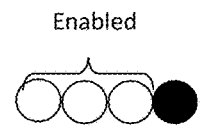  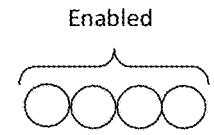
FIG 23a       FIG 23b       FIG 23c       FIG 23d

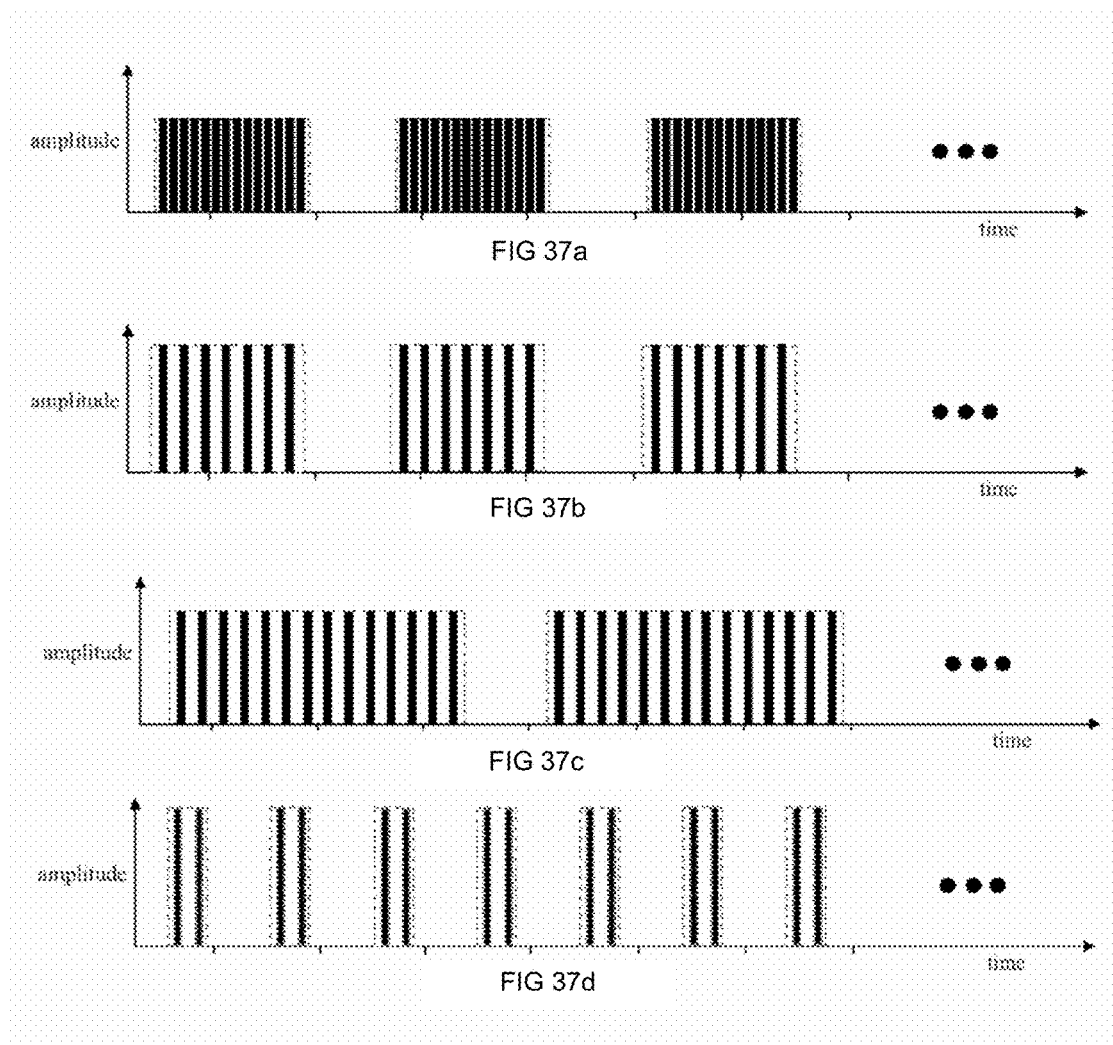

FLASH VAPORIZATION SURGICAL SYSTEMS

RELATED APPLICATIONS

This application is a divisional of U.S. patent application Ser. No. 13/092,847 filed on 22 Apr. 2011 (now U.S. Pat. No. 8,881,735), which application is a continuation-in-part of PCT/US2009/065002, filed on 18 Nov. 2009, designating the United States, which international application claims the benefit of U.S. Provisional Application No. 61/115,793 filed on 18 Nov. 2008, and which application claims the benefit of U.S. Provisional Application No. 61/327,060 filed on 22 Apr. 2010, and claims the benefit of U.S. Provisional Application No. 61/370,727 filed on 4 Aug. 2010.

BACKGROUND OF THE INVENTION

Well controlled tissue removal can be an important aspect of surgery. In at least some instances the ability of a surgeon to perform an incision without substantially affecting the surrounding tissue, for example the tissue adjacent to the resection site, can be clinically helpful. For many surgical procedures, it would be beneficial to avoid, or at least decrease, injury to the adjacent tissue. Furthermore, it can be beneficial for a surgeon to use a resection tool that is capable of reaching a remote surgical site, such as a treatment site accessed endoscopically.

A variety of tools have been developed to remove vascular soft tissue, cartilage and bone during surgical procedures, and many of these prior tools can be less than ideal for tissue cutting, for example of an internal surgical site. Mechanical instruments such as scalpels, biters and curettes along with powered mechanical instruments such as microdebriders and drills have been employed. Mechanical devices may cut tissue with varying degrees of localization and in at least some instances can induce mechanical trauma to the tissue. Although energy delivery based devices such as radio frequency, ultrasonic, and lasers have been used for tissue removal, these devices can have disadvantages in at least some instances. For example, when tissue is inadvertently removed or damaged by mechanical or thermal injury the clinical outcome and patient recovery can be adversely affected in at least some instances.

Radio frequency (RF) devices have been for tissue removal, and the prior RF devices can result in less than ideal tissue cutting. Although RF devices can be used to cut tissue by thermal and/or plasma mediated mechanisms, RF devices can cause at least some level of thermal injury in the adjacent tissue in at least some instances. In at least some instances, thermal injury may occur to the tissue adjacent to the cut. Also, RF devices can introduce accessibility and maneuverability challenges for surgeons, such as endoscopic surgeons in at least some instances.

Although prior laser based energy devices have been used for tissue removal, these laser systems can cut tissue more slowly than would be ideal and can injure the tissue adjacent to the cut. For example, thermal injury can occur in the tissue adjacent the cut with at least some commercially available medical laser systems. In at least some instances, the prior laser systems can be characterized by a Heat Affected Zone (HAZ) in front of an ablation zone. The laser energy can be introduced to the target tissue over time sufficient to raise the temperature and ablate tissue. In at least some instances the ablation process can be accompanied by charring of collateral tissue along with a significant HAZ which can be detrimental to the healing process.

Although some pulsed laser systems such as UV, photospallation, and ultrashort pulse laser systems may ablate tissue with somewhat decreased thermal damage as compared to continuous wave systems, in many instances pulsed laser systems may not cut tissue quickly and an ablation plume can interfere with a subsequent laser beam pulses such that increasing the rate of laser beam pulses may not adequately increase the rate of tissue removal in at least some instances.

Although UV based laser systems such as excimer laser systems have been used for tissue ablation, the UV based systems can have a shallow per pulse penetration depths and may result in tissue mutagenic effects in at least some instances. The pulse rate and shallow depth per pulse ablation depths can make UV based laser systems less than ideal for tissue removal in at least some instances. Also, the light from UV based laser systems can have less than ideal delivery through optical fibers, such that access to internal surgical sites can be limited in at least some instances. The generally slow overall depth penetration ablation rates, limited fiber delivery, and complexity can make UV laser systems less than ideally suited for tissue resection requiring larger cuts, in at least some instances. For example, with endoscopic surgical procedures light energy is delivered through an optical fiber and tissue is cut to a substantial depth along a substantial length, such that UV excimer laser systems are not well suited for endoscopic tissue cutting in at least some instances.

Although prior pulsed infrared lasers have been used to ablate tissue with photospallation, photospallation can be less than ideal for cutting tissue in at least some instances, such as endoscopically. Photospallation can have shallow per pulse ablation depths, such as a few microns, and photospallation based systems can have pulse rate limitations, such that the overall tissue cutting rate may be too slow for practical use. Also, photospallation systems can use optical wavelengths that are strongly absorbed by optical fibers, such that delivery to internal surgical sites on a patient may not be possible. Photospallation systems can be less than ideal for tissue resection due to very slow cutting rates and no practical means to deliver the laser energy for most endoscopic procedures.

Although prior ultrashort pulse laser technology such as femtosecond and picosecond laser systems can ablate tissue with an ionization process, the total energy per individual pulse can be very small and result in small amounts of tissue ablated. Also, the high peak powers can be unsuitable for fiber optic waveguides in at least some instances. Therefore, ultrashort pulse lasers can be less than ideal for tissue resection with larger cuts, such as in endoscopic surgical procedures.

Therefore, it would be helpful to provide improved methods and apparatus for cutting tissue that overcome at least some of the above limitation of the prior systems. Ideally, such methods and apparatus would provide surgeons a fast and effective cutting tool with flexibility to perform many sizes of tissue resections with precise localization, including cutting tissue without substantial thermal or mechanical damage on the tissue adjacent to the cut, for example. It would also be helpful if such methods and apparatus could accurately cut tissue without substantial tissue damage at an internal patient location with a flexible waveguide, for example with a flexible silica fiber for endoscopic procedures. Additionally methods and apparatus for tissue cutting that are applicable to a broad variety of tissue types may be important to surgeons and/or necessary to effectively perform certain procedures.

BRIEF SUMMARY

Methods and apparatuses are described to quickly and efficiently remove and resect tissue without substantial thermal or mechanical damage to the adjacent tissue. Delivery tools and control technologies are described that enable surgical techniques utilizing the tissue removal technologies. These technologies address the problems discussed above, and enable new classes of laser surgery.

BRIEF DESCRIPTION OF THE DRAWINGS

FIG. 19 shows an exemplary multi-fiber device tip configuration for using a painting motion to rapidly ablate tissue.

FIG. 20 shows an exemplary means to couple laser energy into multiple delivery fibers.

FIG. 21 shows a simple multi-fiber device tip with the coagulation fiber offset further from the treatment site than the Flash Vaporization fiber.

FIG. 22 shows an exemplary multi-fiber device tip configuration with only the center fiber enabled.

FIGS. 23a-23d shows an exemplary multi-fiber device tip configuration where the number of enabled fibers varies to suite the clinical need.

FIG. 37A shows an exemplary output waveform of the laser as in FIG. 28B when the system is operated in a combined q-switched and pump pulse mode with fixed pump pulse parameters and a shorter q-switch period.

FIG. 37B shows an exemplary output waveform of the laser as in FIG. 28B when the system is operated in a combined q-switched and pump pulse mode with fixed pump pulse parameters and a longer q-switch period.

FIG. 37C shows an exemplary output waveform of the laser as in FIG. 28B when the system is operated in a combined q-switched and pump pulse mode with fixed q-switch pulse parameters and a longer pump pulse duration.

FIG. 37D shows an exemplary output waveform of the laser as in FIG. 28B when the system is operated in a combined q-switched and pump pulse mode with fixed q-switch pulse parameters and a shorter pump pulse duration.

DETAILED DESCRIPTION

Figure 1A:
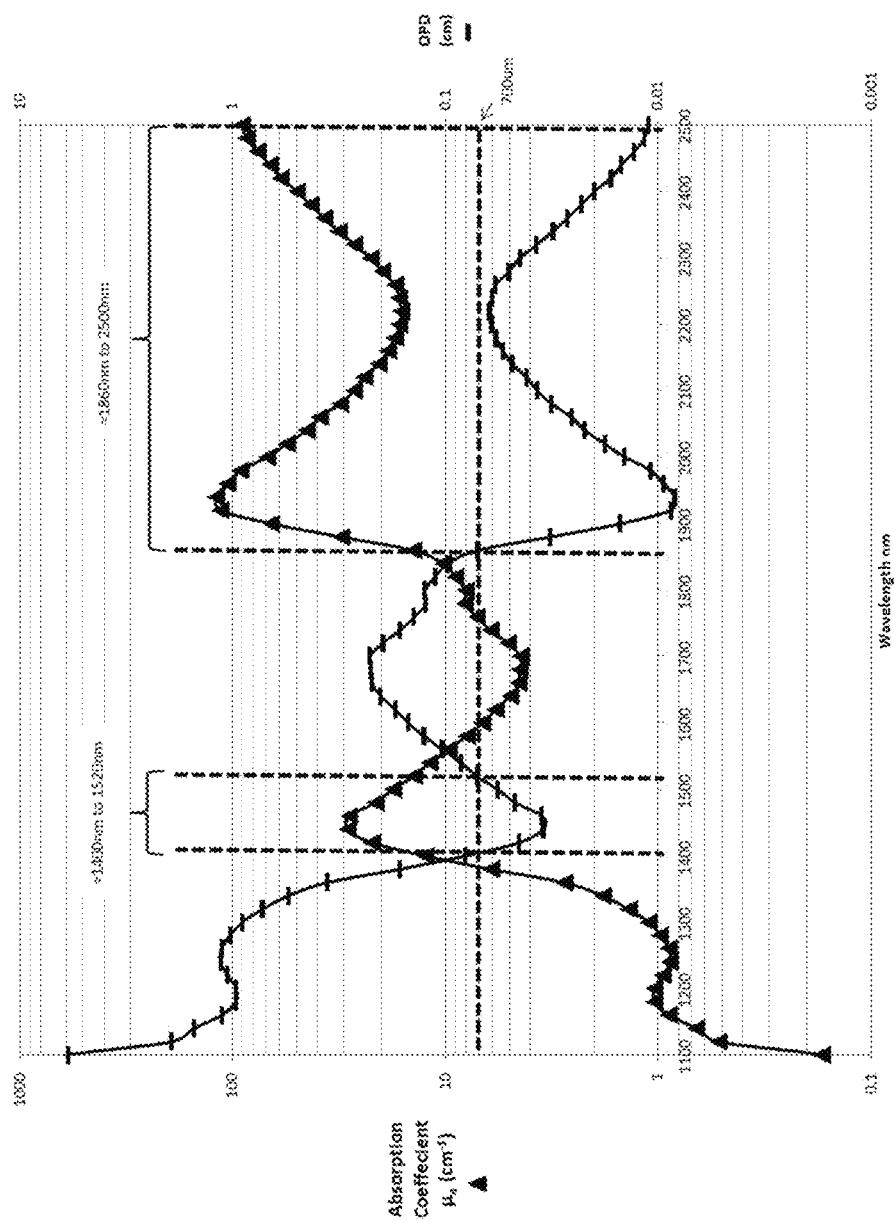
FIG. 1a-1b show the absorption coefficient and optical penetration depth (hereinafter "OPD") in water as a function of wavelength.

Embodiments of the present invention as described herein provide fast and efficient laser based cutting. The laser based cutting modality as described herein is applicable to a variety of tissue types and surgeries, such that there is no substantial thermal or mechanical damage or effect on the tissue adjacent to the cut.

One species of a more generic class of methods for removing tissue includes producing laser pulses having a wavelength between 1880 and 2080 nm or between 2340 and 2500 nm, having between 1 and 10 milliJoules per pulse, and having a pulse length less than 100 nsec; and delivering the pulses to a spot on the tissue; whereby an interaction volume defined by the area of the spot and the penetration depth (1/e) for the pulse in water has a ratio of depth to width from 2:1 to 1:6. The method can include delivering the laser pulses to the target tissue using a fiber optic having a core diameter in the range of 10 to 300, preferably 50 to 200 um. The waveguide used to deliver the pulses can comprise a silica optical fiber. The method can include utilizing pulse repetition rates from single shot to 2000 Hz. Utilizing this method, the applied energy heats the interaction volume of the tissue above a spinodal decomposition threshold for water within the pulse duration, translating laser energy into kinetic energy, via spinodal decomposition, leading to highly efficient ejection of tissue within the interaction volume. Furthermore, the laser pulses have a pulse duration sufficiently short to prevent stress waves and heat from propagating beyond the interaction volume relative to a shortest dimension of the interaction volume. The volumetric power density delivered to each spot can be greater than $10^{10}$ W/cm$^3$ for each pulse. As a result, most, if not essentially all, of the energy of the laser pulse is dissipated in the tissue that is removed by the pulse. It is found that using this method as applied to tissue including a sufficient water to produce pressure for ejection of the tissue infrastructure, and unlike any known prior art, significant volumes tissue can be removed with no apparent thermal injury to the tissue adjacent the cavity left by the ablation.

Another more general method includes producing laser pulses having a wavelength between 1400 and 1520 nm or between 1860 and 2500 nm, having between 0.5 and 40 milliJoules per pulse, and having a pulse length less than 200 nsec, preferably less than 100 ns; and delivering the pulses to a spot on the tissue using a waveguide such as a silica optical fiber having a core diameter in a range of 50 um to 200 um. Using this technology, an interaction volume defined by the area of the spot and the penetration depth (1/e) for the pulse in water has a ratio of depth to width from 2:1 to 1:6. The energy per pulse and wavelengths can be adjusted for interaction with other chromophores, and to produce pressures needed for various tissue types within this range.

According to a more general embodiment, a method for tissue removal, comprises producing laser pulses having a wavelength between 1400 and 1520 nm or between 1860 and 2500 nm, and having a pulse duration; and delivering the laser pulses to a spot on the tissue, the laser pulses having an energy per pulse ($E_p$) to heat an interaction volume of the tissue above a spinodal decomposition threshold for water within the pulse duration, and cause sufficient pressure for ejection of the target tissue, and having a pulse duration sufficiently short to prevent stress waves or heat from propagating beyond the interaction volume relative to a shortest dimension of the interaction volume. The method can be characterized more generally by the steps of producing laser pulses having a wavelength ($\lambda$) and pulse duration ($t_p$); and delivering a sequence of the laser pulses to respective spots having impact areas (A, e.g. $\pi r^2$) on the tissue and having a penetration depth in the tissue, the pulses having a nominal interaction volume in the tissue that is a function of the impact areas and the penetration depth; whereby an interaction volume defined by the area of the spot and the penetration depth (1/e) for the pulse in water, the interaction volume having a ratio of depth to width from 2:1 to 1:6.

The pulse duration in a more general genus of the method is less than 200 nsec and the pulse has a peak power density $E/(t_p A)$ below the threshold for inducing significant plasma formation. This method can comprise of delivering the sequence laser pulse using a silica optical fiber, with energy and pulse duration combinations that are below the damage threshold for the silica optical fiber. The method can be further characterized by an impact area having a dimension equal to a smallest distance across the impact area, and the pulse duration is within 3 times of a stress confinement duration of the time for propagation of an acoustic wave a lesser of one-half said dimension (e.g. r) and the penetration depth. The method can include laser pulses interacting with the interaction volume with a volumetric power density greater than $10^{10}$ W/cm$^3$.

According to a species of the more general method described herein, a laser including a Tm:YAP gain medium is arranged to produce an output wavelength near 1940 nm. The laser is used to deliver a sequence of pulses a tissue site, with an energy per pulse in the range of 1 to 10 mJ per pulse in pulse widths less than 100 nsec, with a beam delivery tool, such as a fiber optic or other waveguide. The method includes delivering the pulses to the treatment site with a spot size of 50 to 200 microns. A wavelength near 1940 nm has an optical penetration depth in water of about 80 microns. Because water is a primary component of most tissues, the penetration depth in tissue can be approximately the same. Using a spot size and an 80 micron penetration depth, one can determine the dimensions of an interaction volume within the tissue at the treatment site for a laser pulse. Using a pulse width less than 100 nsec, such as between 10 nsec and 50 nsec for a representative procedure, results in a condition of thermal and mechanical confinement of the energy dissipation from the laser pulse, within that interaction volume. Using an energy per pulse on the order of 0.5 to 40 mJ is sufficient in this example to generate greater than $5 \times 10^{10}$ W/cm$^3$ within the interaction volume and raise the temperature of the water in the interaction volume above the spinodal limit, can cause confined spinodal decomposition of the water. The spinodal decomposition results in an instantaneous phase change that creates substantial pressure in a range of about 200 bars to 10 kBars within the interaction volume at the treatment site. Energy in a pulse sufficient to induce the spinodal decomposition, is translated via this confined pressure into kinetic energy that can eject the tissue without visible thermal damage to tissue adjacent to the ejected volume, such as would otherwise be caused by thermal or acoustic waves induced by the ejection or the laser pulse. This effect is termed herein Flash Vaporization. The laser system according to this species can be operated with repetition rates from single shot to 2000 Hz, and because of the substantial volume of tissue ejected with each pulse, cutting rates can be achieved using Flash Vaporization that have not been possible using known prior art techniques.

Other species of the method within this more generic class can utilize lasers operating in wavelengths that have similar optical penetration depths in tissue having water as a primary component, including wavelengths between 1400 and 1520 nm or between 1860 and 2500 nm. Wavelengths in this range are also characterized by the fact that they are readily deliverable using silica waveguides on the order of 10 to 300 microns, preferably 50 to 200 microns in core diameter within the energy per pulse in the range of 0.5 to 40 mJ per pulse and pulse widths between about 10 nsec and 200 nsec. In some embodiments, the energy per pulse can range from about 100 uJ to about 100 mJ. Furthermore many embodiments embodiment for flash tissue vaporization using water as the chromophore utilizes pulse energies from 500 uJ to 30 mJ. Specific embodiments for Flash Vaporization can use water as the chromophore and a wavelength near 1.94 μm, pulse widths between 10 ns and 100 ns and pulse energies from 1 mJ to 10 mJ. Because of the availability and biocompatibility of silica waveguides, these species of laser systems can be readily utilized in a wide variety of endoscopic laser surgeries.

As spot size increases, the energy per pulse needed to achieve ejection by spinodal decomposition increases significantly. This limits the size of a laser spot that can be practically used in laser surgery applications. Other species described herein are configured to remove larger volumes of tissue per unit time. Such species utilize lasers capable of producing outputs that are a multiple of the energy per pulse to be applied by each pulse. In such species, a delivery tool including multiple waveguides can be coupled to the laser system for delivery of multiple spots, preferably adjacent, of laser energy to the treatment site in parallel or in rapid sequence. As there is essentially no residual energy in the tissue after ejection, the multiple spots are treated essentially independently. Multiple spots can be used to achieve very high tissue removal rates with no apparent residual injury to the tissue adjacent the cavity left by the ejected tissue.

It is recognized that different tissue types may require different parameters to achieve flash vaporization and eject substantially all of the material within the interaction volume. Thus a more generic class of laser systems as described herein can be characterized by including a laser to generate a pulsed beam of light energy, each pulse of the beam to irradiate a volume of tissue and having a duration and an amount of energy to inhibit mechanical energy, or stress, and thermal energy propagation from the volume such that the volume of the tissue is ejected with spinodal decomposition; and a controller coupled to the laser to generate the pulsed light beam in response to commands from the controller. The system can be combined with an endoscopic delivery tool, including one or more optical fibers. Laser surgery based on flash vaporization can be performed within a complex parameter space described in more detail below. The discovery of commercially feasible operating conditions for lasers and delivery tools as described herein enables for the first time, a new variety of "cold ablation" surgical techniques.

Flash Vaporization as described herein can use pulsed laser energy to efficiently ablate tissue such that the incident laser energy absorbed by tissue is substantially converted from thermal to kinetic energy that is ejected from the treatment site to remove tissue. As a majority of the energy deposited with each pulse can be translated into kinetic energy confined within the tissue volume, any thermal or mechanical energy imparted into the adjacent tissue is substantially decreased, and in some instances essentially eliminated.

The lower overall power requirements provide an advantage in the size and power consumption of the laser itself. A non limiting example of laser energy characteristics as delivered to tissue to achieve Flash Vaporization, ablation with negligible thermal or mechanical injury to the adjacent tissue, include energy per pulse, pulse width, target volume, target shape, wavelength and repetition rate.

A means to deliver the laser energy to the treatment site can include silica waveguides, doped silica waveguides, non silica based solid core waveguides, hollow core waveguides and free space beam delivery, including articulating arms. Laser based cutting tools can be used with many surgical approaches, including endoscopic surgery. For many surgical procedures, including endoscopic surgery, it is desirable to deliver the laser energy through a low cost, biocompatible, small and flexible waveguide, such as a silica optical fiber waveguide, having an energy transmission efficiency of at least about 80%.

Flash Vaporization can be used for surgical applications. Flash Vaporization provides surgeon the ability to cut tissue, even in endoscopic applications, for example without substantial thermal or mechanical residual effects to the adjacent tissue. The cutting tip can be very small, sub-millimeter, and flexible. The laser based flash vaporization cutting tool can be easily positioned and maneuvered at a surgical treatment site. Additionally flash vaporization may not apply mechanical pressure, such as a scalpel would, on the tissue to create a cut. Flash vaporization is well suited for surgical applications where thermal or mechanical injury to the adjacent tissue is undesirable. For example removal of diseased tissue that has grown around a nerve bundle is an advantageous application of flash vaporization. Precisely controlling the location of the cut along with negligible thermal or mechanical injury to the nerve bundle itself is useful in this application. Pulse by pulse operation with microscopic imaging allow for very precise cutting. Flash vaporization can provide surgeons with capability to safely remove tissue with high precision and without impacting the surround tissue. Surgeons can achieve better outcomes, efficiently with less risk to the patient.

Flash vaporization may be combined simultaneously or serially with other thermal based treatment modalities so as to provide heat induced hemostatic capability surrounding the cut, for certain surgical applications when hemostasis is desirable.

The flash vaporization ablation mechanism can ablate tissue with negligible thermal affects adjacent to the ejected tissue. Flash vaporization can achieve cutting rates with negligible residual damage to the adjacent tissue. Flash vaporization can cut tissue with fast cutting rates. Flash vaporization can be achieved with wavelengths of light energy delivered through standard silica fibers, for example. Clinically a flash vaporization based laser system offers very fast cutting rates when delivered through a commercially available optical fiber waveguide. Flash vaporization may comprise a high efficiency rate so as to cut tissue with a low average power laser generator which allows the system to be sized to fit in a physician's office with portability and reliability. Utilizing a flash vaporization based resection system allows the surgeons to readily access many surgical sites of the patient, for example endoscopically, and can cut many types of tissue while preserving adjacent tissue to produce better surgical outcomes with less risk and a faster recovery period for their patients.

Flash vaporization can include the incident laser energy being absorbed by a chromophore in the target tissue. Non limiting examples of typical chromophores for laser energy interaction with tissue may include water, blood, collagen and melanin. It can be desirable to select a chromophore that is present in a wide range of tissue types with sufficient quantity to be effectively targeted. Water is the target chromophore for many embodiments.

The rapid cutting rates achieved with flash tissue vaporization are can be achieved with a deep optical penetration depth OPD. Many embodiments use OPDs of at least 70 um to achieve significantly faster cutting rates.

Spinodal decomposition may comprise a phase change of water from liquid to gas that may occur substantially uniformly within a target volume. By elevating the water temperature within the volume to approximately 300° C. or greater, for example, within a time frame sufficient to initiate spinodal decomposition. The water in the volume can undergo a spatially and temporally uniform phase change, resulting in pressure induced kinetic energy such that the tissue can be ejected with inhibited damage to tissue adjacent to the target volume after each pulse. The energy released as a result of the uniform phase change can create stresses that are used to eject the volume.

Flash vaporization can occur with a laser beam pulse by elevating a target volume to a temperature at or in excess of the spinodal threshold for water, in which the target volume can be determined by the incident energy laser beam spot size and the OPD. Also, the spinodal decomposition temperature threshold can be met or exceeded within a time frame that substantially inhibits stress waves from propagating beyond the target volume, such that the ablation is substantially stress confined to the target volume. The stress confinement conditions can be determined by the propagation speed of the stress waves and the geometry of the target volume. The resulting temporally and spatially uniform phase transition that occurs via spinodal decomposition within a substantial majority of the target volume that creates a substantially confined recoil stress so as to efficiently eject the volume, for example without depositing substantial energy into the tissue adjacent to the target volume after the pulse.

Additional conditions that can be related to weakening the structural integrity of the target volume by liquefaction, for example liquefaction of collagen, optimized volume geometries and incident energy parameters ensure a highly efficient removal process with substantially no affect to the surrounding region.

Silica based fiber optic waveguides are suitable for transmitting wavelengths with strong water absorption characteristics for flash tissue vaporization as described herein. Wavelengths greater than about 2.3 um can exhibit strong bulk absorption in silica based fibers and wavelengths greater than 2.5 um can be impractical to use with silica based fiber for ablation processes as described herein.

Many embodiments use light energy having wavelengths within a range from about 1.4 um to about 1.52 um and from about 1.86 um to about 2.5 um, and 2.5 microns may comprise a silica fiber limit. The wavelengths of these embodiments are strongly absorbed by water, are transmissible for use through a silica based optical fiber waveguide and provide an interaction depth of between approximately 70 um and approximately 700 um, for example.

FIG. 1A shows the absorption characteristics of water and corresponding OPD across a broad range of wavelengths. The preferred wavelength ranges of 1.4 um to 1.52 um and 1.86 um to 2.5 um correspond to an OPD≤700 um. Additional embodiments include interaction depths between 70 um and 300 um. Preferred systems have a penetration depth greater than about 50 um, to support interaction volumes and geometries sufficient for flash vaporization at reasonable rates.

Figure 1B:
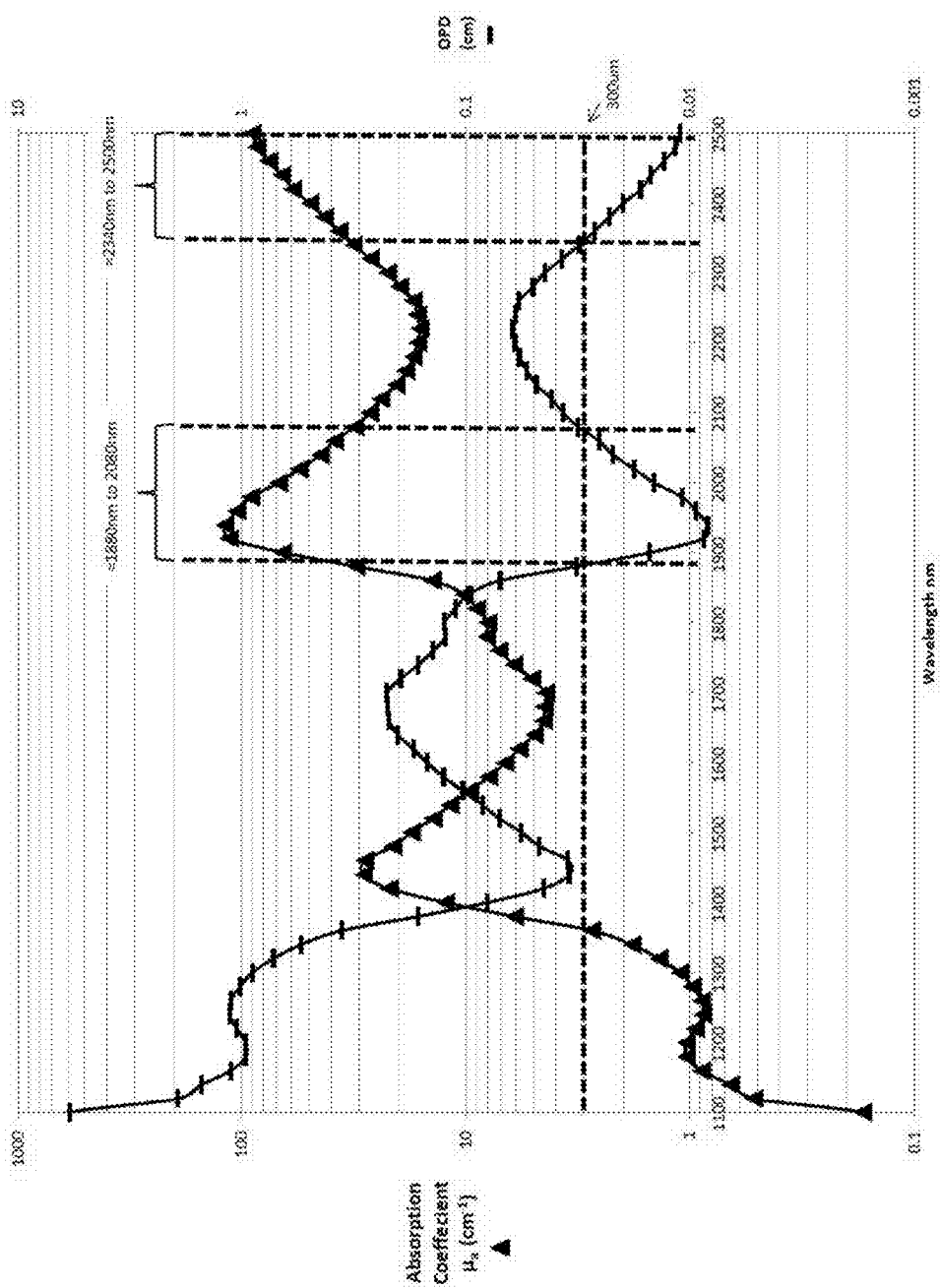

FIG. 1B shows the absorption characteristics of water and corresponding OPD across a broad range of wavelengths. Wavelength ranges with OPD between 70 um and 300 um are from about 1.88 um to about 2.08 um and from about 2.34 um to about 2.5 um. As tissue may comprise substantial amounts of water, the water penetration depth can be used to determine tissue penetration and corresponding tissue ejection volume. A person of ordinary skill in the art can conduct experiments to determine tissue penetration depths based on the teachings described herein. Non limiting exemplary wavelengths are 1.92 um, 1.94 um, 1.99 um and 2.01 um. Additional embodiments utilize a wavelength of approximately 1.94 um. The laser beams of embodiments with a wavelength of approximately 1.94 um are strongly absorbed in water, are transmissible through a silica based fiber and provide an interaction depth in the range of 80 um.

Flash vaporization can include delivering laser energy to tissue such that a substantial majority of the target volume of tissue reaches a temperature of approximately 300° C. or higher. By elevating the target tissue volume to at least 300° C., for example, the liquefaction threshold of collagen can be reached as well as the threshold for spinodal decomposition of the target water chromophore. Various forms of collagen are present is many target tissues. By elevating the temperature to the liquefaction threshold the structural integrity of the collagen can be at least significantly weakened. The weakened collagen structure reduces the energy used to eject the material, thereby significantly enhancing the efficiency of tissue removal. By raising the preferred target chromophore, for example water ($H_2O$), within the tissue volume at least to its spinodal limit about 300° C. a relatively uniform phase change can occur within a substantial majority of the target volume. The spinodal phase change is distinctly different from nucleation and bubble growth mechanisms. At the spinodal threshold limit water becomes mechanically unstable and an ensuing rapid phase change to vapor occurs with relative uniformity in the tissue volume creating significant kinetic energy within the target volume.

A further aspect of flash tissue vaporization can include, for example, achieving at least an approximate temperature within the target volume of 300° C. in a time sufficiently short such that the tissue adjacent to the target volume has insufficient time to react substantially. Thus a substantial majority of the energy is deposited in the target tissue volume before any substantial absorption induced stress propagates from and before substantial heat diffuses away from the target volume such that the stress propagation and heat diffusion are inhibited substantially. This inhibition of the dissipation of stress propagation energy and the inhibition of diffusion of heat energy can inhibit damage to tissue adjacent to the target volume after the target volume is ejected.

The parametric constraints that can be used to describe laser beam parameters for the flash tissue vaporization are described by the following equations, which establish a very complex parameter space.

$$\tau_p \leq \frac{1}{\mu_a v_s} \qquad \text{Equation 1}$$

where $\tau_p$ is the pulse width (sec),
$\mu_a$=absorption coefficient (cm$^{-1}$) or 1/fiber radius (cm) whichever is shortest,
$v_s$=velocity of sound (cm/sec)

Equation 1 corresponds to a condition where the pulse duration is sufficiently short to prevent stress waves from propagating beyond the target volume relative to the shortest dimension of the target volume. For the purposes of flash vaporization substantial stress confinement, enabling tissue ablation via spinodal decomposition with negligible adjacent tissue damage may be achieved with pulse durations up to approximately 3 times the pulse duration indicated by equation 1.

$$\tau_p \leq \frac{1}{\mu_a^2 \kappa} \quad \text{Equation 2}$$

where $\tau_p$ is the pulse width (sec),
$\mu_a$=absorption coefficient (cm$^{-1}$),
$\kappa$ is thermal diffusivity (cm$^2$/sec)

Equation 2 corresponds to a condition where the pulse duration is sufficiently short to prevent heat from propagating beyond the target volume.

$$1 \geq \frac{\kappa \tau_p}{\delta^2} \quad \text{Equation 3}$$

where $\tau_p$ is the pulse width (sec),
$\kappa$ is thermal diffusivity (cm$^2$/sec),
$\delta$ is the chromophore size (cm$^2$). For pure H$_2$O, eq3 is equivalent to eq2 as $\delta = 1/\mu_a$ Equation 3 corresponds to a condition where the pulse duration is sufficiently short to prevent thermal propagation beyond the target chromophore, where for example, the target chromophore represents small volumes of interstitial water dispersed within the collagen mesh work of the target tissue.

Equations 1-3 identify the upper limit of pulse durations related to the tissue laser interaction, suitable for flash tissue vaporization.

The temperature attained as a result of a laser pulse in tissue can be calculated from the following equation for pulses shorter than 1 μsec.

$$T = \frac{\mu_a \phi}{C_v \rho} e^{-\mu_a z} \quad \text{Equation 4}$$

where T=temperature (° C.),
Φ=Energy (J/cm$^2$),
Cv=Where Cv is the isochoric specific heat (saturated liquid heat capacity at constant volume) of the chromophore (H$_2$O) (J/g° C.),
ρ=density (g/cm$^3$)
and z=depth (cm)

Equation 4 indicates the required fluence to achieve a desired temperature at a depth in the target volume.

$$\phi = \frac{C_v T \rho}{\mu_a} \quad \text{Equation 5}$$

where T=temperature (° C.),
Φ=Energy (J/cm$^2$),
C$_v$=specific heat (J/g° C.),
ρ=density (g/cm$^3$)

Equation 5 indicates the appropriate fluence to reach the threshold temperature for spinodal decomposition of the target chromophore (H$_2$O).

Equations 1-5 may be used to determine, for a given wavelength and target tissue, the fluence required to reach 300° C. with substantially the entire target volume and to determine the maximum pulse duration suitable for flash vaporization. For flash tissue vaporization the lower pulse duration limit can, in part, be determined to prevent substantial plasma generation and to prevent damage to a waveguide delivering the pulse, like a silica based optical fiber.

Volumetric power density (VPD) can be re-cast to Equation 6;

$$VPD = \frac{\mu_a E}{A_r t_p} = \frac{\mu_a E}{\pi \omega^2 t_p} \quad \text{Equation 6}$$

where:
E=energy (J),
$\mu_a$=absorption coefficient (cm$^{-1}$),
A$_r$=area (cm$^2$),
t$_p$=pulse width (sec) and
ω=radius of incident spot (mm) {{{cm??}}}

Spinodal decomposition has a minimum VPD to substantially eliminate energy loss due to bubble formation and/or cavitation. Experimentation suggests a VPD of roughly 10$^{10}$ W/cm$^3$ or higher is sufficient to induce spinodal decomposition, in some instances typically with pulse durations ≤200 ns. For stress confinement, shorter pulse lengths can be required.

Flash Vaporization may include a pulse width short enough for a given target tissue volume to inhibit substantial thermal or mechanical energy within the interaction volume from propagating into the adjacent volume during the deposition of the light energy into the target tissue. It may be advantageous for the pulse width to be long enough for a given peak irradiance and target tissue to substantially inhibit plasma formation. Propagation of thermal energy, mechanical energy and substantial plasma formation may each introduce tissue removal inefficiencies that can lead to damage of the adjacent tissue. Pulse widths in the range of about 100 ps to 1 us may be suitable for flash tissue vaporization. For example, pulse widths between 0.5 ns and 100 ns can be preferable for wavelengths targeting water as a chromophore.

The parameters of Flash vaporization are related to the size of the targeted tissue interaction volume. Larger interaction volumes may require more laser energy to reach the spinodal and liquefaction limits while satisfying the above conditions so as to substantially prevent thermal and/or kinetic energy from propagating into the tissue adjacent to the ablation site. As the above described pulse energy increases, the pulse duration may also increase in order to inhibit exceeding peak power damage thresholds of the laser generator and/or the delivery system. The interaction volume range can be determined based on the largest volume where flash vaporization can be achieved with a practical and commercially viable laser and delivery system. For example using a 1.94 um wavelength and targeting porcine kidney with approximately 70% water content with a 100 um core silica fiber in contact mode yields an interaction volume of approximately 9×10$^{-7}$ cm$^3$. An interaction volume size in the range of 10$^{-8}$ cm$^3$ to 10$^{-4}$ cm$^3$ can be used in many embodiments. Many embodiments can use an interaction volume of 10$^{-7}$ cm$^3$ to 10$^{-5}$ cm$^3$.

Flash vaporization can be related to the shape of the interaction volume. The ratio of the interaction volume depth to the interaction volume width may correspond to the efficiency in which the tissue is removed including the ability to extract a substantially majority of the absorbed laser energy with the ejected volume. The ejection of target tissue from the treatment site may comprise a mechanical process. Kinetic energy created by spinodal decomposition within the interaction volume can drive the tissue material removal process. Optimizing the shape of the interaction volume can improve the efficiency of tissue removal. Interaction volume shapes where the depth is substantially larger than the width may provide less efficient ejection of the target tissue, which can lead to residual mechanical or thermal effects on tissue adjacent to the target volume. Additionally, interaction volumes where the depth is substantially less than the width may lead to inefficient target tissue removal which may cause residual mechanical or thermal effects on the adjacent tissue. Depth and width ratios are related to the OPD of the wavelength used for a given target material and the incident spot size delivered to the tissue surface.

Figure 2A:
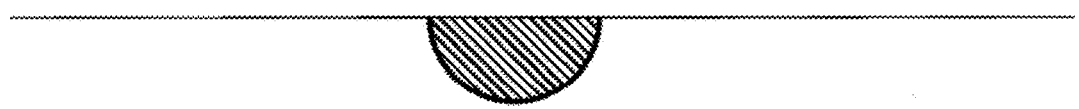
FIG. 2a-2c show a representative interaction volume depth to width ratio, in accordance with embodiments.
Figure 2B:
Figure 2C:

FIG. 2 shows a representative interaction volume depth to width ratio for several embodiments. One embodiment is a depth to width ratio of approximately 1:2, see FIG. 2a. This can be a preferred species because the efficiency of tissue ejection can be high, and the energy per pulse needed to achieve tissue removal can be well within operating conditions of a fiber optic delivery tool. Another embodiment is a depth to width ratio in a range between 1:4 to 2:1, see FIG. 2b. This range encompasses larger areas on the tissue surface, and requires larger energy per pulse for the larger areas. These larger energy per pulse requirements can be more difficult to achieve with a given laser system. Another embodiment is a depth to width ratio in a range between 1:6 to 2:1, see FIG. 2c. This more generic range of geometries includes even larger surface areas, requiring even larger energies per pulse.

The targeted tissue interaction volume size and/or shape can determine the pulse energy to achieve Flash Vaporization. Too little energy per pulse may not drive the target chromophore to the spinodal limit and/or may not provide sufficient kinetic energy to eject the material within the interaction volume. Too much energy per pulse may not be practical to generate or deliver and can introduce inefficiencies in the tissue removal process. In both cases, too little and too much per pulse energy, residual mechanical and/or thermal affects on the adjacent tissue may occur. The threshold energy to achieve spinodal decomposition can be calculated from equations 1-5.

The efficiency can be determined per equation 7.

$$\eta = \frac{A\rho}{\mu_a E_i} \ln\left(\frac{E_i}{E_{th}}\right) \quad \text{Equation 7}$$

where $\eta$=efficiency (gm/J),
$\mu_a$=absorption coefficient (cm$^{-1}$),
A=spot size (cm$^2$),
$\rho$=density (gm),
$E_i$=input energy (J) and
$E_{th}$=threshold energy for spinodal decomposition at the surface (J)
And for optimum efficiency $$E_i = E_{th} e \text{ yields } E_{opt}$$

e is Euler's number=2.71828 (to five significant figures).

The ideal energy is related to the energy required to achieve spinodal decomposition plus the additional energy to eject the target volume with optimal efficiency. Energy exceeding $E_{opt}$ is imparted to the ejected material, in this case water. Now as the target volume is not entirely water and can contain significant amounts of collagen in different organizational structures, the energy exceeding $E_{opt}$ may be used to overcome the tensile strength of the tissue within the volume.

Many embodiments for flash vaporization include pulse energies within the range from about 100 uJ to about 100 mJ. Furthermore many embodiments embodiment for flash tissue vaporization using water as the chromophore utilizes pulse energies from 500 uJ to 30 mJ. Specific embodiments for Flash Vaporization can use water as the chromophore and a wavelength near 1.94 µm and pulse energies from 1 mJ to 10 mJ.

The flash tissue vaporization process, in some instances, has threshold fluences in the range of joules per centimeter squared.

Figure 3:
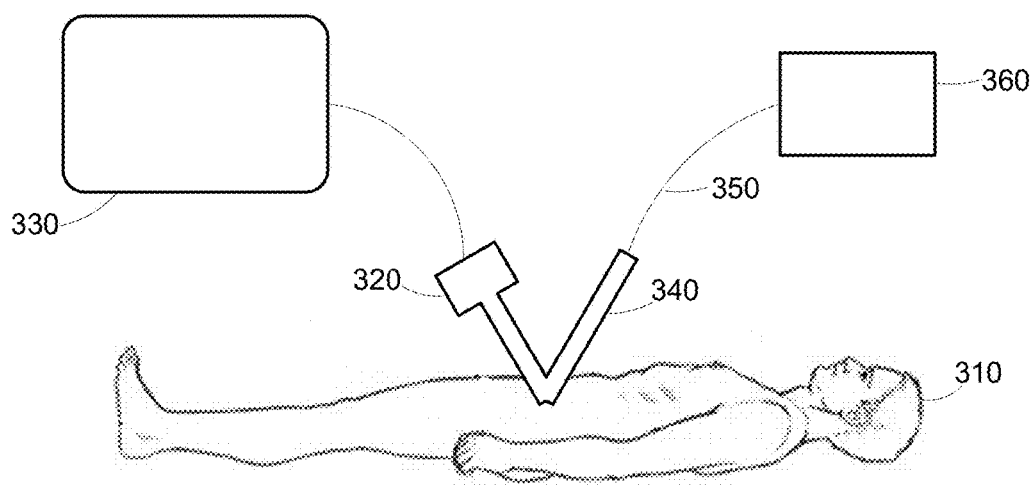
FIG. 3 shows a laser system utilizing Flash Vaporization for tissue removal during laparoscopic surgery, in accordance with embodiments.

FIG. 3 shows a laser system utilizing Flash Vaporization for tissue removal during laparoscopic surgery. The patient 310 has an imaging system 320 inserted in the thoracic cavity. The imaging system 320 may be a direct viewing type or it may have a camera with a video display 330 such that the surgeon can view the inside of the thoracic cavity. An insertion device 340, such as an endoscope, with and a delivery system 350 is also inserted into the thoracic cavity. The proximal end of the delivery system 350 is attached to a laser system 360.

Figure 4:
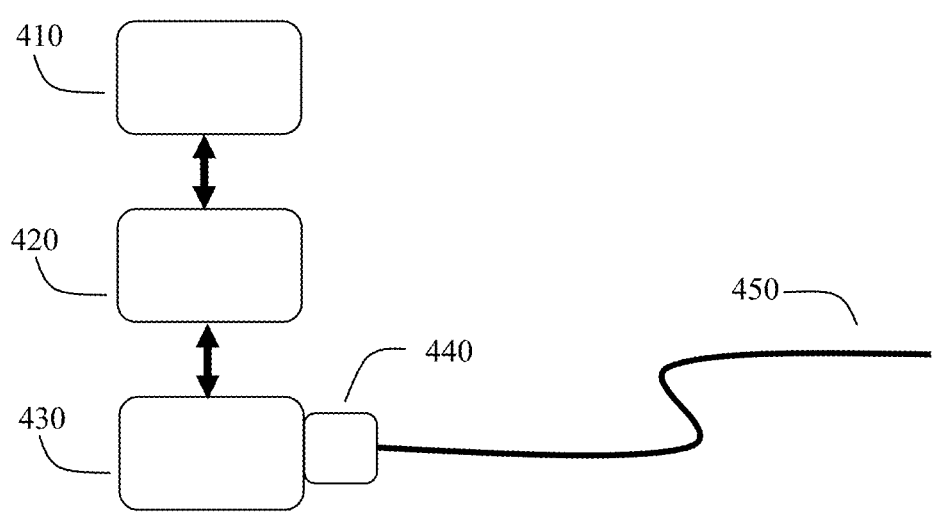
FIG. 4 shows a laser system for implementing a Flash Vaporization based surgical device, in accordance with embodiments.

FIG. 4 shows the laser system of FIG. 3 for implementing a Flash Vaporization based surgical device. The laser system has a user interface 410 to adjust system parameters and to control the laser energy emission. The user interface 410 is in communication with the controller 420. The controller operates the resonator 430 to provide the appropriate output selected via the user interface 410. The output of laser energy from the resonator 430 is directed to a device coupler 440. The device coupler 440 directs the laser energy into a delivery system 450. A representative delivery system 450 comprises a 100 um core silica fiber used in contact, or near contact, with the target tissue. A representative non-contact delivery system 450 comprises a silica core fiber with a focusing element to generate a 100 um treatment spot about 2 cm from the tip of the silica fiber. In other embodiments, fiber tip optical components can be utilized for spot shaping and beam pointing.

Figure 5:
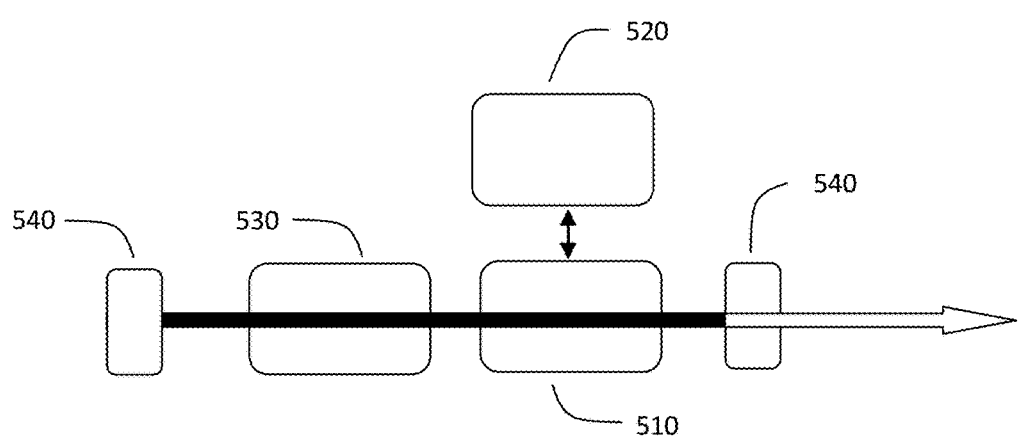
FIG. 5 shows a laser resonator for implementing Flash Vaporization, in accordance with embodiments.

FIG. 5 shows components of the resonator 430 for implementing flash tissue vaporization, having a gain medium 510, pump source 520, modulator 530 and at least two mirrors 540. Non limiting examples of the gain medium 510 include solid state, gas, liquid, semiconductor based or waveguide based gain mediums. The gain medium 510 may be selected to provide a specific wavelength or wavelength range that is desirable for interaction with the target tissue. Non limiting examples of solid state gain medium 510 for the preferred wavelength range of 1.8 um to 2.5 um are Ho:YAG, Tm:YAG, Tm:YAP, Tm:GaVO4 and Tm:YLF. A solid state gain medium is an embodiment due to the ability to generate laser energy with highly efficient pumping processes within wavelength ranges that may target chromophore present in a wide variety of tissue. Solid state gain mediums also enable small and low cost implementation. The lower cost and size of solid state lasers are appealing to the surgeons and facilities using the equipment. Non limiting examples of the pump source 520 include a laser diode, arc lamp, flash lamp or electrical stimulation. A laser diode is a preferred pump source 520 offering a low maintenance requirements and an efficient means to pump the gain medium 510. Furthermore an end pumping configuration may be employed to improve the efficiency of the pumping process. A modulator 530 may be used to provide pulsed laser energy and may be implemented intracavity or externally. Non limiting examples of modulators 530 include acousto-optic, electro optic, saturable absorbers or mechanical means. An embodiment may be an intracavity acousto-optic or electro optic modulator. The electro-optic modulator may have further advantages when the laser resonator 430 produces polarized energy. The laser resonator 430 preferably has two mirrors 540. One mirror reflected approximately all of the laser energy while the second mirror partially reflects the laser energy serving as an output coupler to extract laser energy from the laser resonator. A two mirror resonator often reduces the laser resonator complexity and reduces the overall cost of the laser system. Additional laser resonator configurations with more than two mirrors may also be used. Optimizing the efficiency and simplicity of the laser resonator 430 is a factor in the commercial viability of a laser based surgical tool. A representative laser resonator configured for flash vaporization includes a gain medium 510 comprising Tm:YAP configured to lase efficiently at 1.94 um with a pump source 520 comprising a fiber coupled laser diode configured for end pumping the gain medium 510. The representative laser resonator further includes a modulator 530 comprising an acousto-optic Q-switch and two mirrors 540, one substantially reflecting all the light at 1.94 um and the second partially reflecting light at 1.94 um to function as an output coupler.

Thus, one species of a more generic class of laser systems capable of use for flash vaporization as described herein includes a Tm:YAP gain medium 510 arranged to produce an output wavelength near 1940 nm, operating with an energy per pulse in the range of 1 to 10 mJ per pulse in pulse widths less than 100 nsec, with a beam delivery tool 350, 340, such as an endoscope with a fiber optic or other waveguide, arranged to deliver a spot size of 50 to 200 microns to a target tissue. A wavelength near 1940 nm has an optical penetration depth in water of about 80 microns. Because water is a primary component of most tissues, the penetration depth in tissue can be approximately the same. Using a spot size and a 80 micron penetration depth, one can determine the dimensions of an interaction volume within the tissue at the treatment site for a laser pulse. Using a pulse width less than 100 nsec, such as between 10 nsec and 50 nsec for a representative procedure, results in a condition of thermal and mechanical confinement of the energy dissipation from the laser pulse, within that interaction volume. Using an energy per pulse on the order of 0.5 to 40 mJ is sufficient in this example to generate greater than $10^{10}$ W/cm$^3$ within the interaction volume and raise the temperature of the water in the interaction volume above the spinodal limit, can cause confined spinodal decomposition of the water. The spinodal decomposition results in an instantaneous phase change that creates substantial pressure in a range of about 200 bars to 10 kBars within the interaction volume at the treatment site. Energy in the pulse is translated via spinodal decomposition into kinetic energy that can eject the tissue without visible thermal damage to tissue adjacent to the ejected volume caused by thermal or acoustic waves induced by the ejection or the laser pulse. This effect is termed herein Flash Vaporization. The laser system according to this species can be operated with repetition rates from single shot to 2000 Hz, and because of the substantial volume of tissue ejected with each pulse, cutting rates using Flash Vaporization that have not been possible using known prior art techniques can be achieved.

Other species of laser systems within this more generic class includes lasers 430 operating in wavelengths that have similar optical penetration depths in tissue having water as a primary component, including wavelengths between 1400 and 1520 nm or between 1860 and 2500 nm. Wavelengths in this range are also characterized by the fact that they are readily deliverable using silica waveguides on the order of 50 to 200 microns in core diameter within the energy per pulse in the range of 0.5 to 40 mJ per pulse and pulse widths between about 10 nsec and 200 nsec. A controller 420 and a visualization monitor 410 can be utilized for control of laser parameters and surgical procedures. In some embodiments, the controller 420 can be operated to control energy per pulse within a range from about 100 uJ to about 100 mJ. Furthermore many embodiments embodiment for flash tissue vaporization using water as the chromophore utilizes pulse energies from 500 uJ to 40 mJ. Specific embodiments for Flash Vaporization can use water as the chromophore and a wavelength near 1.94 µm and pulse energies from 1 mJ to 10 mJ. Because of the availability and biocompatibility of silica waveguides, these species of laser systems can be readily utilized in a wide variety of endoscopic laser surgeries.

It is recognized that different tissue types may require different parameters to achieve flash vaporization and eject substantially all of the material within the interaction volume. Thus a more generic class of laser systems as described herein can be characterized by including a laser to generate a pulsed beam of light energy, each pulse of the beam to irradiate a volume of tissue and having a duration and an amount of energy to inhibit mechanical energy, or stress, and thermal energy propagation from the volume such that the volume of the tissue is ejected with spinodal decomposition; and a controller coupled to the laser to generate the pulsed light beam in response to commands from the controller. The system can be combined with an endoscopic delivery tool, including one or more optical fibers. Laser surgery based on flash vaporization can be performed within a complex parameter space described in more detail below. The discovery of commercially feasible operating conditions for lasers and delivery tools as described herein enables for the first time, a new variety of "cold ablation" surgical techniques.

The spinodal decomposition process generates pressure within the target tissue volume. The pressure is generated, in part, when the chromophore, for example water, in the target volume reaches or exceeds the spinodal threshold, thus initiating spinodal decomposition, on a time scale sufficient to substantially prevent propagation of thermal or mechanical energy beyond the target volume. The pressure generated ejects material from the target site. The amount of pressure to adequately or optimally eject substantially all of the target volume is, in part, dependent upon the mechanical properties of the tissue itself. Various tissue types have different mechanical properties, in part, due to the collagen structure of each tissue type. A comparison of skin to kidney is one example. Skin has a higher tensile strength than kidney Skins higher tensile strength is, in part, due to skins function and the environment skin is exposed too. Additionally skin typically has a lower water content than kidney tissue, resulting in a variation of the effective $\mu_a$ as compared to kidney when water is used as the chromophore. The difference in the effective $\mu_a$ and tensile strength may result in different pulse parameters within the flash vaporization regime to remove the two tissue types. The variation in pulse parameters, in part, reflects the different pressures needed to overcome the tensile strength of each tissue type to eject substantially the entire volume of tissue, including the threshold pressure and the optimal pressure range. Bone is another example where different pressures may be required to eject substantially all of the tissue in the target volume.

Bone typically has a lower water content than soft tissue, which may affect the effective $\mu_a$ when water is the chromophore. The relevant mechanical properties of bone may be related to the force required to fracture bone within the target volume rather than pure tensile strength. The parameters for flash vaporization and the resulting pressure generated may be different for bone when compared to soft tissue.

The localized temperatures generated in the target volume during a flash vaporization event are near or exceed the liquefaction threshold for collagen. At or above the liquefaction threshold for collagen the structural integrity of the tissue may be compromised, weakening the collagen structure. The weakened structures still exhibit variation in mechanical properties for different tissue types. Efficient removal of specific tissue types can be achieved, in part, by generating pressure in the target volume that is sufficient and/or optimal for tissue ejection. Achieving flash vaporization with the ability to generate a range of pressures may be a factor in effectively targeting a wide variety of tissue types.

Equation 4, can be recast by substituting $E/A_r$ for $\phi$, yielding equation 8, for pulses shorter than 1 usec.

$$T = \frac{\mu_a E e^{-\mu_a z}}{C_v \rho A_r} \qquad \text{Equation 8}$$

where:
T=temperature (° C.),
E=energy (J),
$A_r$=area (cm$^2$)
$C_v$=Where $C_v$ is the isochoric specific heat (saturated liquid heat capacity at constant volume) of the chromophore (H$_2$O) (J/g° C.),
$\rho$=density (g/cm$^3$) and
z=depth (cm)
$\mu_a$=absorption coefficient (cm$^{-1}$), The pressure generated in the target site can be calculated from equation 9 for pulses shorter than 1 μsec.

$$P = A\mu_a \Gamma \phi e^{-\mu_a z} \qquad \text{Equation 9}$$

where:
P=Pressure, $$A = \frac{1 - e^\tau}{\tau},$$

$$\tau = \frac{t_p}{t_o},$$

$t_p$=pulse width, $$t_o = \text{characteristic pulse width} = \frac{1}{\mu_a v_s}$$

$v_s$=sound velocity (cm·sec$^{-1}$)
$\Gamma$=Grüneisen parameter (dimensionless), $$\varphi = \text{Fluence} = \frac{E}{A_r}$$

$\mu_a$=absorption coefficient (cm$^{-1}$),
z=depth (cm)
In one embodiment the temperature and/or pressure throughout the interaction volume are considered, specifically the temperature and/or pressure at the optical penetration depth where $$z = \frac{1}{\mu_a}.$$

To achieve the spinodal decomposition threshold temperature at the optical penetration depth $$z - \frac{1}{\mu_a},$$

T can be recast as Equation 10, $$T = Te, \qquad \text{Equation 10}$$

where
T=temperature
e is Euler's number=2.71828

Now the temperature within the full optical penetration depth for each pulse can be determined to meet or exceed the spinodal decomposition threshold thus, in part, initiating flash vaporization throughout the interaction volume.

Similarly to achieve, at least, the threshold pressure at the optical penetration depth $$z = \frac{1}{\mu_a},$$

needed to eject a given target tissue, P can be recast as Equation 11, $$P = Pe, \qquad \text{Equation 11}$$

where:
P=pressure
e is Euler's number=2.71828

Now the pressure within the full optical penetration depth for each pulse can be determined to meet or exceed the pressure threshold needed to eject substantially all the tissue throughout the interaction volume.

Equation 10, in part, determines the lower temperature limit for flash vaporization in H$_2$O throughout, substantially, the entire interaction volume. However the pressure generated may not be enough to overcome the mechanical strength of the target tissue. It may be necessary to adjust the pulse parameters to achieve threshold or optimal pressure to eject substantially all of the tissue within an interaction volume. Additionally each different target tissue type may have different threshold and/or optimal pressures for ejecting the respective tissues. If we re-cast the pressure equation to include the relevant parameters we can see more easily which parameters will have the largest effect.

We have $$\tau = \frac{t_p}{t_o} \ \& \ t_o = \frac{1}{\mu_a v_s}$$

thus $\tau = t_p \mu_a v_s$ and $$\varphi = \frac{E}{A_r}$$

where $A_r = \pi \omega^2$

So:

$$P = \frac{1 - e^{-(t_p \mu_a v_s)}}{t_p v_s} \cdot \frac{\Gamma E}{\pi \omega^2} \qquad \text{Equation 12}$$

where
P=pressure
E=energy (J),
$\mu_a$=absorption coefficient (cm$^{-1}$),
$t_p$=pulse width (sec),
$\omega$=radius of incident spot (cm)
$v_s$=sound velocity (cm/sec)
$\Gamma$=Grüneisen parameter (dimensionless),
We notice immediately that P changes
exponentially as:
the pulse width
the sound velocity
the absorption coefficient
inversely with the square of the spot radius $\omega$
linearly with energy The velocity of sound is a property of the target chromophore and cannot be readily changed for given type of target tissue. The wavelength directly affects the absorption coefficient and may be used independently or in part to achieve a desired pressure. In one embodiment where the wavelength remains constant, any one or combination of pulse duration, energy per pulse and/or spot size may be changed to achieve a desired pressure for ejecting a specific target material. Each parameter indicated in equation 12 may individually or in combination be adjusted to achieve a desired pressure. Within the multivariable parameter space that achieves a desired pressure, generating and/or delivering a pulse with certain parameters may be impractical. For example a certain range of pulse energy and pulse durations may achieve a desired pressure according to equation 12, but no laser source may exist to achieve the particular pulse energy and pulse width combinations.

Similarly the ability, in practice, to deliver a pulse to a target tissue should be considered. For example, even in the absence of a waveguide, certain subsets of parameters within a parameter space achieving, at minimum, flash vaporization and tissue specific pressure thresholds may generate plasma at the tissue or in air which may interfere with the delivery of the pulse to tissue and therefore ultimately may not satisfy the conditions within the tissue volume for flash vaporization and/or pressure to eject the target tissue.

A waveguide, in some instances, may be selected such that a range of pulse parameters can be successfully transmitted through the waveguide and subsequently adjusted, typically by focusing elements, to achieve flash vaporization with a pressure sufficient to eject, substantially, the entire target volume.

For many surgical applications it may be advantageous to use a waveguide where the waveguide core is roughly the same diameter as the treatment spot size. One embodiment where the waveguide core and treatment spot size are similar is when the waveguide is used in contact to or near contact to the target tissue.

Silica fibers are a dominate type of waveguide used to delivery laser energy for endoscopic applications. Silica fibers are readily available, flexible, biocompatible and low cost. Silica fiber waveguides are a preferred embodiment for utilizing flash vaporization for many tissue cutting applications, including endoscopic procedures. The pulse parameters used to achieve flash vaporization and/or pressure sufficient to eject the target material have, in part, high peak power. High peak power can damage silica based waveguides. A preferred embodiment is therefore a range of laser pulse parameters that both achieve flash vaporization with an appropriate pressure to eject the material for a given target and can be reliably transmitted down a silica based fiber without catastrophic damage to the silica fiber. The theoretical bulk damage limit for silica fiber is known across a broad range of pulse durations, including a subset of pulse durations suitable for flash vaporization. In practice the theoretical limits have not been fully achieved. Studies have shown the practical relationship between pulse energy and pulse width follows equation 13

$$E_i = a d^b t_{min}^c \qquad \text{Equation 13}$$

where:
Where: a, b and c are coefficients that have been determined experimentally
a=3921.5
b=0.95
c=0.5
$E_i$=energy (J)
$t_{min}$=pulse width (sec)
d=fiber core diameter (cm)

For example, by knowing the target tissue type and selecting a wavelength, essentially $\mu_a$, $V_s$, $C_v$, $\rho$ can be determined. Then by substituting equation 13 into the relevant previous equations a parameter space, if it exists, for a given the tissue type, wavelength and fiber damage threshold, can be determined such that condition for flash vaporization with sufficient pressure to eject the target material can be meet, including delivery with a silica fiber.

Cutting Rate Experiment

Figure 6:
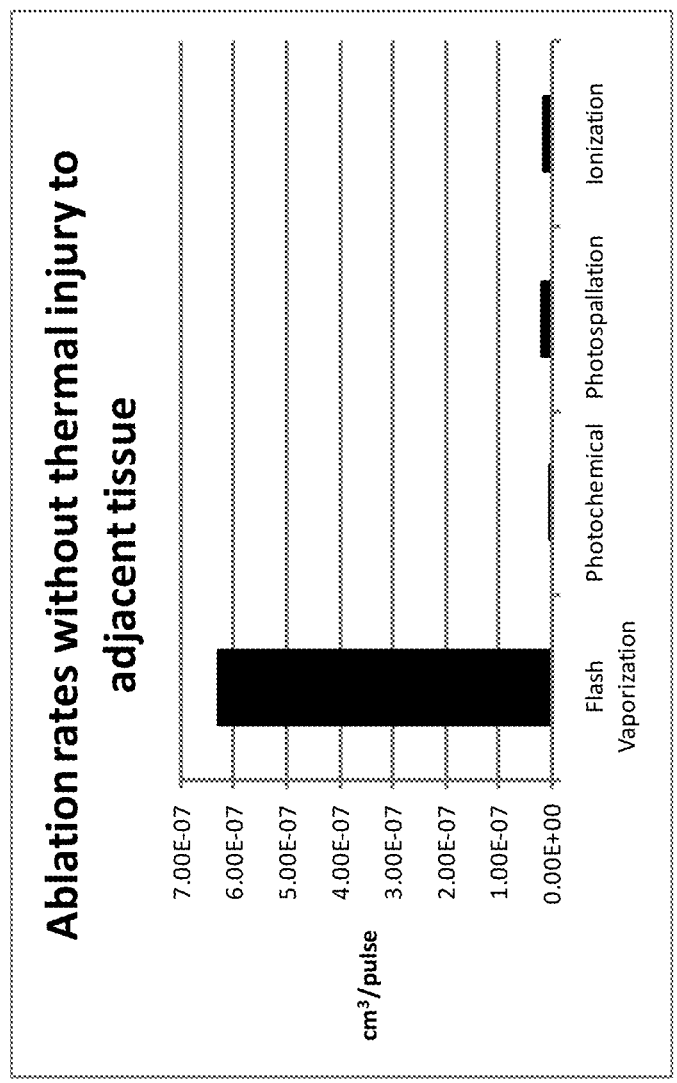
FIG. 6 shows a bar chart comparing cutting rates for various forms of resection, in accordance with embodiments.

A flash tissue vaporization based laser system operating at a 1.94 um wavelength was built and used to conduct ex-vivo tissue cutting tests. The pulse energy used was approximately 3.5 mJ and was delivered through a silica based fiber optic waveguide, and the pulse repetition rate was 400 Hz. The fiber tip was positioned in a mount and held in a fixed location. The movable test stand with a porcine kidney tissue sample was moved through the beam immediately in front of the fiber tip. The approximate length of the tissue sample was 2 cm with a thickness of approximately 2 mm. The flash vaporization system cut through the entire sample in 8 seconds. The system made a 2.5 mm long by 2 mm deep cut each second. The volume of tissue removed per pulse was $6.28 \times 10^{-7}$ cm$^3$/pulse. This cutting rate is dramatically faster than prior art laser systems. For example an excimer laser system with similar pulse repetition rates and incident spot size with the fluence optimized to operate in a mode without adjacent thermal injury yields a rate of $3.14 \times 10^{-9}$ cm$^3$/pulse, 200 times slower. Similarly a photospallation based Erbium YAG system with similar pulse repetition rates and incident spot size with the fluence optimized to operate in a mode without adjacent thermal injury yields a volume removed per pulse of $1.57 \times 10^{-8}$ cm$^3$/pulse, 40 times slower. A high power research oriented femtosecond system with similar pulse repetition rates and incident spot size with the fluence optimized for ablation without adjacent thermal injury yields a rate of $1.49 \times 10^{-8}$ cm$^3$/pulse, over 40 times slower as well. FIG. 6 shows a bar chart comparing cutting rates for various forms of resection without substantially any adjacent tissue injury. The photochemical, photospallation and ionization based systems do not have a suitable means for fiber delivery for typical surgical applications and are typically limited to line of site delivery.

Figure 7A:
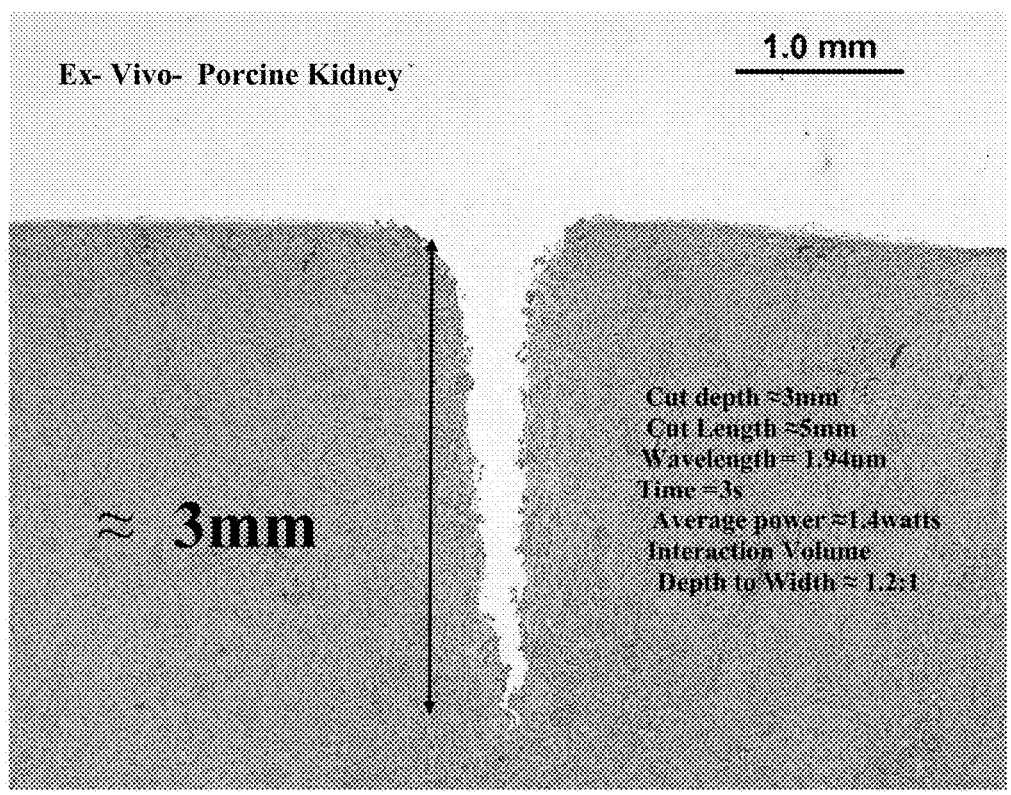
FIGS. 7A and 7B are images showing histology obtained from tissue resection performed with a laser system, in accordance with embodiments as described herein.
Figure 7B:
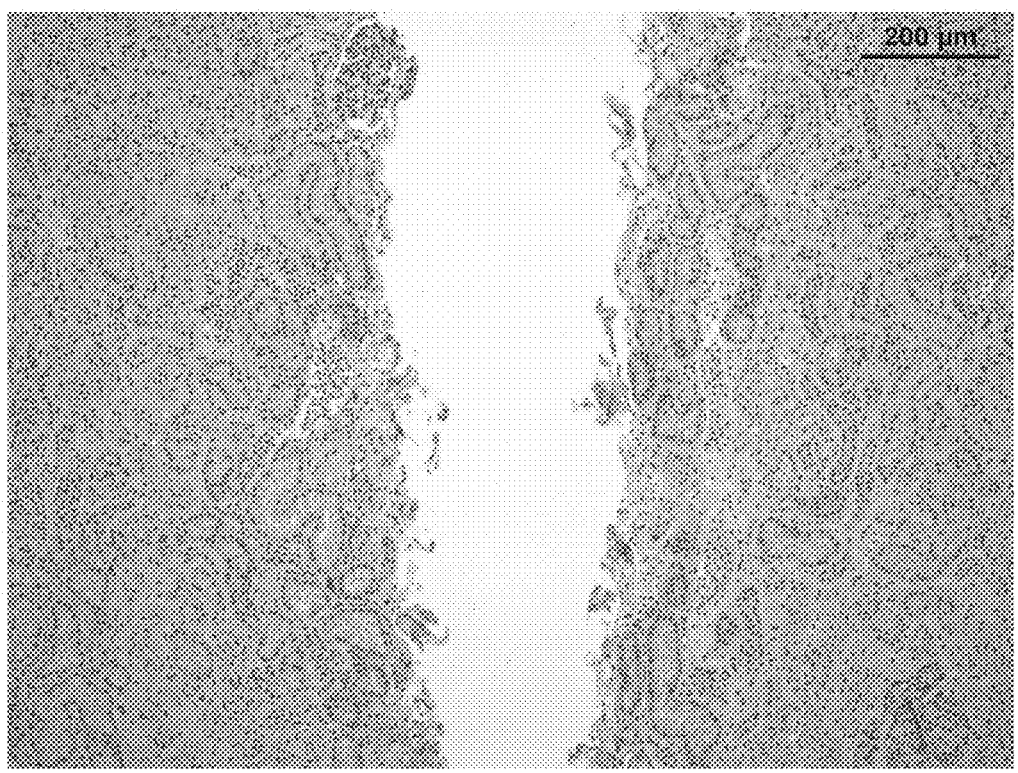

FIG. 7a is H&E stained histology of a cut made in ex-vivo porcine kidney with the Flash Vaporization system. The cut was approximately 3 mm deep by 5 mm long and took approximately 3 seconds to perform with an average power of approximately 1.4 watts and a depth to width ratio of 1.2:1. The histology shows a clean cut with no apparent thermal injury to the tissue adjacent the cavity left by the ejected tissue. FIG. 7b is a higher magnification image of the same tissue sample. The cut surface shows no apparent thermal injury. Flash Vaporization enables previously unobtainable high speed cutting rates for deeper incisions with no apparent thermal injury to the adjacent tissue. Also, no mechanical injury is seen, except on the microscopic scale that would not materially lengthen healing rates.

For some surgical procedures it may be desirable to remove a large mass of tissue directly via Flash Vaporization rather than by excision. For example a surgical treatment for Benign Prostatic Hyperplasia may involve removal of a large mass of prostate tissue. The removal of prostate tissue can be achieved either via an excision style process or a mass tissue vaporization process, depending on the surgeon's preference. Removal of tissue in the colon is another example where removal directly via Flash Vaporization may be advantageous. Sessile colon tumors are embedded in the inner wall of the colon and may be difficult to remove by excision. The ability to vaporize the tumor in layers, without collateral damage, from the surface down to healthy tissue may be advantageous.

Referring to equations 7 and 12 and the related equations described herein there is at least one combination of parameters that provide the optimal tissue ablation efficiency, maximum grams of tissue ablated per joule. When operating at the optimal efficiency the maximum tissue vaporization rate can be achieved. The tensile strength of tissue types varies throughout the body thus it is evident that the optimal parameters required to remove the target tissue will vary. This is achieved by optimizing the pressure in the target volume. For example the pressure required for optimum vaporization of the dermis is significantly higher than required for kidney The maximum speed at which tissue can be vaporized via Flash Vaporization corresponds to the optimal ablation efficiency. Therefore a problem exists when the surgical procedure requires/desires a rate of ablation that is greater than the rate of ablation corresponding to the peak ablation efficiency. To achieve ablation rates that exceed the maximum ablation rate described above, a novel delivery device with two or more fiber optic waveguides may be used. As spot size increases, the energy per pulse needed to achieve ejection by spinodal decomposition increases significantly. This limits the size of a laser spot than can be practically used in laser surgery applications.

Species of laser systems described herein are configured to remove larger volumes of tissue per unit time. Such species utilize lasers capable of producing outputs that are a multiple of the energy per pulse to be applied by each pulse. In such species, a delivery tool including multiple waveguides can be coupled to the laser system for delivery of multiple spots, preferably adjacent, of laser energy to the treatment site in parallel or in rapid sequence. As there is essentially no residual energy in the tissue after ejection, the multiple spots are treated essentially independently. High repetition rates and multiple spots can be used to achieve very high tissue removal rates.

A laser source may be capable of producing energy/power well beyond the amount required to achieve optimal ablation efficiency. Delivering a laser pulse to tissue with a fluence, for instance, greater than the peak efficiency reduces the ablation efficiency and in some cases may even exceed the damage limits for a single fiber optic waveguide. By dividing a laser pulse generated within the laser source and coupling the pulse into multiple fibers each individual fiber can simultaneously receive a portion of the pulse energy. Furthermore, by aligning the individual fiber outputs to separate regions of the target tissue, typically adjacent to one another, each fiber can be configured such that the tissue at each fiber's individual treatment site is ablated with optimal ablation efficiency. Utilizing a laser system with multiple delivery fibers allows most or all of the available laser energy generated by the laser source to be applied to tissue achieving Flash Vaporization with optimal ablation efficiency. Multiple delivery fiber configurations increase the system's overall ablation rate to meet clinical needs where it is desirable to directly vaporize tissue faster than a single delivery fiber can achieve while maintaining Flash Vaporization with optimal ablation efficiency.

Figure 8:
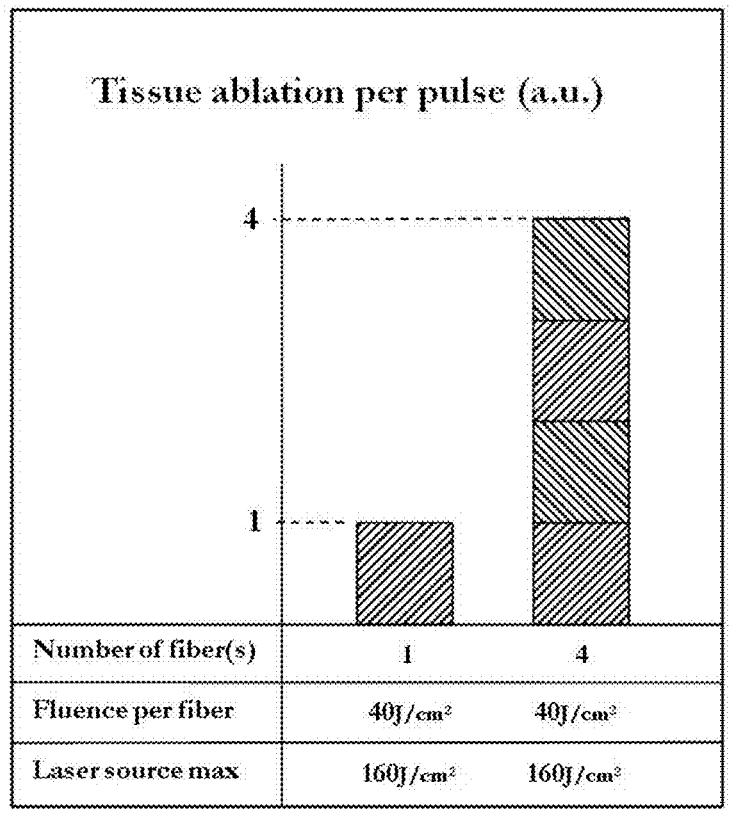
FIG. 8 shows tissue removal for single fiber Flash Vaporization system versus a 4 fiber Flash Vaporization system.

For example it may be necessary to ablate a large brain tumor. The use of parallel pulse delivery to achieve high ablation rates can be understood with reference to the table shown in FIG. 8. Assume Flash Vaporization at the optimal ablation efficiency is achieved with a fluence of about 40 $J/cm^2$. As discussed increasing the fluence beyond 40 $J/cm^2$ does not improve the ablation speed. An exemplary laser may be capable of generating a pulse within the Flash Vaporization parameter space that well exceeds the 40 $J/cm^2$, for example a pulse that would equate to 160 $J/cm^2$, 4 times greater than what is required for optimal efficiency. By generating a pulse capable of supporting 160 $J/cm^2$ and then dividing the pulse simultaneously and roughly equally among 4 individual fibers, each fiber can delivery to tissue a fluence of 40 $J/cm^2$, at optimal efficiency in parallel. When the fiber output ends are arranged to treat separate tissue regions, typically adjacent to one another, 4 times more tissue per pulse is removed while maintaining optimal ablation efficiency.

The increased rate of tissue ablation achieved by utilizing multiple fibers has been described for an individual pulse, but is applicable to a sequence of pulses as well. For faster tissue ablation the multiple fibers are typically an integrated part of the delivery device with each fiber output corresponding to separate treatment site, typically adjacent to one another. The number of fibers utilized is scalable within the limits described.

In the example of sessile colon polyps one could choose to use a fiber bundle arranged in a semi-circular fashion with five fibers, where the laser can produce a pulse capable of generating a fluence five times larger than the single fiber optimal ablation efficiency fluence. The pulse can be divided equally into 5 parts and then coupled simultaneously into 5 individual fibers. For each laser pulse generated, 5 times more tissue is removed than can be achieved with a single fiber.

Figure 9:
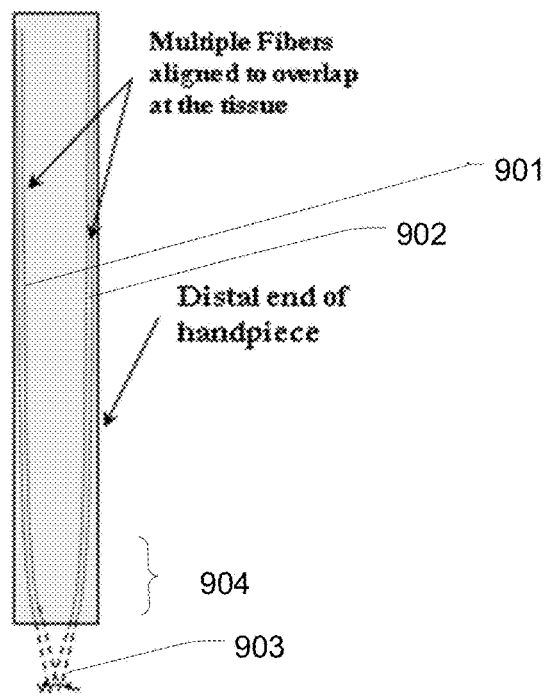
FIG. 9 shows a multi-fiber delivery system where the individual fiber outputs are overlapped at the treatment site.

Some tissue types have relatively high mechanical strength and require higher pressures to break apart the tissue matrix. A significant limitation occurs if the Flash Vaporization parameters required to achieve the necessary pressure exceeds the power handling capabilities of a single silica fiber, as described in Equation 13. For example the collagen of the dermal matrix is very strong and elastic. The pressure required to achieve Flash Vaporization in the dermis is higher than most other soft tissues. For the dermis example, a reasonable assumption for the fluence required for Flash Vaporization might be 200 J/cm² this however exceeds the capability of the fiber thus we are presented with a challenge. This problem can be readily addressed by utilizing multiple fibers arranged in a configuration such as that illustrated in FIG. 9. Multiple fibers 901, 902 configured so that the output overlap in a single spot in the region 903 on the treatment site enable Flash Vaporization pressures far in excess of that achieved by a single fiber. An exemplary laser would generate the requisite energy for optimization of fluence at the target through two or more fibers. At or near the distal end 904 of the device, the output beams of the fibers are organized to overlap one another at the treatment site. For example each fiber carries a pulse corresponding to the equivalent of 100 J/cm², well below the fiber damage threshold. The fibers are configured such that the output beams overlap completely thus achieving 200 J/cm² at the treatment site. Using multiple fibers enables Flash Vaporization to occur with fiber delivery in tissues where single fiber deliver cannot achieve Flash Vaporization. One embodiment for the delivery device is to have the fibers bent and/or angled near the output such that the output beams overlap completely at the treatment site, as illustrated in FIG. 9. The delivery device may have slots, grooves or some physical means to align and secure each fiber such that the output beams are overlapped at the treatment site.

Figure 10:
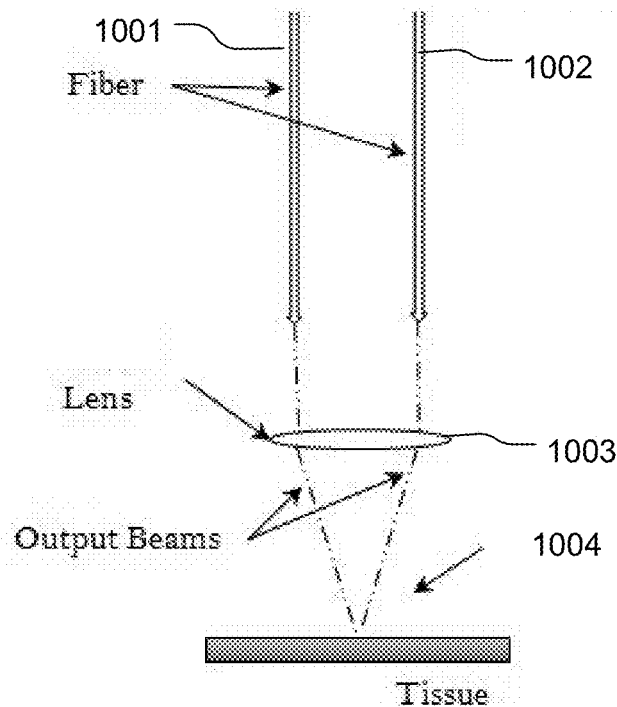
FIG. 10 shows an alternative multi-fiber delivery system where the individual fiber outputs are overlapped at the treatment site.

An alternative embodiment may employ focusing optics near the device tip Such as shown in FIG. 10. In FIG. 10, a plurality of fibers 1001, 1002 arranged in a manner such as might occur through an endoscope. At the distal end, a lens 1003 is positioned to redirect the outputs of the plural fibers 1001, 1002 so that they overlap on a spot 1004 on the treatment site on the tissue. Each fiber 1001, 1002 is positioned and secured in the delivery device such that the output beam passes through an optical element (e.g. lens 1003) that in part ensures the output beams of each fiber overlap at the treatment site. The optical element may be an integral part of the fiber tip such as a shaped tip, graded index fiber tip, tapered tip or other bonded, fused, attached or modified tips contributing to directing light. Additionally the optical element may be a single lens, individual lenses for each fiber, or any other configuration of optical element(s) that ensures overlap at the treatment site for each fiber output as illustrated in FIG. 10.

Achieving higher pressures during Flash Vaporization via the recombination of multiple fiber outputs can employ two or more fibers, one or more optical elements and/or numerous mechanical positioning and mounting configurations.

Figure 11A:
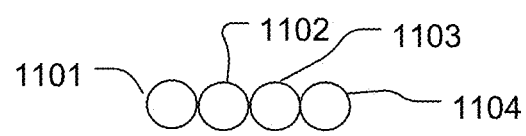
FIGS. 11a and 11b show a multi-fiber delivery device tip with the outputs arranged linearly and adjacent to one another and an exemplary direction of motion.

FIG. 11a illustrates a linear arrangement of fiber tips 1101, 1102, 1103, 1104 that can be utilized in a delivery tool, to provide for increased rate of cutting. The fiber tips 1101, 1102, 1103, 1104 in this example are positioned in a line, and adjacent to one another. Utilizing multiple fibers for faster tissue ablation additionally enables customized tip geometries that can be shaped to accommodate the needs of a given procedure.

Figure 11B:
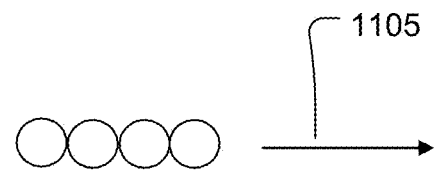

When a delivery device is configured in a line and is moved such that the line is along the cut direction represented by arrow 1105, see FIG. 11b, a scalpel like cutting effect is achieved. The direction of motion mimics a standard scalpel, enabling cuts to be made faster than achievable with a single fiber.

Figure 12:
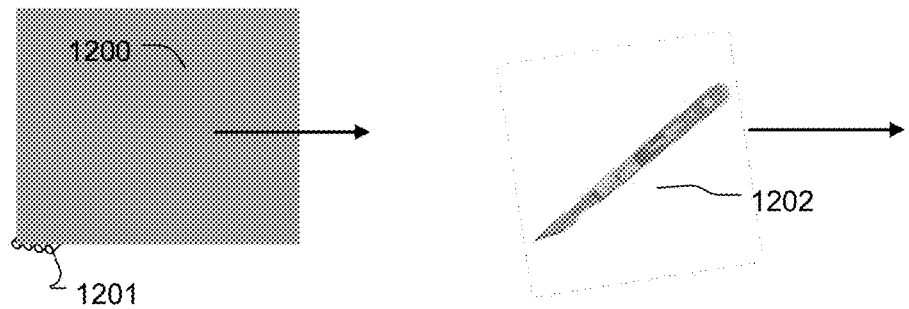
FIG. 12 shows an exemplary multi-fiber device configured to mimic a scalpel.

Alternatively the fiber tips can be staggering to provide an angle with respect to the tissue. FIG. 12 is a perspective view of a four fiber delivery tool 1200 in which the fiber tips 1201 are arranged in a staggered configuration, where a first fiber extends distally relative to the laser source by a small stagger relative to a second fiber, and so on in a stairstep configuration through all of the fibers in the line. The sizes of the stairstep can be equal or varied as suits the needs of a particular arrangement. Representative sizes of the stairstep can be on the same order as the diameter of the fibers or smaller, for example. In the configuration of FIG. 12, the direction and angle of the device handle can mimic a scalpel 1202 ergonomically.

Figure 13:
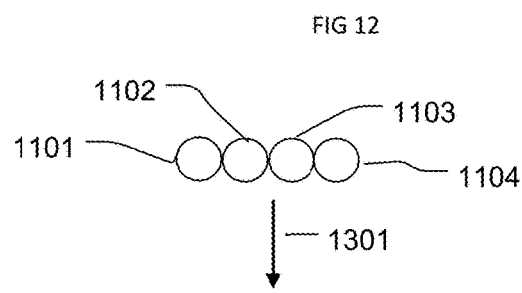
FIG. 13 shows an alternative direction of motion for a linear fiber tip arrangement.

With a linear device tip configuration, mass vaporization can be achieved be moving the device in the direction perpendicular to the fiber arrangement. As represented in FIG. 13, by the arrow 1301, a linear device tip including a plurality of fibers, such as fibers 1101-1104, can be moved in a direction orthogonal to the line of fibers.

Figure 14A:
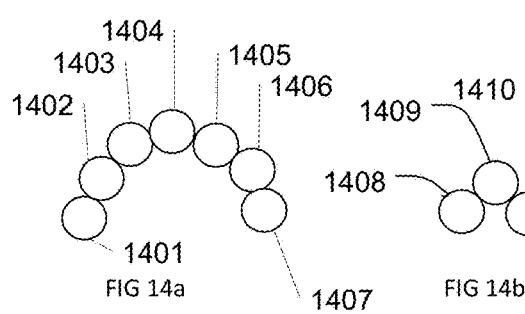
FIGS. 14a-14c show exemplary multi-fiber device tip configurations for rapid tissue ablation.
Figures 14B, 14C:
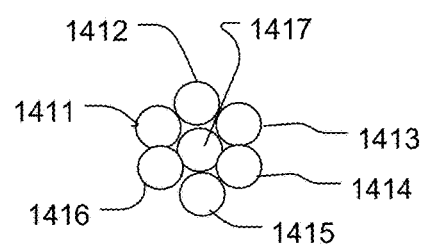

When this configuration is moved across a target tissue it provides rapid ablation of a strip width equal to the width of the fiber arrangement. FIG. 14a illustrates an arrangement of fiber tips 1401-1407 in a semicircular shape, as an alternative beam delivery tool. FIG. 14b illustrates yet another alternative, in which three fiber tips 1408-1410 are arranged in a nonlinear triplet. FIG. 14c illustrates a tightly packed cluster of fiber tips, where six fibers 1411-1416 surround a central fiber 1417.

Figure 15A:
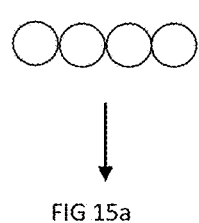
FIGS. 15a-15b shows directions of motion and exemplary multi-fiber device configurations.
Figure 15B:
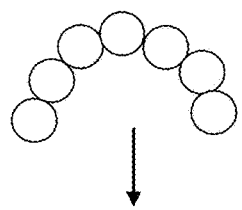

Each tip configuration can be chosen to accommodate the clinical need. The treatment spots created by each individual fiber would be unique and in general adjacent to one another. For example to debulk a sessile colon polyp a linear or curved arrangement may be employed such that the tip is drug across the tissue achieving vaporization over a large surface area per pass than a single fiber, as illustrated generally in FIGS. 15a and 15b.

Figure 16:
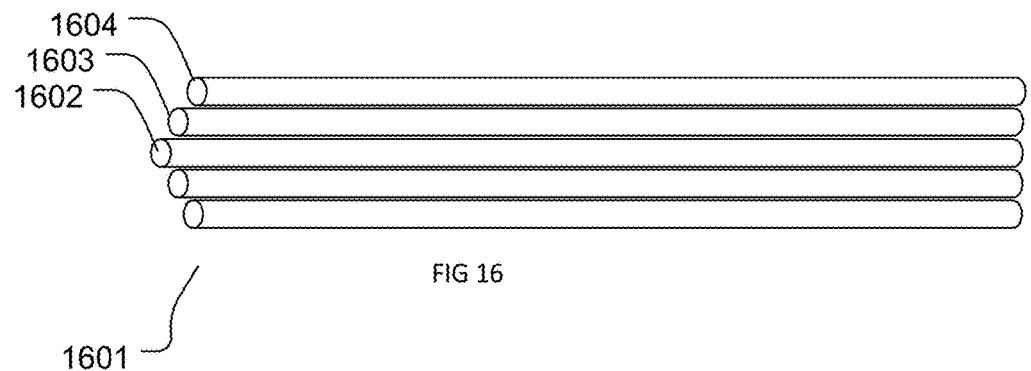
FIG. 16 shows an exemplary multi-fiber device tip configuration for generally spherical tumors.

For vaporization of tumors with a generally spherical shape, a multi-fiber tip 1601 may be used where the central portion 1602 protrudes further into the tissue than the fiber tips (e.g. 1603, 1604) closer to the edges, as illustrated in FIG. 16.

Figure 17:
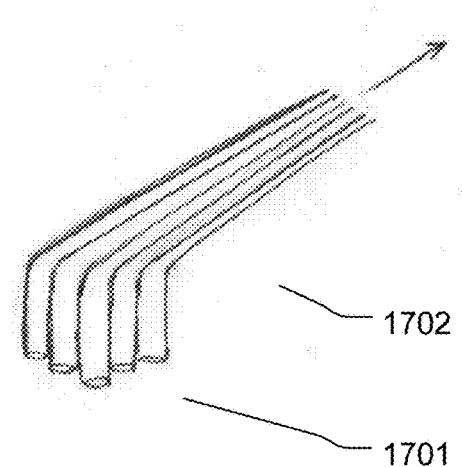
FIG. 17 shows an exemplary multi-fiber device tip configuration for generally cylindrical tumors.

For vaporizing tissue along the longitudinal axis of a generally cylindrical shape, such as in transurethral prostate resection, a tip 1701 with fiber tips arranged in a curved configuration can be used, with a near right angle bend 1702 employed to direct energy laterally, and quickly vaporize a large mass of tissue, as shown in FIG. 17.

Figure 18:
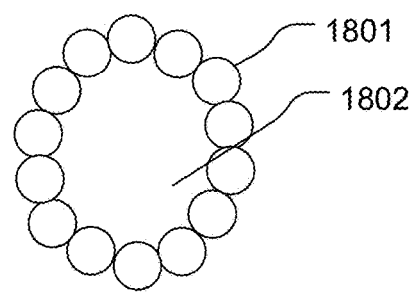
FIG. 18 shows an exemplary multi-fiber device tip configuration for pace maker lead removal.

For removal of pacemaker leads a device that can be inserted coaxially with the wire lead is desirable. FIG. 18 shows a delivery device with a circular fiber arrangement 1801, with an open center 1802, which may enable Flash Vaporization of the tissue adhered to the wire's outer surface, allowing the lead to be detached and removed.

A tight circular formation can be used when mass tissue vaporization is needed and a painting motion over the diseased tissue is desirable. Using a painting motion the surgeon can control the depth of vaporization by hand to achieve a desired margin, for example to efficiently resect a tumor with large variations in depth, as shown in FIG. 14c.

In order to use multiple delivery fibers a means to direct all or a portion of the laser energy into two or more fibers is necessary. Passive components such as partial reflectors are non-limiting examples of components that may be used to direct predetermined portions of the laser beam into multiple directions. Active components such as rotating mirrors are non-limiting examples of active means to direct portions of the laser beam in multiple directions. The beam path may be serial, parallel or any permutation of serial and parallel. The percentage of light from the source that is transmitted and ultimately coupled to each fiber may be static as determined by a beam directing component. Alternatively active components such as shutters, modulators, attenuators and the like may be used to control when and what percentage of the source light is coupled into any individual fiber.

For example a 4 fiber arrangement such as shown in FIG. 19, including fibers 1900-1903 may be desirable for large volume tissue ablation. This arrangement can be used with a system like that of FIG. 20. In this example the laser source 2000 generates a pulse that can be divided equally into 4 fibers while providing tissue ablation via Flash Vaporization for each fiber at adjacent tissue sites. In the arrangement of FIG. 20, the laser source 2000 generated output that intersect beam splitter 2001, which passes 25% of the energy through a fiber coupling lens into fiber 1900. The remaining 75% of the energy is directed past the shutter 2002 to a second beam splitter, which deflects one third of the remaining 75% (i.e. 25% of the original energy) through a fiber coupling lens into the fiber 1901. The remaining 50% of the original energy is directed to a third beam splitter 2004, which deflects one half of the remaining 50% (i.e. 25% of the original energy) through a fiber coupling lens into the fiber 1902. The final 25% of the original energy is directed to the reflector 2005, through a fiber coupling lens into the fiber 1903. When mass tissue vaporization is required the shutter 2002 is open and all four fibers will Flash Vaporize the target tissue. When precise cutting is needed the shutter 2002 is closed and only one fiber receives a portion of the source pulse to Flash Vaporize the target tissue. Of course other arrangements of shutters and beam splitters can be utilized to implement a desired control sequence.

For embodiments with two or more laser sources similar fiber coupling techniques can be used.

One embodiment utilizes one or more fibers of a delivery device for Flash Vaporization and one or more different fibers of the same device for coagulation purposes. This is represented schematically in FIG. 21, in which a first fiber 2100 is used for flash vaporization, and a second fiber 2101 is used for delivering energy for coagulation. In some instances the coagulation fiber(s) may have different core sizes than the Flash Vaporization fiber(s) or than each other. The coagulation fiber(s) tip may be flush with the Flash Vaporization fiber tip(s) or positioned back from the Flash Vaporization fiber tip(s). One advantage of an offset coagulation fiber tip is that the laser energy transmitted down the coagulation fiber may have similar or identical energy, pulse duration, wavelength characteristics to the laser energy transmitted down the Flash Vaporization fiber but since the coagulation fiber is position such that the interaction volume exceeds that required for Flash Vaporization the delivered energy results in coagulation. It may also be desirable to heat tissue over larger area than the Flash Vaporization interaction area, again offsetting the coagulation fiber can help achieve the larger coagulation area.

Regardless of the fiber configurations the coagulation fiber(s) may transmit different energy, pulse duration, repetition rate and/or wavelengths than are used with Flash Vaporization fibers(s) to provide a means for coagulation. In some cases the coagulation fiber(s) may be disabled while Flash Vaporization is occurring or vice versa. Alternatively the Flash Vaporization and coagulation fibers may be enabled simultaneously.

Another embodiment is to change the operating mode of the laser between Flash Vaporization and coagulation modes while directing the laser energy down any combination of fibers for a given multi-fiber device. For example the laser system may produce a repetitive sequence of several Flash Vaporization pulses followed by a period of continuous wave energy. In the example of a tightly packed circular multi-fiber tip the Flash Vaporization/Coagulation sequence can be directed down each fiber roughly equally.

Any of the above mentioned multi-fiber delivery device tip arrangements may actively control the transmission through each individual fiber. A circular arrangement as described for use with a painting motion can remove tissue very rapidly. If a surgeon needed to make small precise cuts occasionally during this mass ablation process the Flash Vaporization pulse energy can be directed only down 1 of the fibers, for example the center fiber, as represented in FIG. 22 by darkening the exterior fibers in the cluster. This exemplary deliver device and laser system can maintain the precise cutting capability of a single fiber and have the rapid mass tissue ablation capability enabled by using multiple fibers within the Flash Vaporization parameter space. An additional embodiment is a scalpel like device configuration with a broad range of cutting rates, as illustrated schematically by the light and dark fiber tips in FIGS. 23a, 23b, 23c and 23d. The slowest cutting rates correspond to only 1 fiber being enabled to deliver Flash Vaporization pulses. Slow cutting rates may be achieved by enabling 2 fibers. Faster cutting rates may be achievable by enabling 3 fibers. The fastest cutting rates may be achieved with all 4 fibers.

Virtually any combination of enabled/disabled fibers within an arrangement can be chosen and in some cases dynamically controlled via an user interface or even within a system's internal programming.

Utilizing multiple fibers greatly expands the clinical capabilities of a Flash Vaporization tissue removal system.

Figure 24:
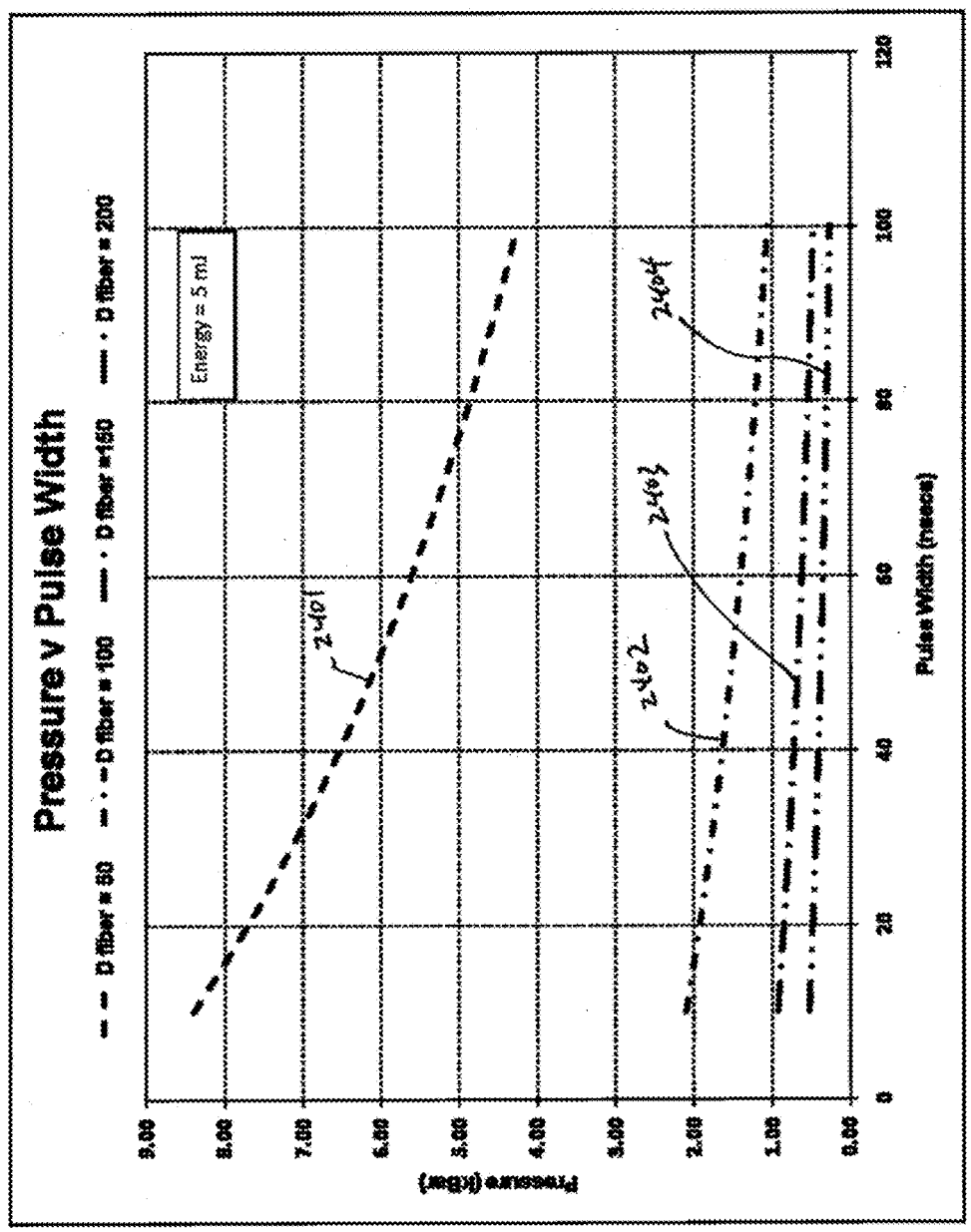
FIGS. 24-27 are plots illustrating aspects of the parameter space which must be taken into consideration in systems employing flash vaporization is described herein.

FIG. 24 is a graph of pressure (kBar) versus pulse width (nsec) for energy of 5 mJ per pulse at a representative wavelength of about 1940 nm. In the graph, trace 2401 corresponds to the results using a 50µ core diameter fiber. Trace 2402 corresponds to a 100µ core diameter fiber. Trace 2403 corresponds to a 150µ core diameter fiber. Trace 2404 corresponds to a 200µ core diameter fiber. Greater pressures are achievable using smaller fibers, because of the volumetric power density is higher. However, the ability of a fiber to carry sufficient energy per pulse can limit the pulse with usable. For example, a 50µ fiber may not be able to carry 5 mJ at pulse widths of less than 40 nsec. For perspective, it is found that pressures in the range of about 200 Bar to about 10 kBar are desirable for most types of tissue. It can be seen from trace 2402 therefore that a 100 µm core diameter fiber can be readily usable over the desired range using less than 10 mJ per pulse.

Figure 25:
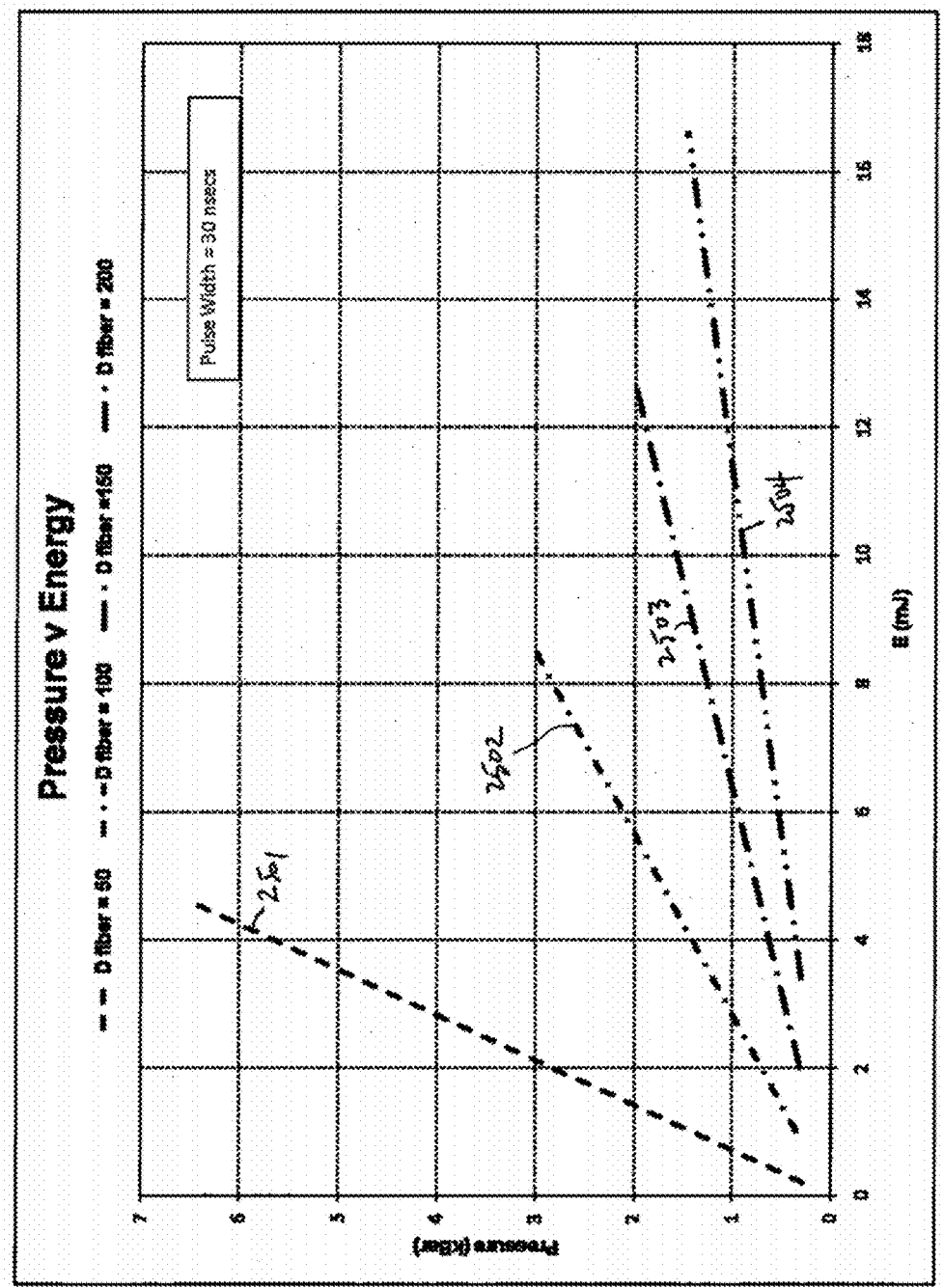

FIG. 25 is a graph of pressure (kBar) versus energy (mJ) for a pulse width of 30 nsec. In the graph, trace 2501 corresponds to the results using a 50µ core diameter fiber. Trace 2502 corresponds to a 100µ core diameter fiber. Trace 2503 corresponds to a 150µ core diameter fiber. Trace 2504 corresponds to a 200µ core diameter fiber. Each trace 2501-2504 terminates at about the limit in millijoules per pulse for that pulse width imposed by the fiber core diameter. Again, this plot illustrates that a 100µ fiber is readily usable over the desired range of pressure. It can be noted that as the pulse width increases from the example here of 30 ns, the amount of allowable energy transmitted through a fiber increases significantly more slowly than the pulse width.

Figure 26:
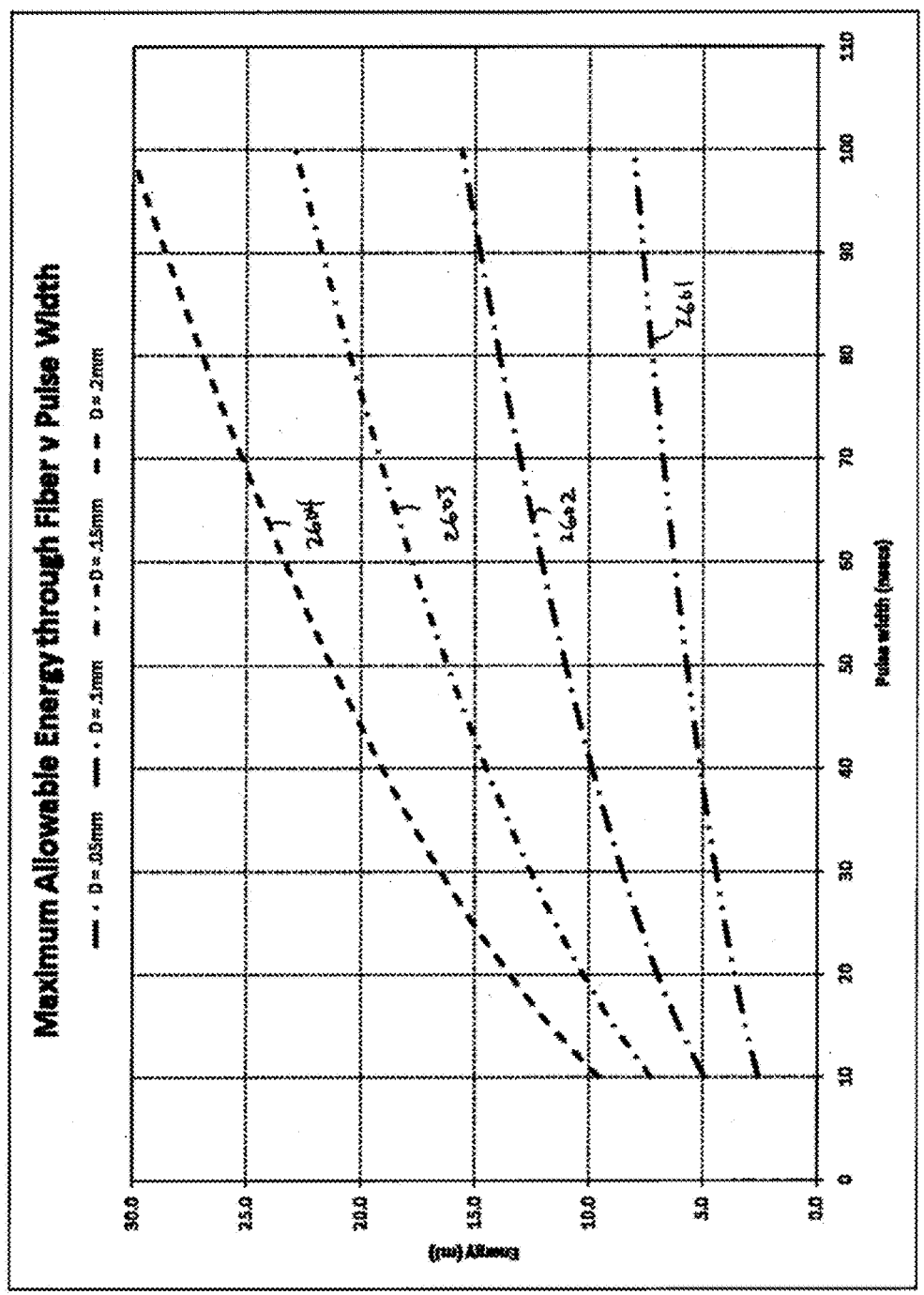

FIG. 26 is a graph of the maximum allowable energy (mJ) through a fiber as a function of pulse width (nsec). In the graph, trace 2601 corresponds to the results using a 50µ core diameter fiber. Trace 2602 corresponds to a 100µ core diameter fiber. Trace 2603 corresponds to a 150µ core diameter fiber. Trace 2604 corresponds to a 200µ core diameter fiber. These plots illustrate that for a given fiber core diameter, one needs to increase the pulse width from about 10 ns to about 100 ns to enable delivery of only three times the maximum energy per pulse. Also, since flash vaporization sets a maximum pulse length on the order of 100 ns for this example, the amount of energy per pulse deliverable through fiber is significantly limited. The plot illustrates that a fiber core diameter of about 100µ is a suitable delivery tool across the preferred range.

Figure 27:
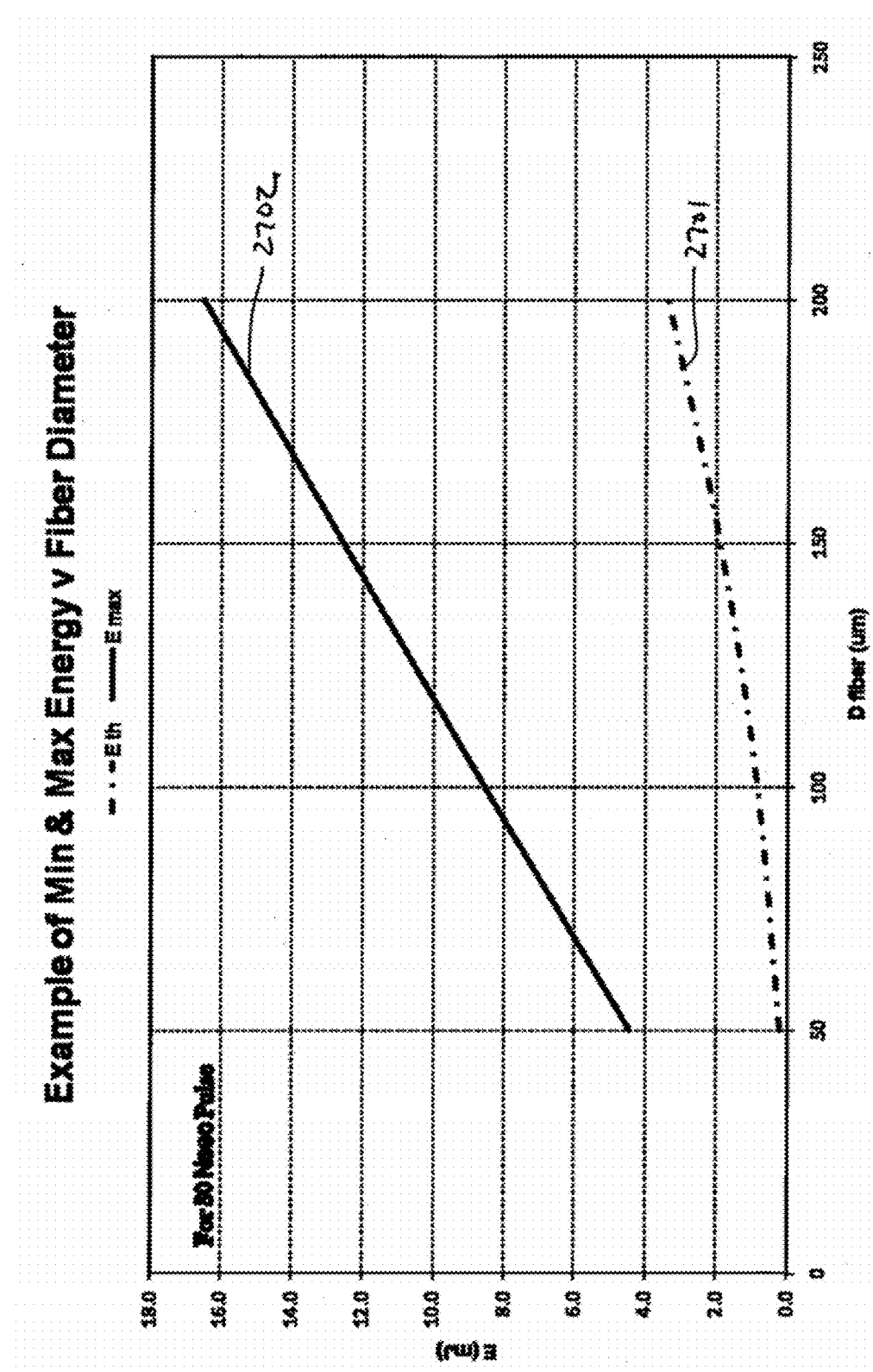

FIG. 27 is a plot energy (mJ) per pulse for 30 ns pulse, versus fiber core diameter (microns). Trace 2701 shows the threshold energy for inducing spinodal decomposition. Trace 2702 shows the maximum energy deliverable in a 30 ns pulse for a given fiber core diameter. The region between the traces 2701 and 2702 shows a suitable working parameter space for flash vaporization.

Embodiments of the present invention can utilize flash vaporization to quickly and efficiently cut and resect one or more of many tissue types, for example without substantial thermal or mechanical damage to the tissue adjacent to the cut into the tissue. Removing tissue with decreased damage to the adjacent tissue regions can improve clinical outcomes, reduce the risk of adverse events and expedite the patient's recovery. A laser can produce pulses of light energy to eject a volume of the tissue, and the energy can be delivered to a treatment site through a waveguide, such as a fiber optic waveguide. The incident laser energy can be absorbed within a volume of the target tissue with a tissue penetration depth and pulse duration such that the propagation of the energy from the tissue volume is inhibited and such that the target chromophore within the volume reaches the spinodal decomposition threshold and subsequently ejects the volume, for example without substantial damage to tissue adjacent the ejected volume.

In a first aspect, embodiments provide a method of removing tissue with light energy. A pulsed beam of the light energy is directed toward the tissue. Each pulse irradiates a volume of tissue and has a duration and an amount of energy to inhibit stress and thermal energy propagation from the volume such that the volume of the tissue is ejected via the mechanism of spinodal decomposition.

In many embodiments a pulsed beam of the light energy is directed toward the tissue. Each pulse irradiates a volume of tissue with a given energy and a duration short enough that most if not substantially all of the stress and thermal energy is confined within the volume and the tissue is ejected via the mechanism of spinodal decomposition. Furthermore energy, pulse duration and additional parameters described herein are selected for a given target tissue to achieve spinodal decomposition with substantial stress and thermal confinement, generating sufficient and/or optimal pressure within the target tissue to exceed the mechanical strength, tensile strength is some instances, of the target tissue such that substantially all the tissue within the interaction volume is ejected. Additionally the sufficient and/or optimal pressure may vary depending on the target material's characteristics.

In many embodiments, the target volume is heated with substantial stress and thermal confinement above a threshold of spinodal decomposition to a temperature of at least about 300 degrees C., such that a temporally and spatially uniform phase transition occurs within the volume to eject the volume without substantial energy deposition to tissue adjacent to the target volume. The temporally and spatially uniform phase transition within the entire target volume can create a confined recoil stress so as to efficiently remove the volume without depositing substantial energy in the surrounding region.

In many embodiments, the volume is ejected without substantial stress propagation of mechanical energy from the volume and without substantial thermal diffusion of thermal energy from the volume. The pulse duration may correspond to a dimension across the volume and a stress wave propagation time across the volume so as to substantially inhibit propagation of a stress wave from the volume.

Flash vaporization can be induced, given an optical penetration depth, OPD, as a function of the wavelength of the beam and the absorption coefficient for that wavelength in a primary chromophore such as water in the tissue, using a cross sectional dimension of the beam at the target tissue sized to define an interaction volume such that on spinodal decomposition of the chromophore, the resulting pressure induced kinetic energy, causes ejection of remaining tissue in the target volume. Also, as a result of the size of the volume of tissue ejected by each pulse and the pulse repetition rates applied, the rate of cutting accomplished using flash vaporization can be comparable to that possible when making fine incisions using a scalpel. Flash vaporization can be induced using a pulse duration short enough to maintain substantially stress confined interaction with the tissue, such that damage to surrounding tissue caused by tearing or other stress is not visible or not significant in terms of its effect on healing rates. Also, flash vaporization can be induced using a pulse duration short enough to maintain substantially thermally confined interaction with the tissue in the target volume, such that damage to surrounding tissue caused by heat is not visible or not significant in terms of its effect on healing rates. Flash vaporization can be induced using a wavelength suitable for delivery using silica optical fibers, or other flexible waveguides, while the pulse duration is long enough to allow delivery through the waveguide with only minimal damage or wear, so that fiber delivery is practical and preferred.

In many embodiments, each volume is irradiated with each pulse to define a depth and cross-section size of the volume based on the tissue's OPD, the pulse duration and the cross-section beam size such that the volume is substantially stress confined and substantially thermally confined to eject the tissue via the mechanism of spinodal decomposition. The light energy can be transmitted through an optical fiber, and the light energy may comprise a wavelength from about 1.4 microns to 1.52 microns or from about 1.86 to about 2.5 microns to define the volume based substantially on water absorption.

Representative durations of each pulse can be within a range from about 100 picoseconds to about 1 micro second. More typical pulse durations of each pulse can be within a range from about 500 picoseconds to about 200 nanoseconds.

In many embodiments, the volume ablated with each pulse is within a range from about $1 \times 10^{-8}$ cm$^3$ to about $1 \times 10^{-5}$ cm$^3$. In alternative embodiments the volume ablated with each pulse can be within a range from about $1 \times 10^{-7}$ cm$^3$ to about $1 \times 10^{-6}$ cm$^3$.

In many embodiments, the volume corresponds to a depth and a width ejected with each pulse and a ratio of the depth to the width is within a range from about 2:1 to 1:6. The volume may correspond to a depth and a width ejected with each pulse and a ratio of the depth to the width can be within a range from about 2:1 to about 1:4, as in the case of 1940 nm wavelength in tissue having water as a primary chromophore delivered via fibers having core diameters of 50 to 200 um in contact with, or nearly so, the target tissue.

In many embodiments, the amount of energy of each pulse is within a range from about 100 micro Joules to about 100 milliJoules. In alternative embodiments the amount of energy of each pulse can be within a range from about 500 micro Joules to about 30 milliJoules. In additional embodiments the amount of energy of each pulse can be within a range from about 1 milliJoule to about 10 milliJoules.

In many embodiments, the tissue comprises collagen and wherein the collagen may reach or exceed the liquefaction threshold with each pulse of the light energy.

In many embodiments, the tissue comprises one or more of vascular soft tissue, cartilage or bone.

In many embodiments, an elongated incision having a length and a depth is formed in the tissue with the light energy, and the length and the width correspond to an area of the incision into the tissue and wherein tissue removal rate is at least about $10^{-8}$ cm$^3$/pulse up to $10^{-4}$ cm$^3$/pulse. Pulse repetition rates from single shot to 2000 Hz are representative. For fine or microscopic cutting, repetition rates less than 100 Hz may be used, including single pulse triggering to cause pulse by pulse operation.

In many embodiments, the light energy is transmitted through at least one optical fiber with an energy transmission efficiency of at least about 80%.

In another aspect, embodiments provide an apparatus to treat tissue. A laser generates a pulsed beam of light energy comprising a plurality of light energy pulses. Each pulse irradiates a volume of tissue and has a duration and an amount of energy so as to substantially inhibit stress and thermal energy propagation from the volume such that the volume of the tissue is ejected via the mechanism of spinodal decomposition. A controller is coupled to the laser to generate the pulsed light beam in response to commands from the controller.

In many embodiments, at least one optical fiber is coupled to the laser, and the plurality of pulses of the pulsed beam transmitted through the fiber to the tissue such that each pulse transmitted through the fiber is capable of irradiating a volume of tissue and has a duration and an amount of energy so as to substantially inhibit stress and thermal energy propagation from the volume such that the volume of the tissue is ejected via the mechanism of spinodal decomposition.

Flash vaporization is a unique and clinically important new capability. As described herein different target tissue may have different mechanical properties, requiring different amounts of threshold and/or optimal pressure to be generated within the treatment volume to eject substantially all of the material. It is desirable to provide surgeons with a cutting system that enables flash vaporization with efficient tissue ejection across a variety of tissue types. The versatility to cut a diverse variety of tissue types without substantially any thermal or mechanical damage to the tissue adjacent to the target volume enables surgeons provide better outcomes, less risk and shorter recovery periods for their patients.

Although specific reference is made to flash tissue vaporization, the flash vaporization as described herein can be used to flash vaporize many types of material, such as non-tissue material comprising water, for example.

A process is described including selecting a pressure to match tissue types; and adjusting the pressure to at least eject substantially all the target volume, wherein different tissue types have different threshold pressures. Also, a process is described including adjusting pressure with constrained ranges of wavelength, pulse duration, energy per pulse, and spot size parameters to at least achieve an ejection threshold for the target tissue.

Embodiments of the present invention provide improved methods and apparatus so as to provide versatile and effective tissue removal. A surgical laser system may comprise dynamic pulsing control of pulse width and intensity coupled to a user interface, such that the user can select a broad range of tissue treatment. For example, the system may allow a user such as a surgeon to select a target tissue response ranging from cold ablation, including flash vaporization, through to coagulation. The target tissue response may comprise a user selectable response desired by the surgeon based on visual feedback from a surgical image such as an endoscopic image. For example, the tissue response can range from cold ablation, including flash vaporization, without substantial coagulation to coagulation with minimal ablation. The cold ablation, including flash vaporization, may comprise cutting soft or hard tissue with short pulses having a duration of no more than about 500 ns, for example, such that the tissue may be cut without substantial thermal deposition and without substantial thermal damage to the underlying tissue of the ablation site. The laser beam may comprise a wavelength absorbed substantially with the tissue, for example such that a majority of the energy of the laser beam is absorbed within about 100 microns of tissue penetration. For example, the laser beam may comprise a wavelength within a range from about 1.8 to about 2.2 µm, such that the energy of the beam can substantially ablate the tissue with short pulses having a duration of no more than about 500 ns and such that the energy of the laser beam can induce thermal damage to the tissue with a continuous wave or repetitive pulses with a period less than about 2 ms. The thermal damage of the tissue may comprise substantial coagulation with a continuous wave or repetitive pulses with a period less than about 2 ms, for example, such that a substantial majority of the energy incident on the tissue results in thermal deposition and coagulation of the tissue with minimal tissue ablation. The user may select intermediate treatment modes where the corresponding tissue response is such that tissue is cut with moderate thermal deposition, for example. This substantial breadth of the targeted tissue response from cold ablation, including flash vaporization, to coagulation can be achieved, for example by dynamically varying the pump source and q-switch pulse parameters. The pump source and q-switch parameters can be varied independently, together, or combinations thereof, for a selected exposure setting. For example the pump source parameters of the laser gain medium and q-switch parameters can be varied together when the tissue is treated, so as to provide the wide range of user selectable treatment.

The system may comprise a small core waveguide, for example less than about 100 µm, so as to provide a very efficient cutting and coagulation, and to provide substantial accessibility to treatment sites with decreased invasiveness, for example endoscopic procedures to the sinus cavity accessed through a nose of the patient. The waveguide can be coupled to the laser such that the tissue at the treatment site is treated with the laser beam output in accordance with the targeted tissue response, for example one or more of cold ablation, including flash vaporization, ablation with coagulation, or coagulation without substantial ablation. As the user can change the targeted tissue response during treatment, for example in response to endoscopic images shown on a display, many surgeries can be performed with decreased invasiveness and improved results.

The user selectable cutting or coagulation of tissue can be achieved in many ways, for example, by pulsing the laser output beam in variable timing patterns and combinations. The pulses can be generated by pulsing the pump source, pulsing the laser beam with the q-switch, or pulsing both.

The laser system may include a pump source such as laser diodes coupled to a gain medium, a q-switch, mirrors sufficient to create a resonate cavity with the gain medium disposed therein, optics to focus the output laser beam into a delivery device such as a waveguide, a controller with a tangible medium, and an user interface. The waveguide may comprise an optical fiber coupled to the laser output so as to direct the laser output from the laser source to the treatment site. The system may further comprise an insertion device that at least one of houses or holds the waveguide for insertion of the waveguide into the body. The insertion device may be shaped to accommodate access and placement of the waveguide for performing specific surgical procedures, such as surgery of the sinus cavity.

Embodiments of the present invention provide improved methods and apparatus so as to provide versatile and effective tissue removal. The surgical laser system as described herein can be used with many surgical procedures and can be used to access many surgical locations of a patient, for example internal surgical locations. The surgical laser system has a user interface that allows the user to select a treatment based on a desired tissue response such as cold ablation, including flash vaporization, coagulation or ablation with intermediate levels of thermal damage. The laser system comprises circuitry coupled to the user interface and the laser, such that the circuitry can adjust the laser treatment parameters based on the tissue response identified by the user. The laser treatment parameters adjusted with the circuitry can include one or more of the pulse duration or exposure duration with continuous wave output, the output beam intensity, the intensity of the pumping of the gain medium, or pulsing of the gain medium, for example. The user can view an image of the tissue site, for example with an endoscope comprising viewing optics and the tissue treatment waveguide, and the user can select the desired tissue response based on the endoscopic images, such that the tissue can be cut with cold ablation, including flash vaporization, coagulated, or cut with a desired level of thermal damage as targeted by the user.

Although many of the figures as shown herein show laser beam pulse amplitudes with rectangles, based on the teachings described herein one of ordinary skill in the art will recognize that the pulsed laser beams of the embodiments described herein may comprise laser beam pulses having an output with a Lorentian or other distribution or profile over time such that the pulse duration may encompass a full width half maximum of the laser beam.

Figure 28A:
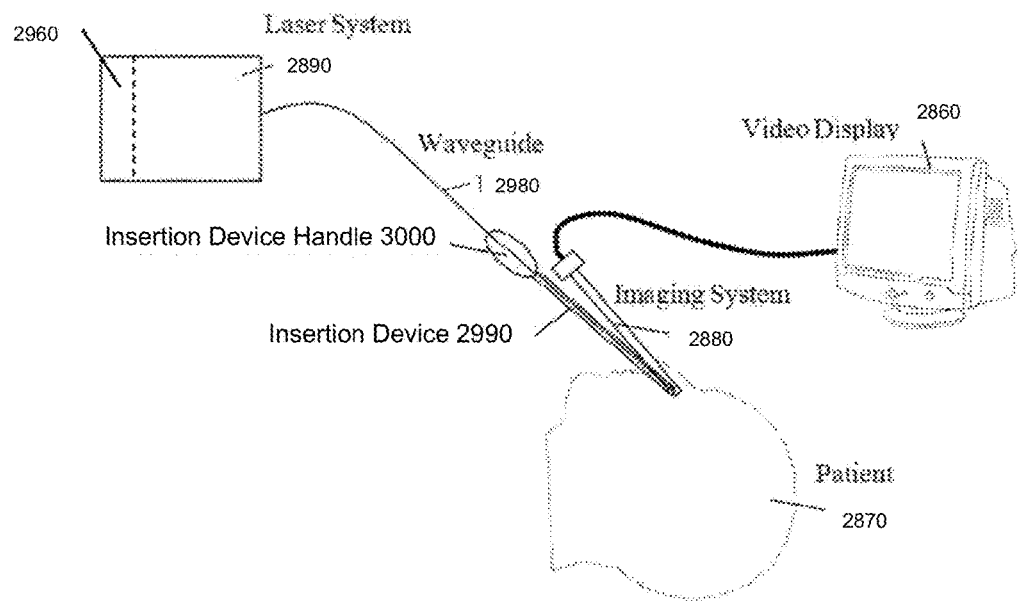
FIG. 28A shows a laser surgery system with an endoscopic probe inserted into a nasal cavity of a patient, according to embodiments of the present invention.

FIG. 28A shows the disclosed invention being used for sinus surgery. The patient 2870 has an imaging system 2880 inserted in a nostril. The imaging system 2880 may be a direct viewing type or it may have a camera with a video display 2860 such that the surgeon can view the inside of the sinus cavity. An insertion device 2990 with an insertion device handle 3000 and a waveguide 2980 is also inserted into the sinus cavity. The proximal end of the waveguide 2980 is attached to a laser system 2890 with an user interface 2960. The user can adjust the user interface setting to achieve the desired clinical effect. In one approach, flash vaporization as described above is utilized to remove tissue in the sinus cavity. The user interface 2960 also provides a means to activate the laser system to delivery energy to the treatment site via the waveguide 2980 and insertion device 2990.

Figure 28B:
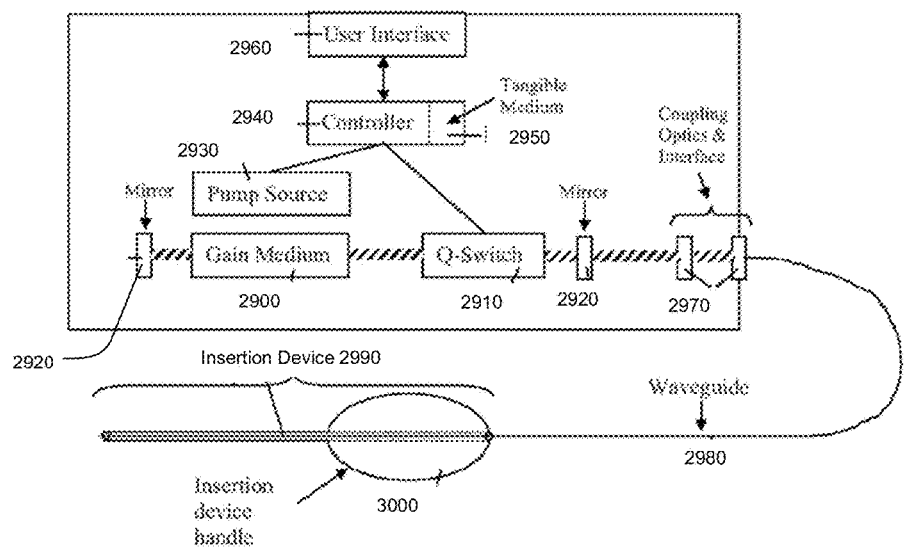
FIG. 28B shows the laser system of FIG. 28A for implementing a versatile and effective surgical tool with enhanced clinical capabilities, according to embodiments of the present invention.

FIG. 28B shows the laser system of FIG. 28A for implementing a versatile and effective surgical tool with enhanced clinical capabilities. The laser system has a gain medium 2900 and q-switch 2910 disposed between least two mirrors 2920 aligned to form a resonant cavity. A pump source 2930 provides energy to excite the gain medium 2900. A controller 2940 with a tangible medium 2950 may communicate or operate the pump source 2930 and the q-switch 2910. A user interface 2960 communicates with the controller 2940. The resulting laser energy passes through coupling optics 2970 to be coupled into a waveguide 2980. The waveguide 2980 passes through an insertion device 2990 used to insert the delivery system into a body. The insertion device may have a insertion device handle 3000 for the surgeon to hold and manipulate the insertion device 2990. In many embodiments, the laser system has a controllable pump source 2930 capable of generating a pulsed laser output beam. Some non-limiting examples of controllable pump sources include: flash lamp, arc lamp, hybrid lamp, diode laser, solid state laser, gas laser, dye laser, fiber laser and direct electrical stimulation. The pump source 2930 may in turn have a power source to operate it. The power source may be controllable to provide pulsed power to operate the pump source 2930 in a pulsed mode. Any means to control at least one of pulse amplitude, pulse duration or pulse period, preferably all three can be sufficient. Dynamic pulse control may be in the form of one set of pulse parameters, fixed during an exposure, for a given user setting and alternative sets of pulse parameters, fixed during the exposure, for different user settings. Additionally dynamic pulse control may be in the form of one or all pulse parameters changing during an exposure in a specified way for a given user setting, where each individual user setting may have different parameter changes during an exposure.

Figure 29A:
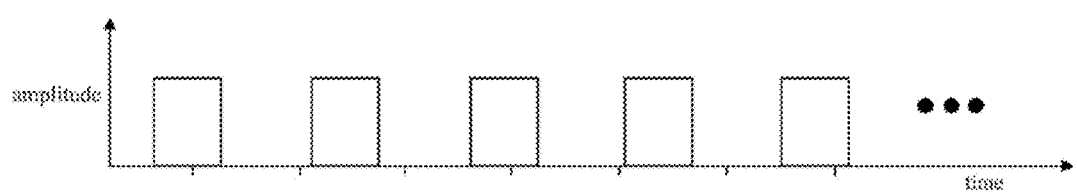
FIG. 29A shows an exemplary output waveform of the laser as in FIG. 28B when the system is operated in a pump pulse mode for thermal deposition to tissue.

FIG. 29A shows an example output waveform of the laser as in FIG. 28B with a series of laser beam pulses of substantially fixed pulse duration for thermal deposition to tissue with relatively less tissue cutting.

Figure 29B:
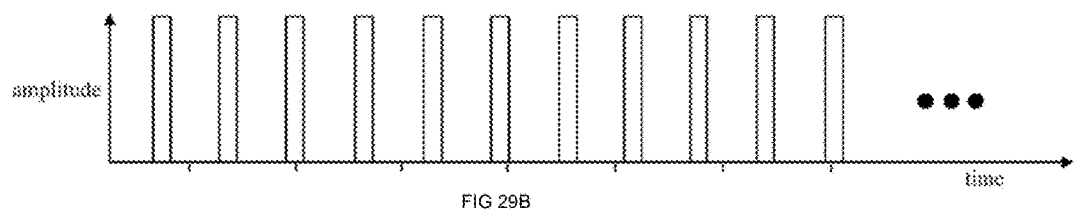
FIG. 29B shows an exemplary output waveform of the laser as in FIG. 28B when the system is operated in a pump pulse mode for cutting tissue.

FIG. 29B shows an example output waveform of the laser as in FIG. 28B with a series of laser beam pulses of fixed duration to cut while depositing less heat than the pulse series of FIG. 29A. The user may select between these two pulse structures, or many similar embodiments, depending on the surgical need. Some embodiments allow controlled variations of the pulse parameters for each individual pulse of a multi-pulse exposure. The pulse parameters may include: amplitude, duration and period.

Figure 30A:
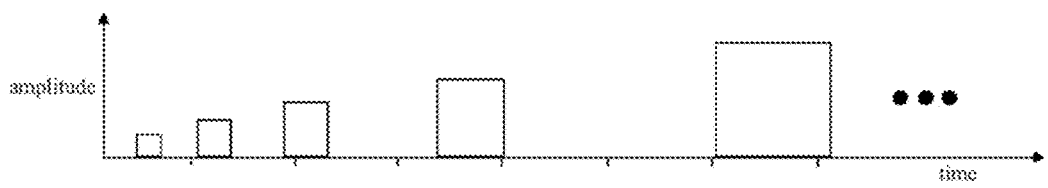
FIG. 30A shows an exemplary output waveform of the laser as in FIG. 28B when the system is operated in a pump pulse mode of linearly increasing pulse duration, period and amplitude.

FIG. 30A shows a non-limiting example output waveform of the laser as in FIG. 28B with a linearly increasing stair case pulse amplitude with an increasing pump period and increasing pump pulse duration. Alternatively this pulse structure could have a decreasing stair case or pulse period or pulse duration or inter-mixed combination of increasing, decreasing or static parameters. Also the rate of change from pulse to pulse could be non-linear for any one or up to all of these parameters.

Figure 30B:
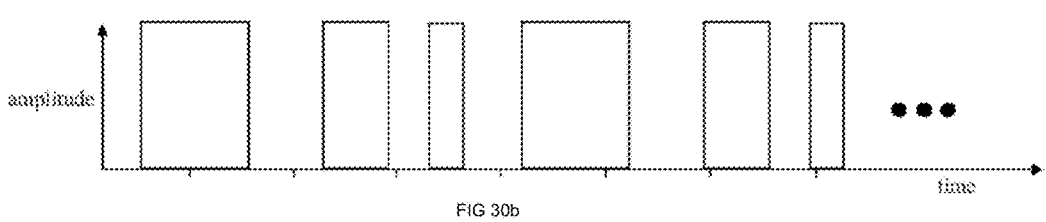
FIG. 30B shows an exemplary output waveform of the laser as in FIG. 28B when the system is operated in a periodic pump pulse mode of decreasing pulse duration and period.

FIG. 30b shows an example output waveform of the laser as in FIG. 28B with a decreasing pulse period and decreasing pulse duration in a periodic cycle. Alternatively the period or pulse duration may be increasing or combinations of increases and decreases. Also the pattern period could be shorter or longer with more or less substructure pulses. The amplitudes may be varied as well. Pulse control allows the tissue interaction to be customized to concurrently control the cutting rate and amount of thermal damage incurred on the remaining tissue. There are many pulse parameter permutations, both simple and complex that offer a clinical significance for surgery. Pulse control on an individual pulse basis during a multi-pulse exposure allows further refinement and control of cutting and coagulation.

Figure 30C:
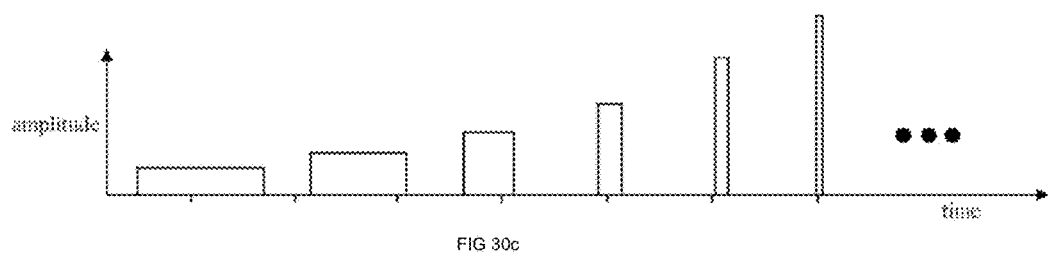
FIG. 30C shows an exemplary output waveform of the laser as in FIG. 28B when the system is operated in a pump pulse mode to maintain a relatively constant cutting rate with more coagulation at the beginning of the exposure.

FIG. 30C shows an exemplary output waveform of the laser as in FIG. 28B when the system is operated in a pump pulse mode to maintain a relatively constant cutting rate with more coagulation near the beginning of the exposure than the end of the exposure.

For example when a surgeon intends to maintain a relatively constant cutting rate but create deeper coagulation near the beginning of the exposure than the end, a non-linear decrease in pulse durations while increasing the amplitude during a multi-pulse exposure can begin with a greater deposition of heat into the tissue and then taper to less heat deposition, combined with a decrease in the period a steady cutting rate could be maintained, so as to provide enough heat to establish hemostasis and then proceed to cut without continuing to deposit excessive amounts a heat into the remaining tissue, as shown in FIG. 30C.

Figure 30D:
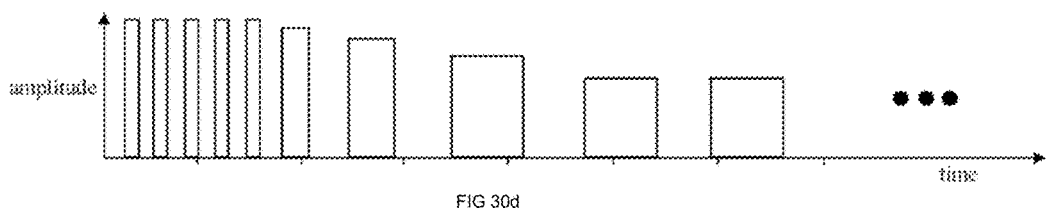
FIG. 30D shows an exemplary output waveform of the laser as in FIG. 28B when the system is operated in a pump pulse mode to create a relatively uniform coagulation zone around the contour of the cut region.

FIG. 30D shows an exemplary output waveform of the laser as in FIG. 28B when the system is operated in a pump pulse mode to create a relatively uniform coagulation zone around the contour of the cut region.

For example, when a surgeon intends to cut tissue while leaving a relatively uniform coagulation depth around the contour of the cut region. The initial pulses can be of shorter duration, higher amplitude and shorter period to induce flash vaporization or other cold ablation processes, and the pulse sequence transitions to longer pulse durations, lower amplitude, longer period pulses as shown in FIG. 30D.

Additionally examples may be periodic repetition of some designed pulsing pattern to accommodate longer cutting/coagulating cycles or more abrupt changes in pulse parameters such as combinations of short and long pulse durations with abrupt transitions to intermix cutting and coagulating within a multi-pulse exposure. Dynamic pulse variations allow control and customization of cutting and coagulation effects.

In many embodiments, the laser system has a controllable q-switch 2910 capable of generating a pulsed laser output beam. The q-switching can be achieved with acousto-optic, electro-optic, mechanical, saturable absorbers or other q-switching mechanisms. Most active q-switching mechanisms can have a power source to enable the q-switching action. The power source may be controllable to operate the q-switch 2910 in a pulsed mode or an off mode, enabling continuous wave operation. Any means to control at least one of the q-switch pulse amplitude, pulse duration or pulse period, preferably all three can be sufficient. Dynamic pulse control may be in the form of one set of pulse parameters, fixed during an exposure, for a given user setting and alternative sets of pulse parameters, fixed during the exposure, for different user settings. Additionally dynamic pulse control may be in the form of one or all pulse parameters changing during an exposure in a specified way for a given user setting, where each individual user setting may have different parameter changes during an exposure.

Figure 31A:
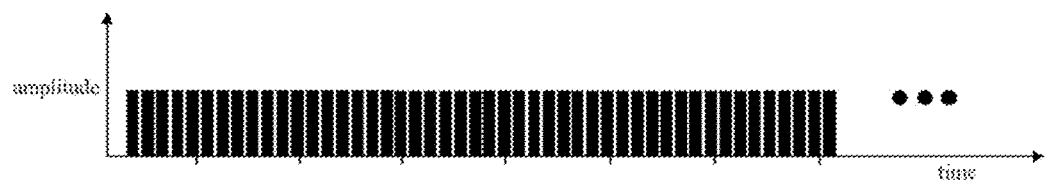
FIG. 31A shows an exemplary output waveform of the laser as in FIG. 28B when the system is operated in a q-switched pulse mode of less cutting efficient and more thermal deposition.

FIG. 31A shows an exemplary output waveform of the laser as in FIG. 28B when the system is operated in a q-switched pulse mode for thermal deposition and coagulation with relatively less tissue cutting.

Figure 31B:
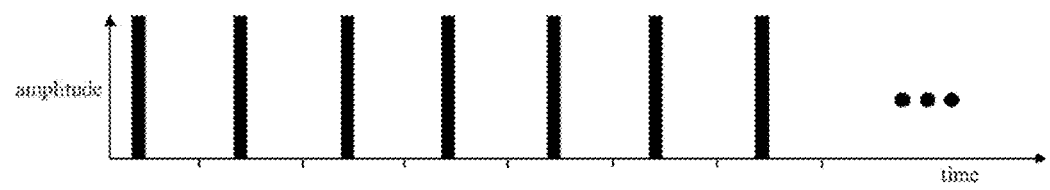
FIG. 31B shows an exemplary output waveform of the laser as in FIG. 28B when the system is operated in a q-switched pulse mode of more cutting efficient and less thermal deposition.

FIG. 31B shows an exemplary output waveform of the laser as in FIG. 28B when the system is operated in a q-switched pulse mode for efficient cutting of tissue and relatively less thermal deposition.

The user may select between these two pulse series of FIG. 31A or 31B, or many similar variations, depending on the surgical need. Embodiments allow controlled variations of the q-switch pulse parameters for each individual q-switch pulse of a multi-q-switch pulse exposure. The q-switch pulse parameters may include: amplitude, duration and period.

Figure 32A:
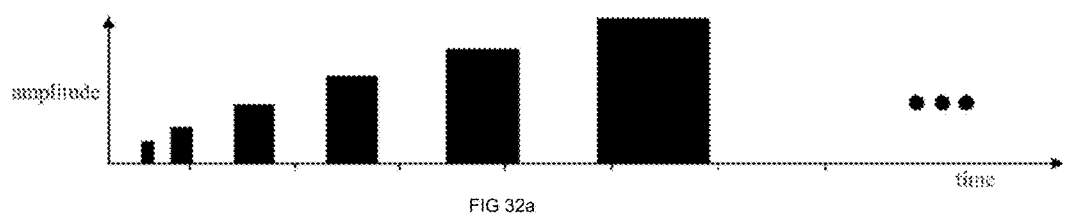
FIG. 32A shows an exemplary output waveform of the laser as in FIG. 28 B when the system is operated in a q-switched pulse mode of linearly increasing pulse duration, period and amplitude.

FIG. 32A shows a non-limiting example of an exemplary output waveform of the laser as in FIG. 28B when the system is operated in a q-switched pulse mode of linearly increasing pulse duration, period and amplitude. A linearly increasing stair case q-switch pulse amplitude with an increasing q-switch period and increasing q-switch pulse duration. Alternatively this q-switch pulse structure could have a decreasing stair case or pulse period or pulse duration or inter-mixed combination of increasing, decreasing or static parameters. Also the rate of change from pulse to pulse could be non-linear for any one or up to all of these parameters.

Figure 32B:
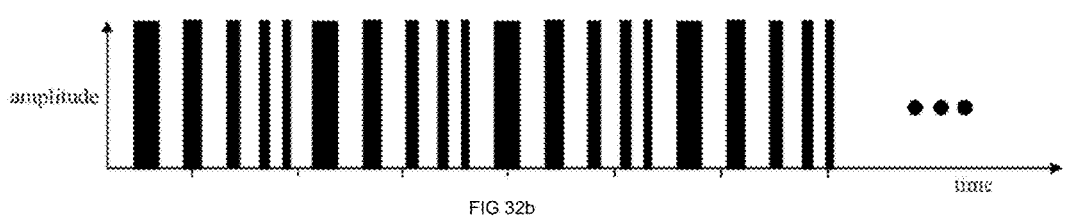
FIG. 32B shows an exemplary output waveform of the laser as in FIG. 28B when the system is operated in a periodic q-switched pulse mode of decreasing pulse duration and period.

FIG. 32B shows an example with a decreasing q-switch pulse period and decreasing pulse duration in a periodic cycle. Alternatively the period or pulse duration may be increasing or combinations of increases and decreases. Also the pattern period could be shorter or longer with more or less substructure pulses. The amplitudes may be varied as well. This dynamic q-switch pulse control additionally enables athermal or minimally thermal ablation of hard and soft tissue, including Flash Vaporization, and can allow transitions of these athermal or minimally thermal ablations to or from hotter ablations modes.

Figure 32C:
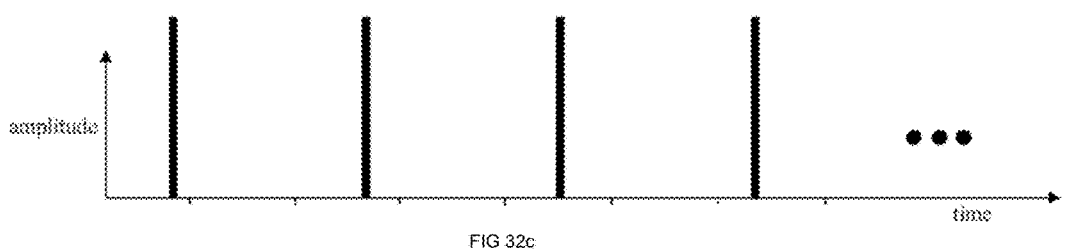
FIG. 32C shows an exemplary output waveform of the laser as in FIG. 28B when the system is operated in a q-switched pulse mode to ablate bone.

FIG. 32C shows an exemplary output waveform of the laser as in FIG. 28B when the system is operated in a q-switched pulse mode to ablate bone.

For example when a surgeon intends to excise a section of bone the system can be adjusted to longer period, higher amplitude q-switch pulses to enable cold ablation, including flash vaporization, of bone, as shown in FIG. 32C.

Figure 32D:
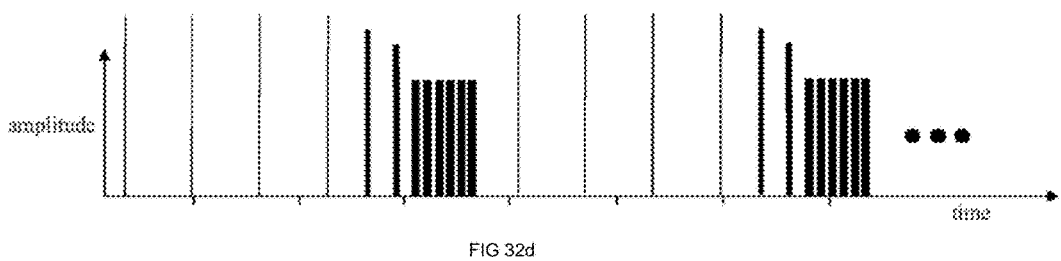
FIG. 32D shows an exemplary output waveform of the laser as in FIG. 28B when the system is operated in a q-switched pulse mode to cut tissue and deposit more heat to control bleeding.

FIG. 32D shows an exemplary output waveform of the laser as in FIG. 28B when the system is operated in a q-switched pulse mode to cut tissue and deposit more heat to control bleeding. When the surgeon then intends to remove highly vascular soft tissue adjacent to the bone the q-switch pulses can periodically repeat a pattern of long period, high amplitude, short q-switch pulses transitioning into shorter period, lower amplitude q-switch pulses, to enable efficient cutting while depositing more heat to control bleeding, as shown in FIG. 32D.

Figure 32E:
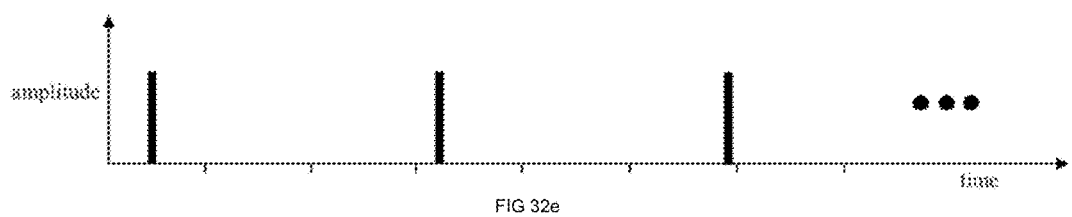
FIG. 32E shows an exemplary output waveform of the laser as in FIG. 28B when the system is operated in a q-switched pulse mode to remove a nerve sheath.

FIG. 32E shows an exemplary output waveform of the laser as in FIG. 28B when the system is operated in a q-switched pulse mode to remove a nerve sheath. When a surgeon intends to remove a nerve sheath the system could set to very long q-switch periods with lower amplitude pulses to carefully ablate the sheath with substantially no thermal deposition in the nerve itself, the controlled amplitude of the pulses help ensure just the sheath is ablated, as shown in FIG. 32E.

Figure 32F:
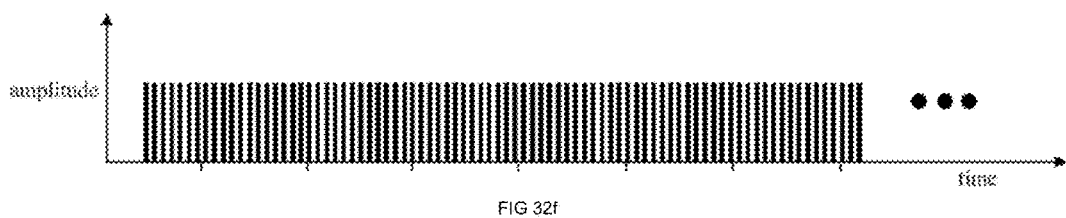
FIG. 32F shows an exemplary output waveform of the laser as in FIG. 28B when the system is operated in a q-switched pulse mode to coagulate a ruptured vessel.

FIG. 32F shows an exemplary output waveform of the laser as in FIG. 28B when the system is operated in a q-switched pulse mode to coagulate a ruptured vessel. When a surgeon intends to coagulate a ruptured vessel the system can be set to a short period q-switch pulse sequence, creating a quasi-cw mode, to increase thermal deposit and help coagulate the vessel, as shown in FIG. 32F.

Additional configurations may comprise periodic repetition of some designed q-switch pulsing pattern to accommodate longer cutting/coagulating cycles or more abrupt changes in q-switch pulse parameters such as combinations of short and long pulse durations with abrupt transitions to intermix cutting and coagulating within a multi-q-switch pulse exposure. This dynamic q-switch pulse control allows the tissue interaction to be finely customized to control the cutting rate and amount of thermal damage incurred on the remaining tissue.

Figure 33:
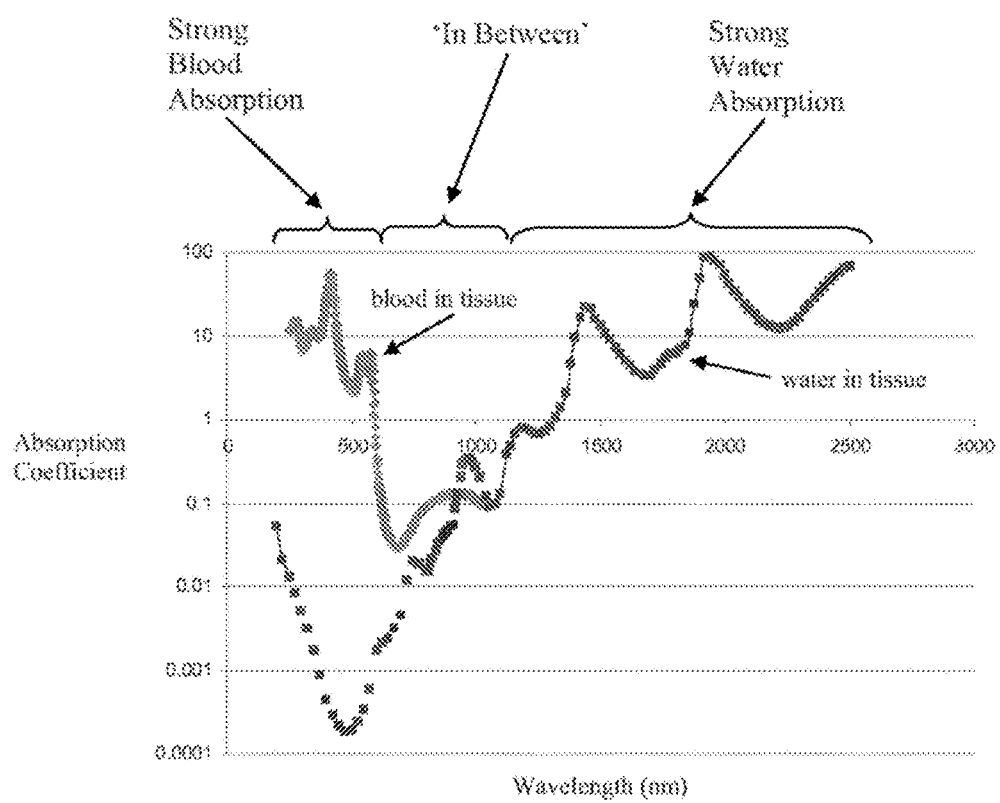
FIG. 33 shows the absorption characteristics of blood and water in tissue over a broad spectral range, for incorporation in accordance with embodiments of the present invention.

FIG. 33 shows the absorption characteristics of blood and water in tissue over a broad spectral range, for incorporation in accordance with embodiments of the present invention.

In many embodiments, the gain medium 2900 is relevant to the desired tissue effects and potentially relevant to the practical pulse parameters of the pump source 2930 and q-switch 2910. General types of gain mediums may include a solid state crystal, waveguide, polymer, gas, liquid or semi-conductor material. The gain medium 2900 can determine the allowable output wavelength or wavelength range. The wavelength can be relevant to surgical laser systems because the wavelength effects how strongly the light energy can be absorbed by tissue. Gain mediums and their respective output wavelengths can be grouped into three categories: strongly absorbed by water, strongly absorbed by blood and in between, where absorption in both blood and water is relatively weak, as shown in FIG. 33.

Most tissue, including bone, has a higher water content than blood content so wavelengths strongly absorbed by water tend to be more strongly absorbed in most tissue. One method of enabling a broad dynamic range of tissue effects is choosing a wavelength that is strongly absorbed in tissue, so that in combination with the appropriate pulsing parameters the system can achieve an efficient 'cold' cut whereby leaving, at most, only a shallow coagulation depth in the remaining tissue. Wavelengths strongly absorbed in blood and the 'in between' wavelengths can also be used to enable a broad dynamic range of tissue effects, but their ability to create a 'cold' cut is more challenging and typically has a more complex and expensive pulsing implementation. Wavelengths that are strongly absorbed in water are preferred. Certain gain mediums can lase efficiently across a broad range of wavelengths and can thus be tuned to a specific wavelength or wavelength band within its tunable range. Wavelength tuning can be fixed, user adjustable or variable during an exposure. Tuning may enhance the systems ability to achieve a desired clinical goal. Thulium types gain mediums like Tm:YAP, Tm:YAG, Tm:YLF, etc are typically strongly absorbed in water and can be readily transmitted down optical fibers. Tm:YAP has further advantages for surgical applications since it lases at 1.94 µm (a peak of water absorption) and a broad band of wavelengths above and below the water absorption peak. Tm:YAP also has an upper state lifetime of ~4 ms and therefore can be q-switched over a broad range of frequencies with high energy pulses. Laser systems designed with output wavelengths that are strongly absorbed by water may implement measures to prevent moisture from accumulating on the optical surfaces. Hermetic seal of the laser cavity, desiccants, inert gas purging and other techniques may be used to keep water from ultimately causing damage to the optical surfaces, including coatings. Similar measures may be used at the waveguide coupling interface.

In many embodiments the system may incorporate a small core flexible waveguide 2980. One advantage of a small and flexible waveguide 2980 is enhanced accessibility. Small waveguides can accommodate small endoscope working channels allowing smaller overall diameters of the endoscopes without compromising clinical functionality. Flexible waveguides accommodate flexible endoscope allowing access to areas where a straight line of access is difficult or impossible and the flexible scopes can do so without increasing the risk to the patient. For example access to the maxillary sinus cavity base through the natural opening of the nostril rather than a hole cut into the cheek or gums. Additional examples include natural orifice transluminal endoscopic surgery, where for example a gallbladder is treated via access into the mouth, down the esophagus, a through the stomach wall. An endoscope with limited flexibility can not be suitable to reach the gallbladder via that path. Additionally a flexible and small diameter endoscope can be more easily manipulated once the working tip is located at the treatment site, allowing surgeon to have better control to remove just the desired volume of tissue. Advances in small flexible scopes have enabled new and clinical beneficial ways to access target areas, although this equipment has been primarily for diagnostic purposes, in part, because no suitable surgical tools exist that can function well with the size, length and flexibility specifications to be compatible for performing treatments with these primarily diagnostic tools. An additional advantage of a small waveguide 2980 is that high irradiances or high fluences can be achieved with lower overall power or energy. For efficient ablation of hard or soft tissue some threshold energy for a given area should be exceeded. The steady state thermal ablation model is a well accepted approximation for both continuous wave and pulsed laser ablation.

Steady-State Ablation Model:

$$V_{ss}=E/p[c(T_b-T_o)+L_v]$$

$V_{SS}$ is the steady state ablation velocity (mm/s)
E is the irradiance (W/mm$^2$)
p is the density (g/mm$^3$)
c is the specific heat (J/g° C.)
$L_v$ is the latent heat of vaporization
$T_o$ is the initial temperature
$T_b$ is the boiling temperature of the irradiate tissue
A pulsed approximation for determining a vaporized volume of water is:

$$V_{ss}=A(Ho-H_{th})/W_{abl}$$

$V_{ss}$ is the volume of vaporized water (mm$^3$)
A is the incidence area (mm$^2$)
$H_o$ is the radiant exposure (J/mm$^2$)
$H_{th}$ is the threshold radiant exposure (J/mm$^2$)
$W_{abl}$ is the total heat of ablation (J/mm$^3$)
Alternative pulsed ablation model is the Blow Off model:

$$V_{bo}=(A/\mu_a)\ln(H_o/H_{th})$$

$Vb_o$ is the volume of vaporized water (mm$^3$)
A is the incidence area (mm$^2$)
$\mu_a$ is the absorption coefficient (1/mm)
$H_o$ is the radiant exposure (J/mm$^2$)
$H_{th}$ is the threshold radiant exposure (J/mm$^2$)
The energy needed goes down as the ablation area goes down, so smaller fibers with smaller tissue incidence surface areas can use less energy to ablate. As the total energy is reduced the ablated volume can be reduced as well, however when the goals is to excise tissue the ablated volume becomes less relevant than the surface area of the ablated volume to detach the tissue to be removed from the tissue that can remain. For example if the goal is to detach a polyp that has a 1 cm$^2$ attachment area to healthy tissue then it can removed by ablating a 2 mm wide section of the polyp base, resulting in a total ablation volume of 0.2 cm$^3$ or it can be removed by ablating a 100 um wide section of the polyp base, resulting in a total ablation volume of 0.001 cm$^3$. Both scenarios remove the polyp, the 100 µm section uses far less total energy to do so. The reduced power or energy that accompany a small treatment spot size allow the laser system to be scaled down in power and or energy output and thus in size and cost. This allows a very small, portable and efficient laser system to perform, at minimum, clinically equivalent to their larger, more expensive, more powerful counterparts. The reduction of overall system energy or power enables a physically small portable laser system to be battery operated and may be suitable for field use or where standard electrical utilities are not available. With the appropriate choice of wavelength, beam quality and pulse parameters the small low power system can outperform existing ablation technologies for tissue removal. Additionally, in-part, due to the small interaction area and proper parameter choices the collateral damage can be substantially non-existent. If some thermal damage is desired, for instance to control bleeding, then the system parameters can be adjusted such that some thermal damage occurs even with the small interaction area. High beam quality may enable the laser beam to be launched into a small core fiber optic waveguide 2980. The beam quality is both relative to the ability to focus down to a small enough spot to enter the waveguide 2980 and also to have a low enough numerical aperture to operate with minimal loss or damage when the fiber is bent during use.

Figure 34:
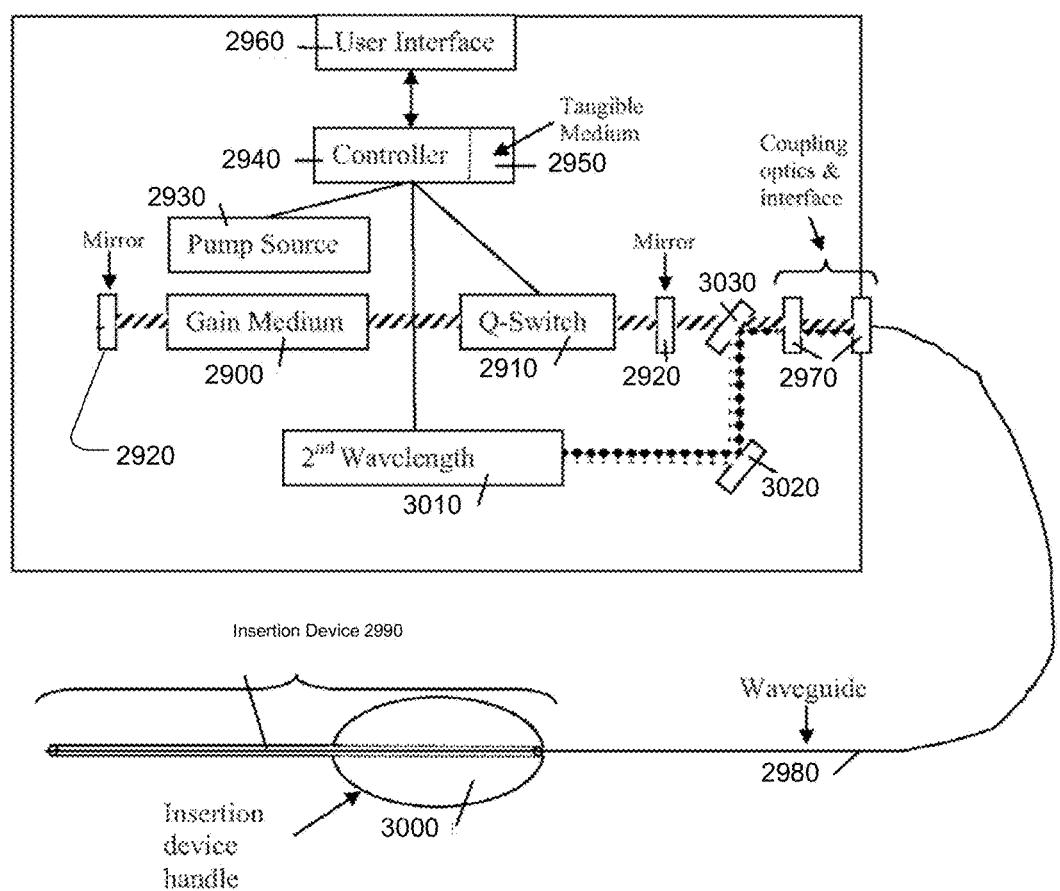
FIG. 34 shows a laser system with two complimentary output wavelengths for implementing a versatile and effective surgical tool with further enhanced clinical capabilities, in accordance with embodiments of the present invention.

FIG. 34 shows a laser system with two complimentary output wavelengths for implementing a versatile and effective surgical tool with further enhanced clinical capabilities, in accordance with embodiments of the present invention.

In many embodiments the laser system may have a second wavelength 3010. The second wavelength 3010 can be complimentary in some form, typically absorption characteristics or pulsing characteristics, to the primary wavelength. A second wavelength 3010 may broaden the systems scope of clinically meaningful tissue interactions, thus helping the surgeon achieve more optimal clinical results for their patients. The second wavelength 3010 may be independently controlled or intermixed with the primary wavelength. A routing mirror 3020 and a combining mirror 3030 may direct the second wavelength output beam to coincide with the primary wavelength beam to be coupled into the waveguide 2980. The second wavelength 3010 may include the pump pulsing, q-switch pulsing, gain medium, control system, delivery coupling, delivery system, beam quality and small waveguide features and functionality described herein, including all possible permutations, subsets and continuous wave operation.

In many embodiments the system may be used interstitially to coagulate, for example cook, ablate or a combination of coagulation and ablation to debulk a tissue mass while leaving the surface tissue substantially intact. For example, to reduce the mass of an inferior turbinate, while generally preserving the mucosa, a waveguide can be inserted interstitially into the submucosal tissue then the laser system can ablate by flash vaporization, a mass of tissue, including bone if desired, leaving an open cavity inside the sub-mucosal tissue.

Figure 35:
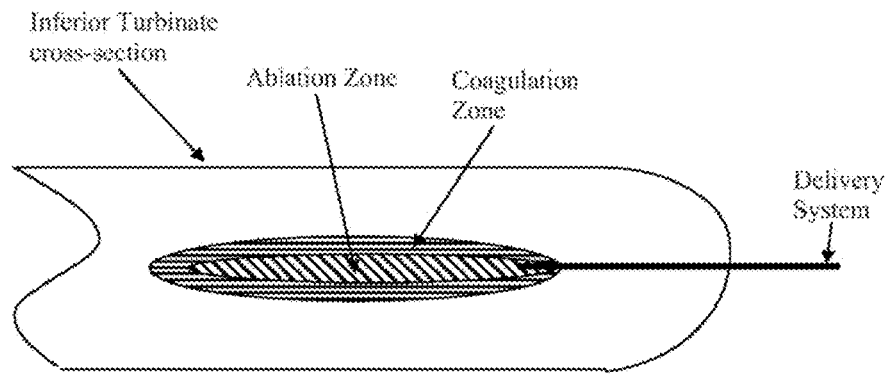
FIG. 35 shows a cross-section of an inferior turbinate, showing an exemplary tissue effect of the laser as in FIG. 28B or FIG. 34 laser system.

FIG. 35 shows a cross-section of an inferior turbinate, showing an exemplary tissue effect of the laser as in FIG. 28B or FIG. 34 laser system.

Alternatively or in combination, the system may ablate some mass of tissue and either concurrently, pre-ablation or post ablation coagulate a desired thickness of tissue around the surface of the sub-mucosal cavity, as shown in FIG. 35. Additional embodiments coagulate a mass of the sub-mucosal tissue with no substantial tissue ablation. These techniques may each remove tissue mass from the sub-mucosal and potentially bony regions and facilitate turbinate mass reduction and reduction of the overall size of the turbinate to reduce an airway obstruction. These interstitial techniques are applicable and effective for many other clinical applications as well.

Figure 36:
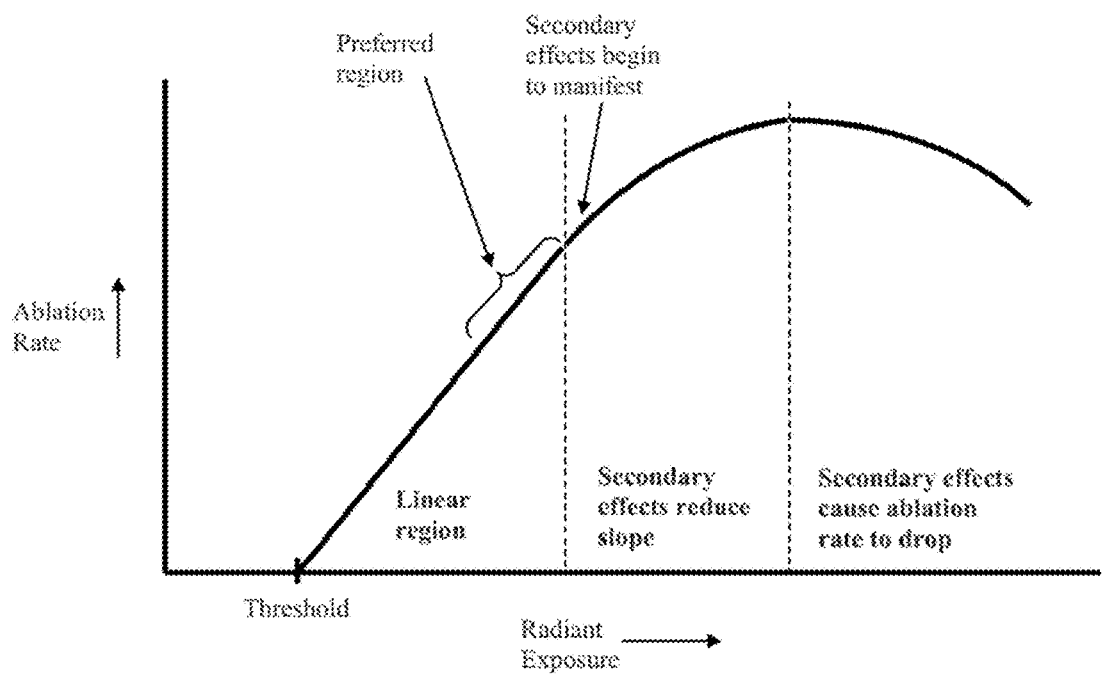
FIG. 36 shows a plot of ablation rate as a function of radiant exposure.

FIG. 36 shows a plot of ablation rate as a function of radiant exposure. In many embodiments the pulse parameters, gain medium and waveguide size are selected to optimize the ablation efficiency. The system setting may be chosen by the user to optimized ablation for different types of tissues. Once above the ablation threshold the ablation rate generally increases linearly as the radiant exposure increases. Then as the radiant exposure continues to increase secondary effects can start to occur that reduce ablation efficiency.

As radiant exposure is further increased the ablation rate can then begin to drop due to strong inefficiencies caused by the secondary effects, as in FIG. 36. Non-limiting examples of secondary effects may include incident beam scattering from ejected material, mechanical stress to the surrounding tissue or undesirable ablation crater shapes, for example crater shapes that diminish the efficiency of further ablation. At the onset of these types of secondary effects the ablation efficiency is still increasing with incident radiant exposure, although at a slower rate. Prior art systems are typically optimized for a maximum ablation rates which means they often operate in a regime where secondary effects play a role. For Flash Vaporization embodiments optimized ablation may be the fastest ablation rate that does not induce undesired secondary effects leading to undesired collateral damage of the tissue. Alternatively optimized ablation may be the highest positive rate of change in ablation speed. Clinically this is useful for ablation near or on sensitive tissue. For example nerve bundles where scattered light or mechanical shock waves may be damaging or painful.

Alternative and combinational embodiments include many permutations and subset permutations of the pump pulsing, q-switch pulsing, gain mediums, small waveguides, second wavelengths and operative techniques describe herein. These permutations provide powerful, effective, versatile and explicitly customizable performance characteristics to help surgeon remove any tissue with minimal collateral damage, optimal clinical outcomes, optimal recovery times, minimal risk and simple operative techniques. Dynamic pulse permutations may be in a form where the pump and q-switch pulse parameters are fixed during an exposure for a given user setting and alternative sets of pump and/or q-switch pulse parameters are fixed during an exposure for different user settings. Additionally dynamic pulse control may be in the form of one or all pump and/or q-switch pulse parameters changing during an exposure in a specified way for a given user setting, where each individual user setting may have different parameter changes during an exposure. A non-limiting example may be pulse structures where pump source pulse sequences with dynamic pulse durations, periods and/or amplitudes are comprised of q-switch pulse sequences with fixed or dynamic q-switch pulse durations, periods and/or amplitudes. A controller or some other means to coordinate the pulse timing between the pump source pulses and q-switch pulses may be used. In these embodiments one or more, up to all pump source and q-switch pulse parameters can be varied to operate in a fixed or dynamic multi-pulse exposure to optimize the desire clinical tissue effect.

FIG. 37A shows an exemplary output waveform of the laser as in FIG. 28B when the system is operated in a combined q-switched and pump pulse mode with fixed pump pulse parameters and a shorter q-switch period.

FIG. 37B shows an exemplary output waveform of the laser as in FIG. 28B when the system is operated in a combined q-switched and pump pulse mode with fixed pump pulse parameters and a longer q-switch period.

Some examples include a fixed pump pulse duration, period and amplitude with a fixed q-switch pulse duration, period and amplitude for one user setting and a second user setting with the same pump pulse scheme but a different q-switch period and amplitude, as in FIGS. 37A & 37B.

FIG. 37C shows an exemplary output waveform of the laser as in FIG. 28B when the system is operated in a combined q-switched and pump pulse mode with fixed q-switch pulse parameters and a longer pump pulse duration.

FIG. 37D shows an exemplary output waveform of the laser as in FIG. 28B when the system is operated in a combined q-switched and pump pulse mode with fixed q-switch pulse parameters and a shorter pump pulse duration.

Another embodiment comprises fixing of the q-switch pulse parameter and pump parameters for one user setting, but vary only the pump pulse duration and amplitude for a different user setting, as in FIGS. 37C & 37D.

Figure 37E:
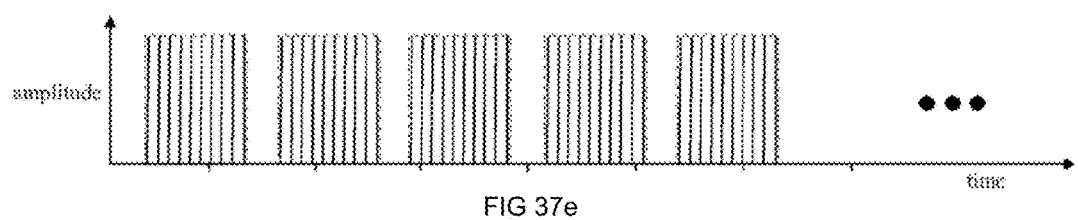
FIG. 37E shows an exemplary output waveform of the laser as in FIG. 28B when the system is operated in a combined q-switched and pump pulse mode with a longer pump pulse duration and a longer q-switch pulse period.

FIG. 37E shows an exemplary output waveform of the laser as in FIG. 28B when the system is operated in a combined q-switched and pump pulse mode with a longer pump pulse duration and a longer q-switch pulse period.

Figure 37F:
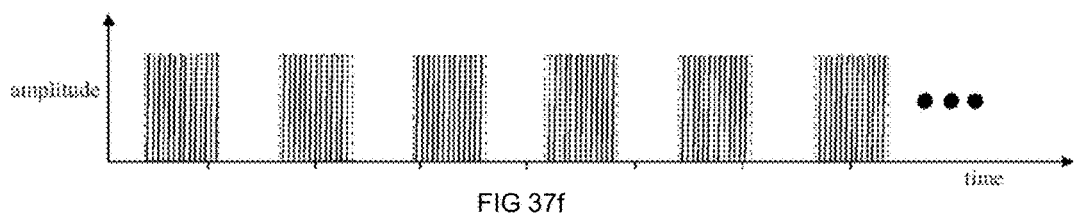
FIG. 37F shows an exemplary output waveform of the laser as in FIG. 28B when the system is operated in a combined q-switched and pump pulse mode with a shorter pump pulse duration and a shorter q-switch pulse period.

FIG. 37F shows an exemplary output waveform of the laser as in FIG. 28B when the system is operated in a combined q-switched and pump pulse mode with a shorter pump pulse duration and a shorter q-switch pulse period.

Another configuration comprises a fixed pump pulse duration, period and amplitude with a fixed q-switch pulse duration, period and amplitude for one user setting and a second user setting with a different pump pulse period, amplitude and a different q-switch period, as in FIGS. 37E & 37F.

Figure 38A:
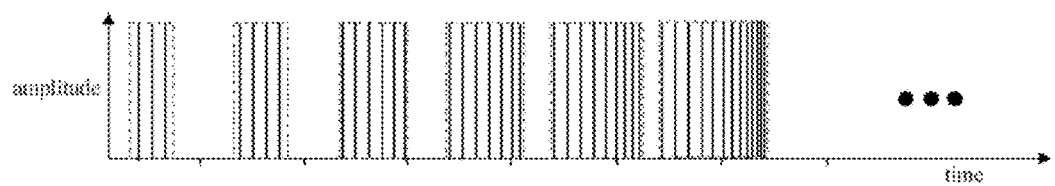
FIG. 38A shows an exemplary output waveform of the laser as in FIG. 28B when the system is operated in a combined q-switched and pump pulse mode with increasing pump pulse duration and decreasing q-switch pulse period within each pump pulse.

FIG. 38A shows an exemplary output waveform of the laser as in FIG. 28B when the system is operated in a combined q-switched and pump pulse mode with increasing pump pulse duration and decreasing q-switch pulse period within each pump pulse.

Figure 38B:
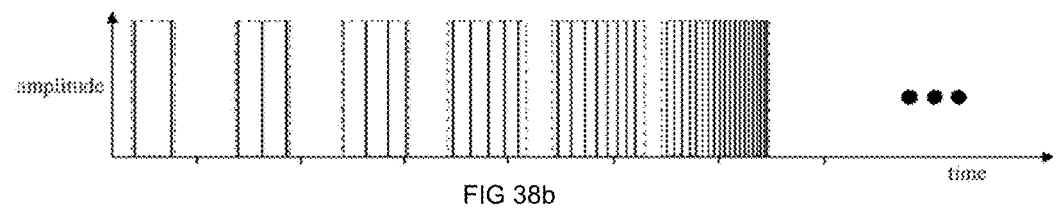
FIG. 38B shows an exemplary output waveform of the laser as in FIG. 28B when the system is operated in a combined q-switched and pump pulse mode increasing pump pulse duration and decreasing q-switch pulse period across a multiple pump pulse exposure.

FIG. 38B shows an exemplary output waveform of the laser as in FIG. 28B when the system is operated in a combined q-switched and pump pulse mode increasing pump pulse duration and decreasing q-switch pulse period across a multiple pump pulse exposure.

Additional embodiments include a linear step wise increase in pump pulse duration with a substructure of linear step wise decreasing period in the q-switch pulses, within each pump pulse or across the sequence of pump pulses, see FIGS. 38A and 38B.

Figure 38C:
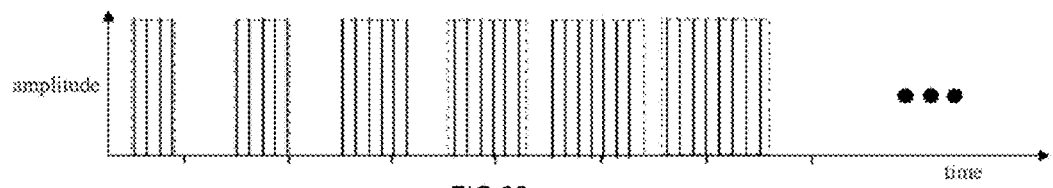
FIG. 38C shows an exemplary output waveform of the laser as in FIG. 28B when the system is operated in a combined q-switched and pump pulse mode with an increasing pump pulse duration and a fixed longer q-switch pulse period.

FIG. 38C shows an exemplary output waveform of the laser as in FIG. 28B when the system is operated in a combined q-switched and pump pulse mode with an increasing pump pulse duration and a fixed longer q-switch pulse period.

Figure 38D:
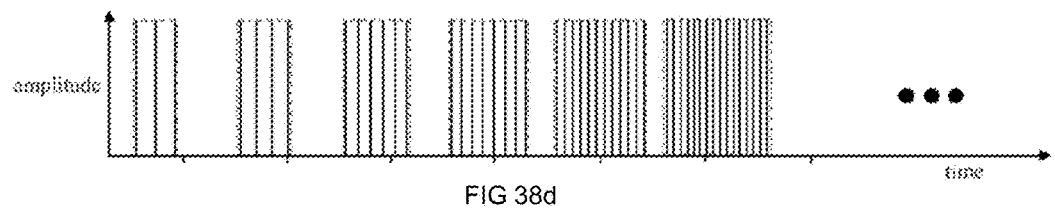
FIG. 38D shows an exemplary output waveform of the laser as in FIG. 28B when the system is operated in a combined q-switched and pump pulse mode with an increasing pump pulse duration and a q-switch pulse period that is fixed during each pump pulse and decreasing with each subsequent pump pulse.

FIG. 38D shows an exemplary output waveform of the laser as in FIG. 28B when the system is operated in a combined q-switched and pump pulse mode with an increasing pump pulse duration and a q-switch pulse period that is fixed during each pump pulse and decreasing with each subsequent pump pulse.

Alternatively with a linear step wise increase in pump pulse duration, each pump pulse may have a fixed q-switch pulse period within that individual pump pulse, as in FIG. 38D, and another embodiment comprises a fixed q-switch period within each individual pump pulse that can be decreasing with each subsequence pump pulse, as in FIG. 38D. These combinations can be advantageous for a surgeon who wants to begin with less thermal deposition and transition to more thermal deposition. Permutations of these with amplitude variations could also be employed to enhance the clinical effect.

Figure 39A:
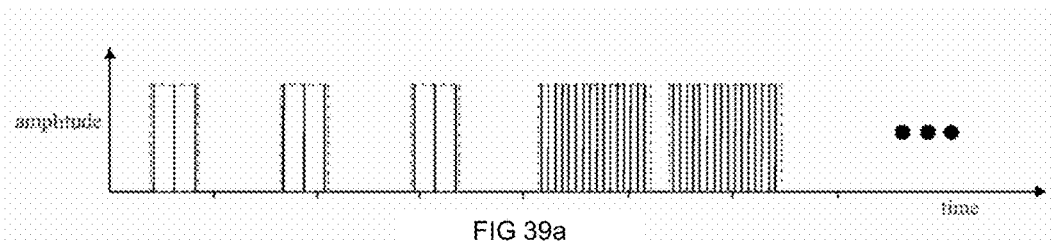
FIG. 39A shows an exemplary output waveform of the laser as in FIG. 28B when the system is operated in a combined q-switched and pump pulse mode with an abrupt transition from less thermal deposition to more thermal deposition.

FIG. 39A shows an exemplary output waveform of the laser as in FIG. 28B when the system is operated in a combined q-switched and pump pulse mode with an abrupt transition from less thermal deposition to more thermal deposition.

Additional examples of starting out with less thermal deposition and transitioning to more thermal deposition include some initial number of pump pulses with shorter pulse durations and longer q-switch periods and then an abrupt transition to longer pulse duration pump pulses with shorter period q-switch pulses, as in FIG. 39A. The q-switch pulse structure could be dynamically changed during these pump pulses as well.

Figure 39B:
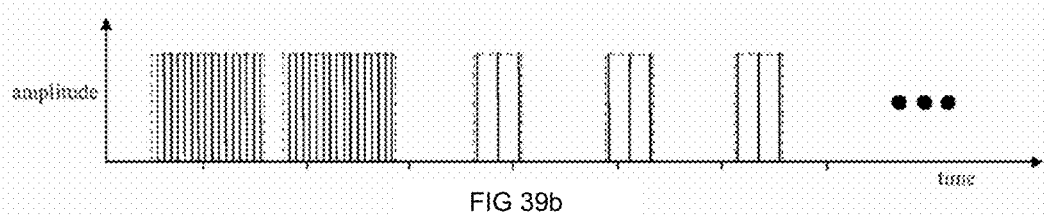
FIG. 39B shows an exemplary output waveform of the laser as in FIG. 28B when the system is operated in a combined q-switched and pump pulse mode with an abrupt transition from more thermal deposition to less thermal deposition.

FIG. 39B shows an exemplary output waveform of the laser as in FIG. 28B when the system is operated in a combined q-switched and pump pulse mode with an abrupt transition from more thermal deposition to less thermal deposition.

The opposite scenario where the initial pump and q-switch pulses combinations are such that they deposit more heat initially and the abruptly ablate may be advantageous for harder tissue where the surgeon would like to deposit substantial heat in the tissue and then use a strongly ablative pulse or pulse sequence to create a fracture, as in FIG. 39B.

Figure 39C:
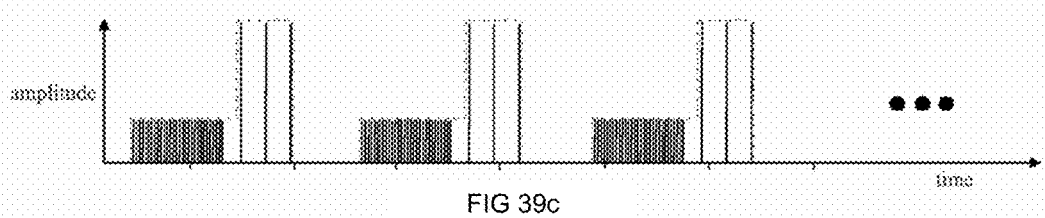
FIG. 39C shows an exemplary output waveform of the laser as in FIG. 28B when the system is operated in a combined q-switched and pump pulse mode with an abrupt transition from more thermal deposition to less thermal deposition, repeated during each pump pulse.

FIG. 39C shows an exemplary output waveform of the laser as in FIG. 28B when the system is operated in a combined q-switched and pump pulse mode with an abrupt transition from more thermal deposition to less thermal deposition, repeated during each pump pulse.

A hard tissue fracture effect may also be achieved by keeping the pump pulse parameters fixed and abruptly transitioning the q-switch pulse parameters from a low amplitude short period pulse structure to a high amplitude, high energy pulse structure abruptly near the end of each pump pulse, as in FIG. 39C.

Soft tissue resection with well controlled collateral damage zones may also be achieved with dynamic pump and q-switch pulse structures.

Figure 39D:
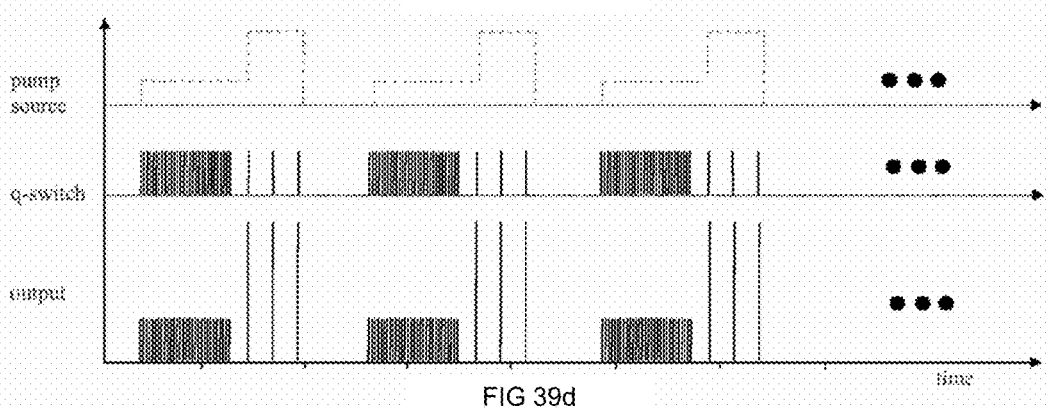
FIG. 39D shows the pump source and q-switch modulation individually and the resulting laser output waveform of the laser as in FIG. 28B when the system is operated in a combined q-switched and pump pulse mode with an abrupt transition from more thermal deposition to less thermal deposition, repeated during each pump pulse.

FIG. 39D shows the pump source and q-switch modulation individually and the resulting laser output waveform of the laser as in FIG. 28B when the system is operated in a combined q-switched and pump pulse mode with an abrupt transition from more thermal deposition to less thermal deposition, repeated during each pump pulse. The exemplary combination of pump pulsing and q-switch pulsing may comprise an abrupt transition from more thermal deposition to less thermal deposition, repeated during each pump pulse. The pump and q-switch pulses are shown individually with the resulting laser output shown at the bottom.

Figure 39E:
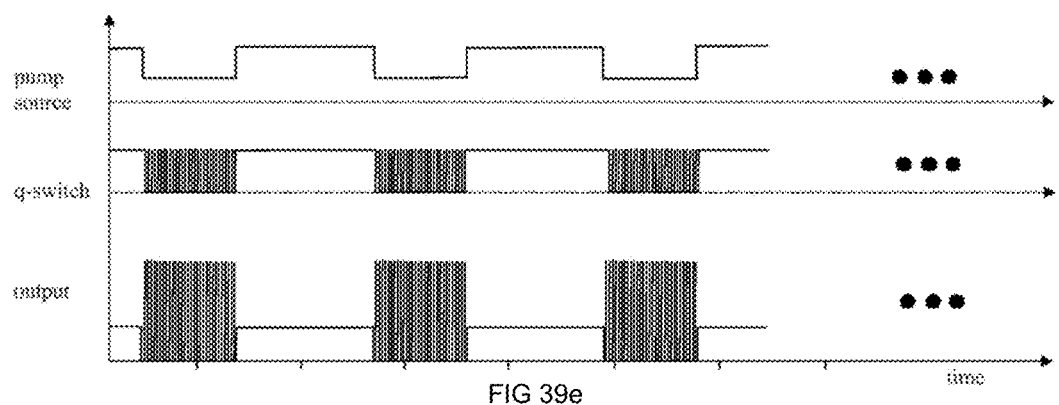
FIG. 39E shows an exemplary output waveform of the laser as in FIG. 28B when the system is operated in a combined q-switched and pump pulse mode with the q-switch mode including a continuous wave portion.

FIG. 39E shows an exemplary output waveform of the laser as in FIG. 28B when the system is operated in a combined q-switched and pump pulse mode with the q-switch mode including a continuous wave portion.

Alternative dynamic pulse structures may include continuous wave portions as part of the dynamic pulse structure. By operating the q-switch in the off mode with an appropriate range of pump source power, continuous wave operation can be achieved, as in FIG. 39E.

Figure 39F:
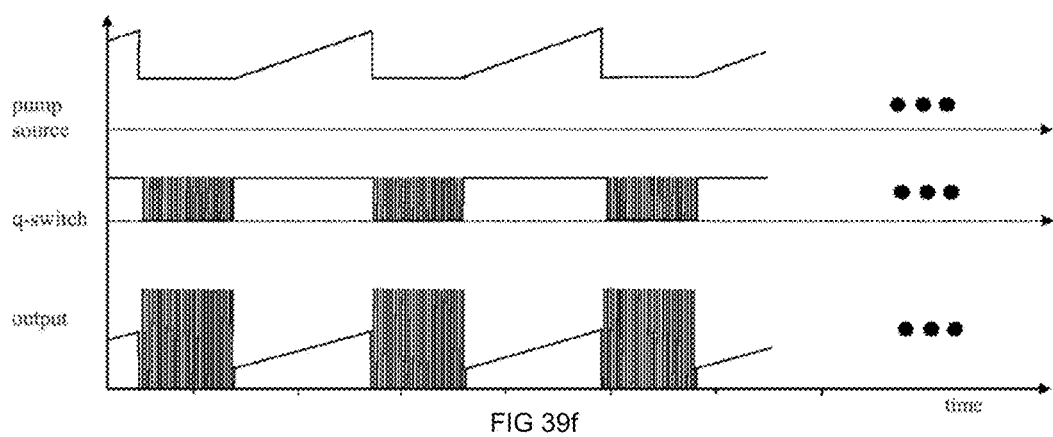
FIG. 39F shows an exemplary output waveform of the laser as in FIG. 28B when the system is operated in a combined q-switched and pump pulse mode with the q-switch mode including a variable amplitude continuous wave portion.

FIG. 39F shows an exemplary output waveform of the laser as in FIG. 28B when the system is operated in a combined q-switched and pump pulse mode with the q-switch mode including a variable amplitude continuous wave portion.

The pump and q-switch pulses are shown individually with the resulting output shown at the bottom. The continuous wave portion of a dynamic pulse scheme may also have variable amplitude, as in FIG. 39F.

Figure 40:
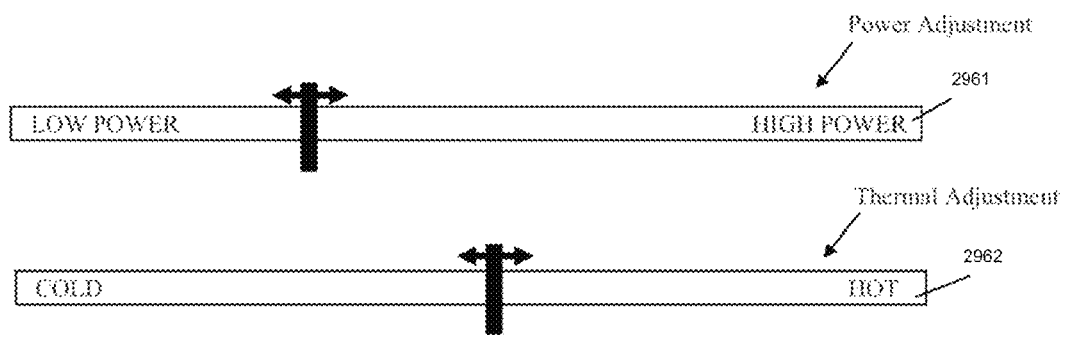
FIG. 40 shows an exemplary simple slide bar user interface with dynamic pulsing, in accordance with embodiments of the present invention.

FIG. 40 shows an exemplary simple slide bar user interface with dynamic pulsing, in accordance with embodiments of the present invention.

Dynamic pulsing of the pump source and/or the q-switch creates a wide array of pulse structure permutations that can be optimized for specific and finely controlled tissue interactions as well as span substantially all interaction types from cold ablation, including flash vaporization, continuously through to pure coagulation without ablation. Further embodiments include pulse combinations with small waveguides for improved cutting efficiencies and better accessibility. Additionally a complimentary second wavelength can be added to these permutations to broaden the span of achievable tissue interactions. Also the choice of gain medium 100 for these embodiments can influence the achievable tissue interactions.

The controller 2940 can be a centralized or distributed system that can control directly or indirectly the parameters of, at least, the pump source 2930 or q-switch 2910, preferably both. The controlled parameters may include pulse duration, pulse amplitude and pulse period. The controller 2940 may be capable of varying combinations of these pulse parameters down to an individual pulse basis. The controller 2940 may also operate the system in a non-pulsing mode for example continuous wave or quasi-continuous wave. The controller 2940 may include or communicate with directly or indirectly a means to tune the output wavelength. The controller may have a tangible medium 2950, for example known RAM, ROM and flash memory. The controller 2940 may include or communicate with the system's user interface 2960 allowing the user to select a setting that the controller 2940 may interpret and determine and implement the necessary pulsing scheme to achieve the desired tissue effect. The controller 2940 may include or communicate with the power source for the pump source 2930 and/or the q-switch 2910. An exemplary and relatively simple user interface for dynamic pulsing is shown in FIG. 40. The power adjustment 2961, which can be related to the cutting rate, may be a knob, slide, button, touch screen or other meaningful interface mechanism allows the user to select a power setting. A thermal adjustment 2962 mechanism which may also be a knob, slide, button, touch screen or other meaningful interface mechanism would control the level of thermal deposition into the tissue for the given power setting ranging from 'cold', substantially all ablative with little to no residual thermal damage, to 'hot', substantially all thermal deposition with little to no ablation.

Figure 41:
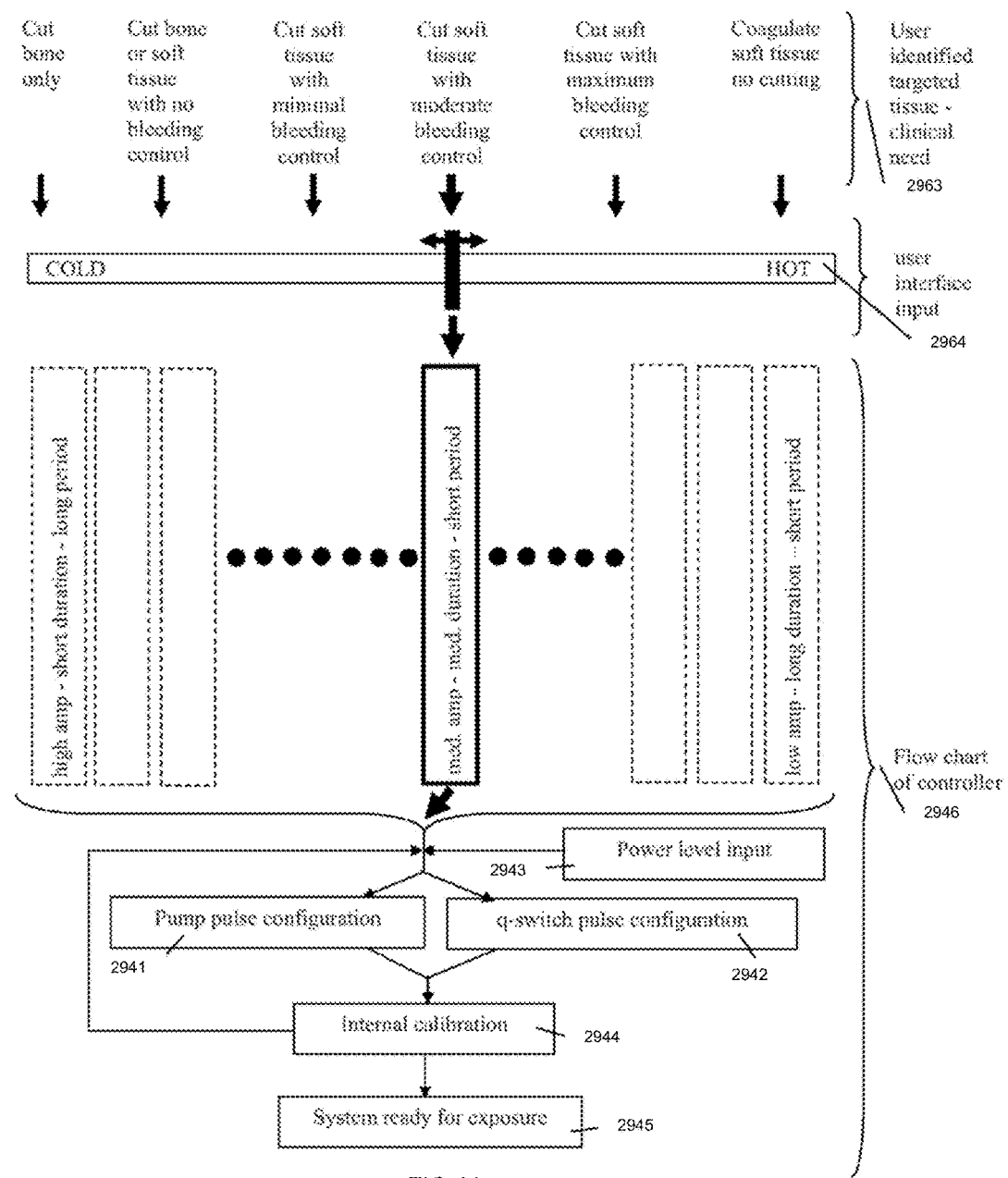
FIG. 41 shows an exemplary flow diagram for interpreting the user settings and establishing the laser output pulsing scheme, in accordance with embodiments of the present invention.

FIG. 41 shows an exemplary flow diagram for interpreting the user settings and establishing the laser output pulsing scheme, in accordance with embodiments of the present invention.

The surgeon may determine the appropriate settings based on the clinical need 2963, see the flow diagram FIG. 41. Once the setting are made the controller 2940 can prepare the pump pulse configuration 2941, which may include the amplitude, period and pulse duration settings as well as the q-switch pulse configuration 2942, which may include the amplitude, duration and period settings. In this example the internal dynamic pulse parameter settings are within predetermined ranges for specific user interface input 2964. Those predetermined ranges may be maintained in a portion of the controller tangible medium 2950. In FIG. 41 the user wants to cut soft tissue and maintain moderate bleeding control, such as removing a polyp attached to highly vascular tissue. The user input slide bar has been moved to the appropriate location. Now based on the slide position the controller 2940 correlates to a predetermined set of parameters, see the flow chart of controller 2946, in this case a medium amplitude, medium duration and short period pulse mode. For any inter-related parameter dependencies, for example q-switch pulse amplitude and q-switch period, the controller would determine the range limits and/or the mix of settings to achieve the desired outcomes as selected by the user. The dynamic predetermined settings may be adjusted during an internal calibration 2944 cycle to fine tune the parameters and accommodate the user power setting. When calibration is complete the system is ready for an exposure 2945. The controller 2940 can coordinate the timing of the dynamic pulse sequences during an exposure. Many alternative user interface 2960 and control structures can be used.

Figure 42:
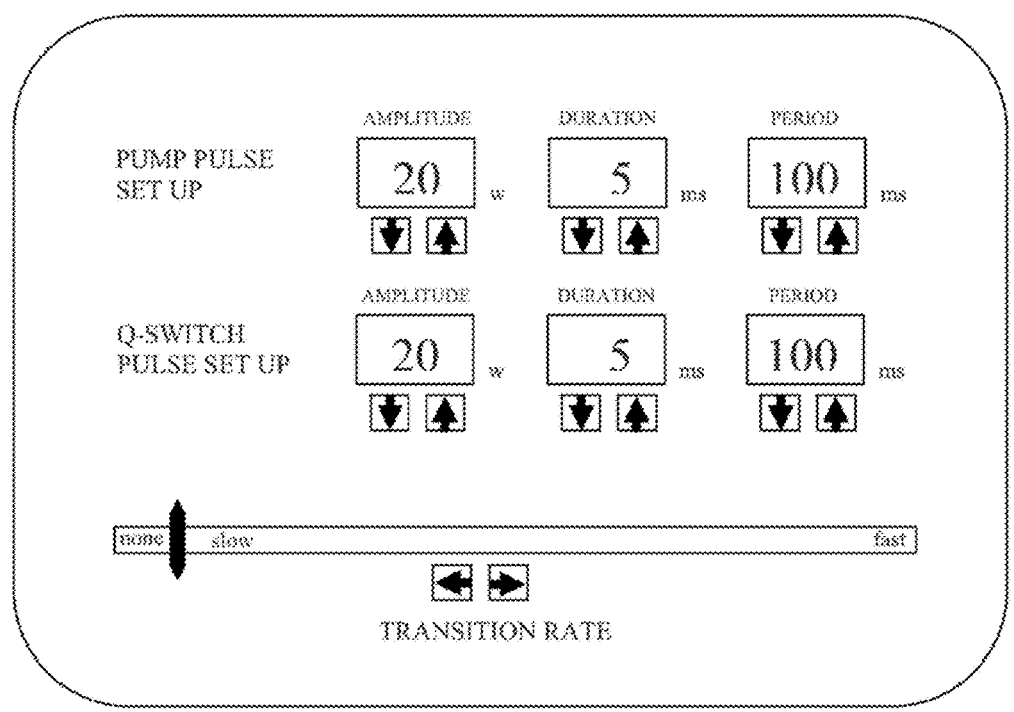
FIG. 42 shows an exemplary touch screen user interface for customizing dynamic pulse parameters without transitions during exposures, in accordance with embodiments of the present invention.

FIG. 42 shows an exemplary touch screen user interface for customizing dynamic pulse parameters without transitions during exposures, in accordance with embodiments of the present invention. In this example the dynamic pulse structure can be custom designed by the surgeon. The user can press the arrows on the screen to increase or decrease the adjacent parameter. For example the user may be able to select each pulse parameter: amplitude, duration and period for both the pump pulses and the q-switch pulses. In this example the 'TRANSITION RATE' adjustment is set to 'none' so the user selected parameters remain fixed during the exposure.

Figure 43:
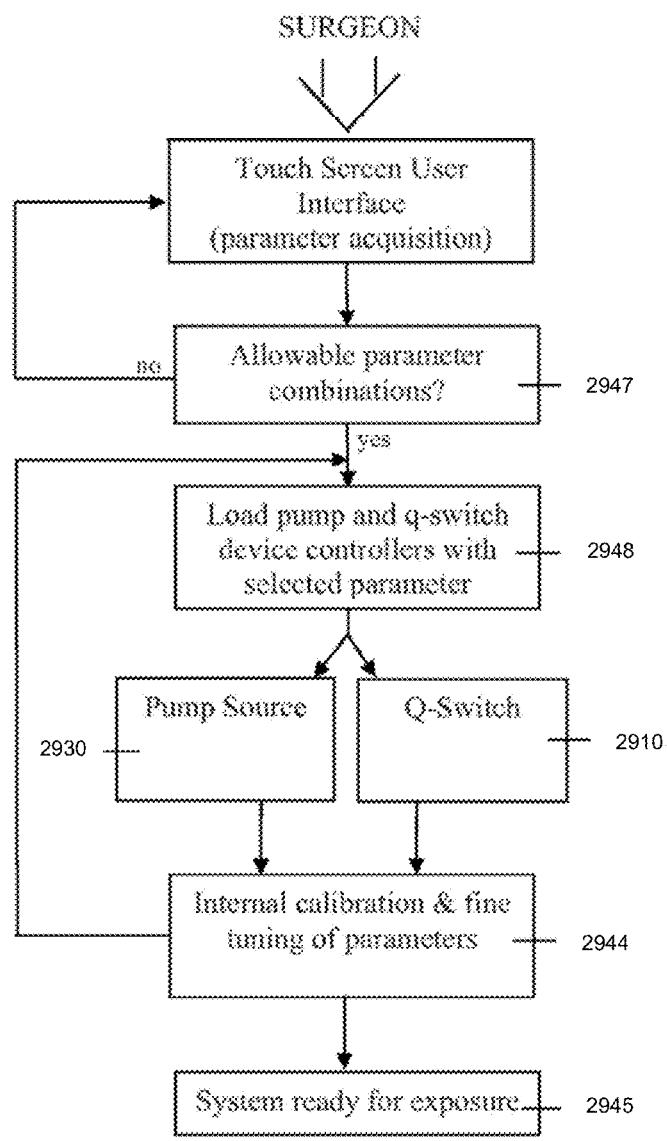
FIG. 43 shows a flow diagram of an exemplary control system for dynamic pulsing with an user interface as depicted in FIG. 42, including an exemplary flow diagram for interpreting the user settings and establishing the dynamic pulsing scheme without transitions during exposures, in accordance with embodiments of the present invention.
Figure 44:
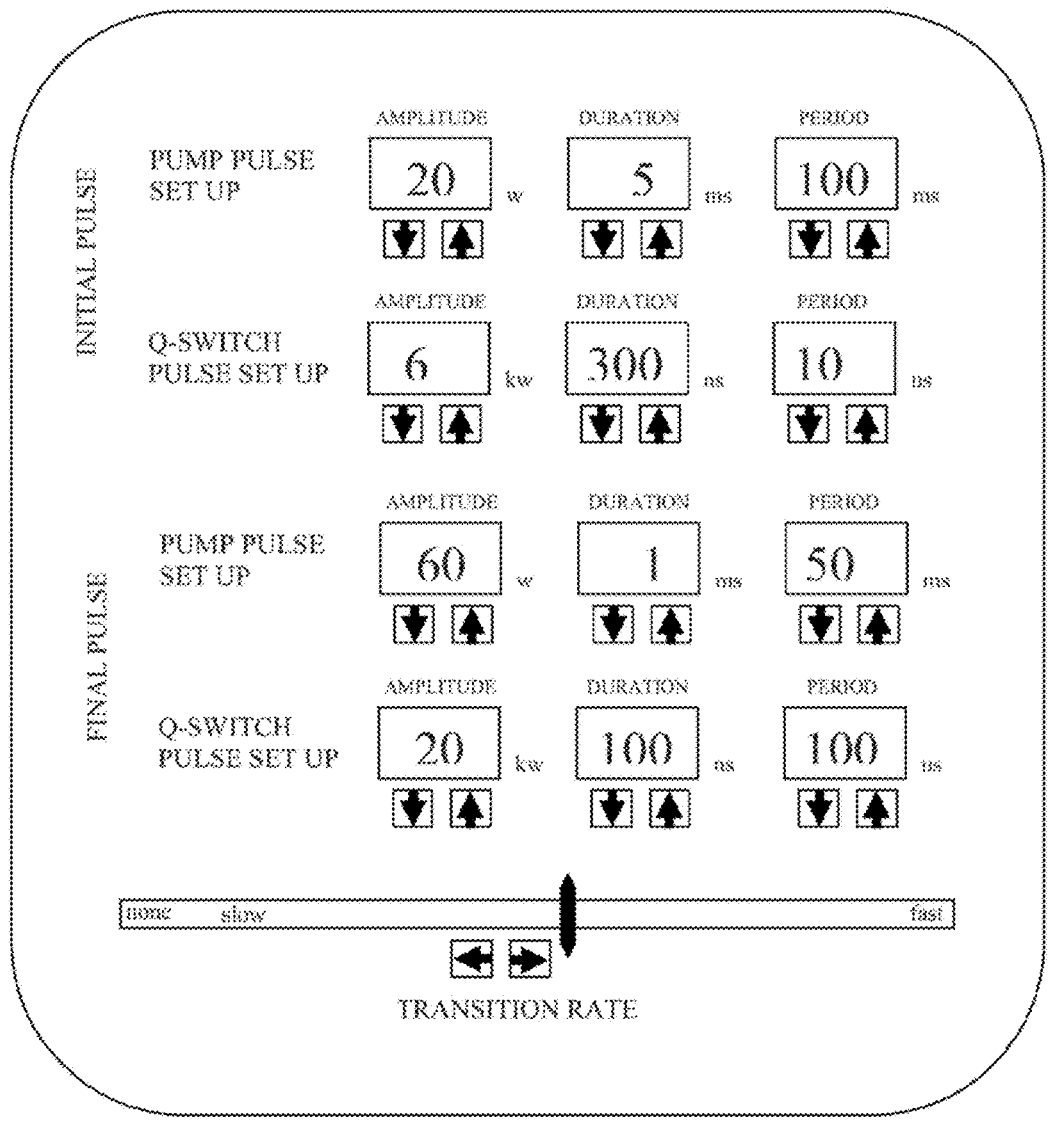
FIG. 44 shows an exemplary touch screen user interface for customizing dynamic pulse parameters with transitions during the exposure, in accordance with embodiments of the present invention.

FIG. 43 shows a flow chart for an exemplary control system for dynamic pulsing with an user interface as depicted in FIG. 42. The controller 2940 can limit the range of parameters selections to achievable settings, allowable parameter combinations 2947, and manage the hierarchy of priority when selections are made. The system can then load pump and q-switch device controllers with selected parameters 2948. An internal calibration 2944 is performed, if necessary some fine tuning of the parameters is performed to optimize the system and then the system is ready for exposure 2945. The controller can coordinate the timing of the dynamic pulse sequences during an exposure. FIG. 44 shows an exemplary user interface with a customizable dynamic pulse scheme including pulse transitions during the exposure. The user can press the arrows on the screen to increase or decrease the adjacent parameter. For transitioning pulse sequences the initial pulse sequence parameters are entered. Additionally the final pulse sequence parameters are entered. The user selects a 'TRANSITION RATE" varying from slow gradual transitions to fast abrupt transitions, in the this example the transition rate is midway between fast and slow.

Figure 45:
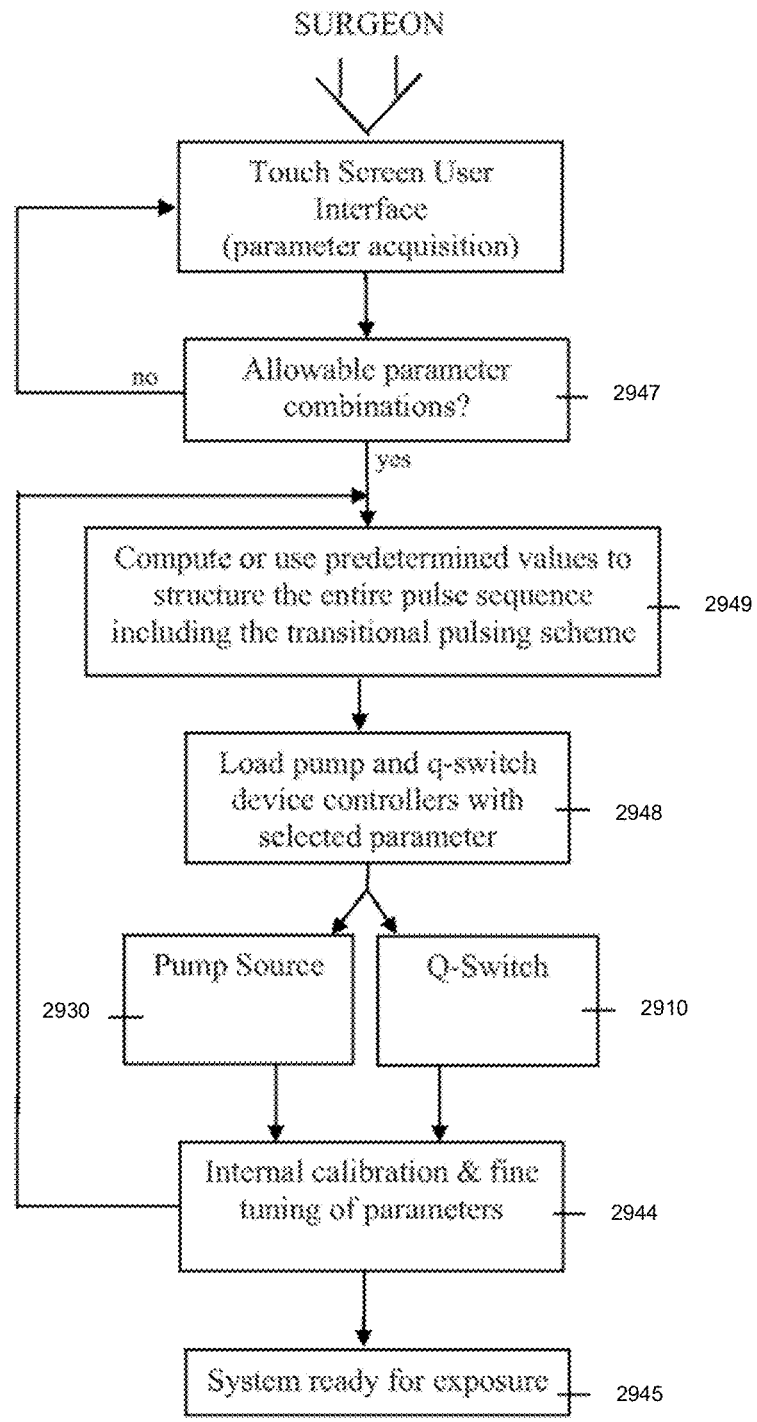
FIG. 45 shows a flow diagram of an exemplary control system for transitional dynamic pulses and an user interface as depicted in FIG. 44, including an exemplary flow diagram for interpreting the user settings and establishing the pulsing scheme with dynamic pulse transitions during an exposure, in accordance with embodiments of the present invention.

FIG. 45 shows a flow chart for an exemplary control system with transitional dynamic pulses with an user interface as depicted in FIG. 44. The controller 2940 can limit the range of parameters selections to achievable settings, allowable parameter combinations 2947, and manage the hierarchy of priority when selections are made. For transitional pulse settings the controller 2940 can compute or use predetermined values to structure the entire pulse sequences including the transitional pulsing scheme 2949. The system can then load pump and q-switch device controllers with selected parameters 2948. An internal calibration 2944 is performed, if necessary some fine tuning of the parameters is performed to optimize the system and then the system is ready for exposure 2945. The controller can coordinate the timing of the dynamic pulse sequences during an exposure. The controller may interface with an user activation switch to active the laser system. The user activation switch may be a hand or foot activated device and may include multiple functions.

Figure 46:
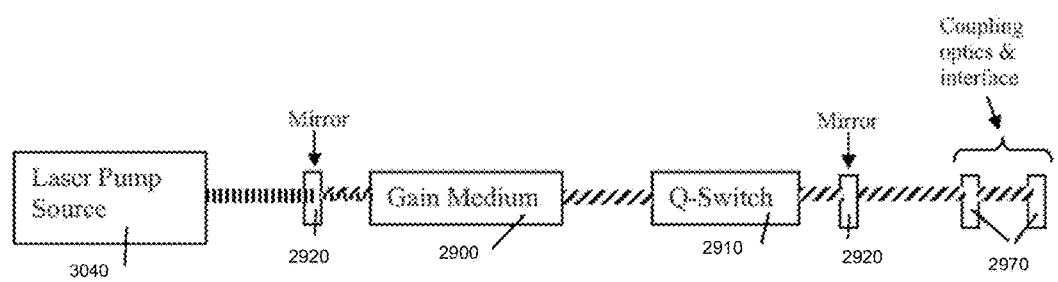
FIG. 46 shows a laser system using an end-pumping scheme to pump the gain medium, in accordance with embodiments of the present invention.

FIG. 46 shows a laser system using an end-pumping scheme to pump the gain medium, in accordance with embodiments of the present invention.

The resonator cavity may be formed with two mirrors 2920, one predominately reflecting the lasing wavelength and one partially transmissive to the laser output wavelength. The predominately reflective mirror may allow the pumping wavelength to pass through the mirror enabling the gain medium 2900 to be end pumped with a laser source 3040, for example diode laser. The intra-cavity elements are at minimum a gain medium 2900 and may include a q-switch 2910. Additional intra-cavity elements may include: lenses, substances for harmonic generation, elements to alter beam quality and various permutations of these elements. Cavities with more than two mirrors may also be used. A mirror may also be formed on the surface of an intra-cavity element rather than a stand alone element.

The coupling optics 2970 direct the laser output beam such that it can be coupled into a waveguide 2980 and ultimately directed to a treatment site. Single, multiple or lens-less configurations can be used as well as other techniques to direct beams.

The waveguide 2980 is preferably a low OH silica fiber capable of transmitting IR light up to 2.5 µm. The waveguide 2980 can be made from other transmissive materials with consideration of the specific wavelength and powers being transmitted. The waveguide 2980 may have a secure recognition device integrated such that the laser system can recognize when the waveguide is attached. The delivery system may include additional instrumentation to house or hold the waveguide for example to allow insertion of the waveguide endoscopically. The instrumentation may further facilitate manipulation of the waveguide 2980 and/or the waveguide tip to perform specific surgical functions. The instrumentation may also include suction, irrigation, visualization, tissue manipulation functionality or their permutations.

In many embodiments beam quality may be an important parameter. Beam quality relates to the clinical tissue effect by effecting beam divergence at the output of the delivery device tip, thus affecting the irradiance impinged on the tissue. Beam quality also affects the minimal core size and numerical aperture of a fiber optic deliver device, which affects the overall size and practical bend radius of the delivery fiber. End pumping is a preferred technique to help achieve good beam quality. Other techniques may include apertures, intra-cavity transmissive elements, thermal management of the gain medium and the general design of the resonant cavity.

Clinically significant wavelengths may span from 170 nm to 15 µm and may be fixed or tunable.

Clinically significant pump source pulse parameters may span the following ranges:
Peak pulse amplitude from 0.1 W to 10 KW
Energy per pulse from 10 uJ to 24 J
Pulse durations from 0.1 us to 10 s
Pulse periods from 1 us to 10 s
With a resultant average power from 1 mW to 1 KW Clinically significant Q-switch pulse parameters may span the following ranges:
Peak pulse amplitude from 1 W to 100 MW
Energy per pulse from 10 nJ to 1 J
Pulse durations from 1 ns to 100 us
Pulse periods from 10 ns to single shot
With a resultant average power from 1 mW to 1 KW Clinically significant combinations of pump pulsing and Q-switch pulsing may span the permutations for each individually as listed and additionally span a resultant average power range from 1 mW to 1 KW.

Clinically significant beam quality may range from: $M^2$ of 1 to 100

Treatment spot size range from: 10 µm to 10 mm

Clinically significant pump pulse working beam peak power per unit area may range from:
1 mW/cm$^2$ to 125 GW/cm$^2$ Clinically significant Q-switch pulse working beam peak power per unit area may range from:
1 W/cm$^2$ to 500 GW/cm$^2$ Clinically significant working beam average power per unit area may range from:
1 W/cm$^2$ to 125 GW/cm$^2$ Waveguide core sizes may range from 2 µm to 2 mm, preferably 25 µm to 100 µm.

Some non-limiting preferred parameters for a Tm:YAP gain medium:

Clinically significant wavelength may span from 1.8 µm to 2.2 µm and may be fixed or tunable.

Clinically significant pump source pulse parameters may span the following ranges:
Peak pulse amplitude from 0.5 W to 120 W
Energy per pulse from 0.1 mJ to 24 J
Pulse durations from 10 us to 2 s
Pulse periods from 1 ms to 2 s
With a resultant average power from 1 mW to 12 W Clinically significant Q-switch pulse parameters may span the following ranges: Peak pulse amplitude from 100 W to 50 MW
Energy per pulse from 1 mJ to 50 mJ
Pulse durations from 5 ns to 500 ns
Pulse periods from single shot to 100 us
With a resultant average power from 0.05 W to 12 W Clinically significant combinations of pump pulsing and Q-switch pulsing may span the permutations for each individually as lists and additionally span a resultant average power range from 0.1 W to 50 W.

Clinically significant beam quality may range from:
$M^2$ of 1 to 10

Clinically significant pump pulse working beam peak power per unit area may range from:
1 KW/cm$^2$ to 350 KW/cm$^2$ Clinically significant Q-switch pulse working beam peak power per unit area may range from:
1 KW/cm$^2$ to 750 GW/cm$^2$ Clinically significant working beam average power per unit area may range from:
0.5 W/cm$^2$ to 100 MW/cm$^2$ Substantially all tissue types are responsive across a broad range of tissue effects when utilizing dynamic pulsing, appropriate gain mediums, small waveguides, or their subsets or permutations, including but not limited to vascular tissues, avascular tissue, tumors, cysts, nerve, mucosa, submucosa, connective tissues, cartilage, organs and bone. The invention disclosed, in part, provides uniquely designed pulse structures that can sequence or blend the cutting and coagulative tissue effects in ways advantageous for the surgeon to achieve an optimal clinical result. One clinical benefit of dynamically adjusting the pulse parameters and their permutations is that a surgeon can determine the appropriate level of thermal deposition, across a broad range, to control bleeding during surgery while preserving the viability of the remaining tissue. Another clinical benefit is that dynamic pulse control enables the removal of both hard and soft tissue. Dynamic pulse control also improves visibility for the surgeon during the procedure by controlling bleeding, smoke or both. Dynamic pulsing additionally allows the trauma to the remaining tissue to be controlled and thus expedites the patient recovery time and can also reduce pain and suffering during the recovery period. Gain mediums producing wavelengths strongly absorbed by water are preferred, but not necessary. These wavelengths provide a cost effective means to produce a surgical laser system encompassing a broad range of tissue effects. A high beam quality laser system enabling the use of small core waveguides is also preferred. The small waveguides enable improved accessibility and provides efficient tissue removal with minimal power or energy. Small waveguides are well suited for minimally invasive procedures. Providing surgeons with a tool to remove all types of tissue safely and effectively is beneficial for substantially all types of surgical procedures. The system is well suited for endoscopic natural orifice procedures such as functional endoscopic sinus surgery, turbinate reductions, head and neck surgeries, colon, rectal, esophageal, bariatric, trans-vaginal, cystoscopic surgery and others. It is additionally well suited for laparoscopic surgeries such as appendectomies, hernia repair, bariatric, cholescystectomy, bowel resection, sterilization and others. Orthopedic, spine, neurologic, brain and traditional open surgeries can benefit as well. Future trends toward natural orifice transluminal endoscopic surgery can also benefit from a small flexible delivery system with broad and versatility selection of tissue effects.

EXAMPLES

A sinus surgeon performing an ethmoidectomy can remove the center portion of the thin bony honeycomb like structure and the surrounding mucosa of the ethmoid sinus cavity to improve mucus drainage. The surgeon may enter the ethmoid through a mucosa covered bony structure with minimal bleeding using a periodic pulse scheme such as shown in FIG. 32d. The FIG. 32d pulse scheme periodically blends ablative pulses for bone removal with some light heating pulses to control bleeding from small capillaries. Once inside the ethmoid sinus the surgeon may encounter more bony structures with very thin mucosa where the surgeon may not be concerned about bleeding issues. In this case the surgeon can switch setting to a pulse structure such as FIG. 32c where a cold ablation, including flash vaporization, of bone is performed with almost no coagulative heating. If at some point during the procedure an artery is perforated a setting such as FIG. 32f can be used to heat the localized area to control bleeding without ablating tissue.

For an inferior turbinate reduction the goal may be to reduce the turbinate's overall size to improve airflow while minimizing damage to the mucosal tissue layer. A submucosal approach can be used to maximize preservation of the mucosal layer. A small core fiber delivery device is beneficial in that it minimizes the size of the trauma area where the device is being inserting into the turbinate. During entry and just through the mucosal layer a pulsing scheme such as FIG. 39a may be used to ablate a small hole and deposit a little heat to prevent bleeding from small capillaries. Once the fiber is placed in the desired location submucosally, a pulse scheme such as FIG. 37d can be used to efficiently ablate a volume of submucosal tissue. Then a pulse scheme such as FIG. 37f can be used to slightly increase the ablation volume and to create a moderate coagulation zone that, in conjunction with the cavity that was initially created, can allow the overall turbinate size to be quickly reduced, improving airflow, preserving a maximal amount of mucosa and facilitating a rapid patient recovery period.

When removing a gallbladder using a natural orifice transluminal endoscopic technique it can be advantageous to have a very small diameter and flexible resection tool to accommodate the long catheter like instrumentation that is run down the esophagus, into the stomach and through the stomach wall to a location adjacent to the gallbladder. Once properly located it is also advantageous to be able to manipulate the position of the work tip. A small flexible fiber is well suited for this type of manipulation. When resecting the gallbladder a pulse scheme such as FIG. 38d would be advantageous to cut the gallbladder free while maintaining a moderate to thick coagulation zone to keep bleeding well under control.

For brain surgery a small insertion device 2990 may be advantageous to reach the volume to be removed with minimal impact to tissue in the access path. Resection can be performed with thin uniform coagulation control such as the pulse scheme shown in FIG. 30d to control bleeding. Then the partially separate mass to be removed can be ablated using a pulse scheme such as FIG. 32c. The ablated tissue remains could be removed via a small suction path.

Figure 47:
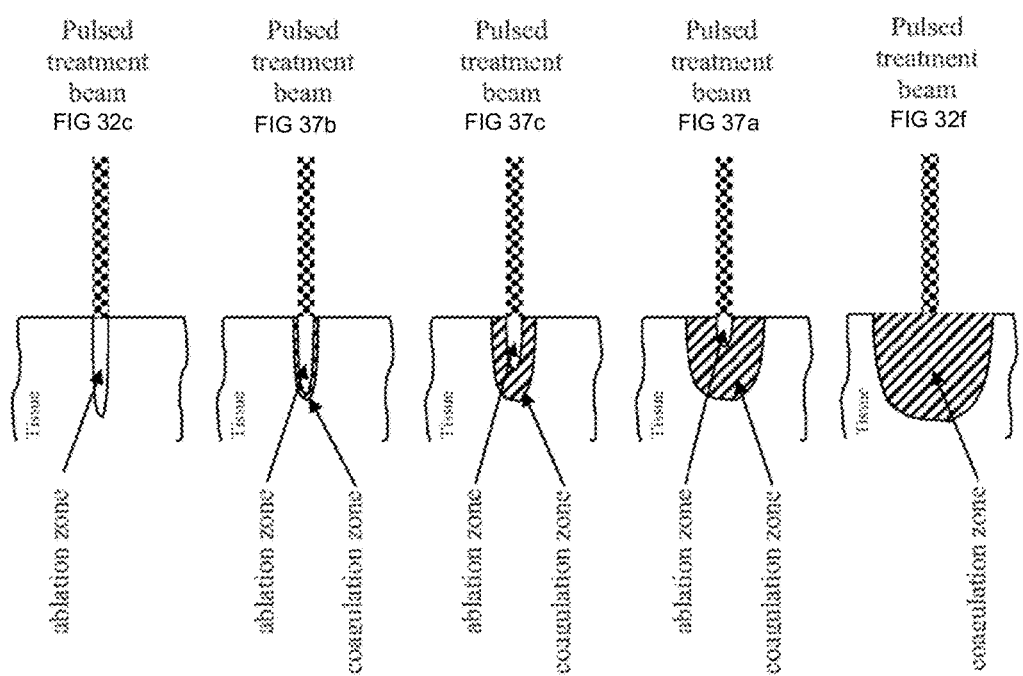
FIG. 47 shows representative tissue effects and their corresponding dynamic pulse schemes, in accordance with embodiments of the present invention.

FIG. 47 shows general representations of tissue effects caused by exemplary dynamic pulse configurations. The pulsed treatment beam as referenced in FIG. 32c shows the ablative removal of tissue with no appreciable thermal damage to the remaining tissue. The pulsed treatment beam as referenced in FIG. 37b shows primarily ablative removal of tissue with a small amount of thermal damage to the remaining tissue. The pulsed treatment beam as referenced in FIG. 37c shows ablative removal of tissue with a moderate amount of thermal damage to the remaining tissue. The pulsed treatment beam as referenced in FIG. 37a shows ablative removal of a small amount of tissue with a large amount of thermal damage to the remaining tissue. Finally the pulsed treatment beam as referenced in FIG. 32f shows a large area of coagulated tissue with no appreciable ablative removal of tissue.

Figure 48:
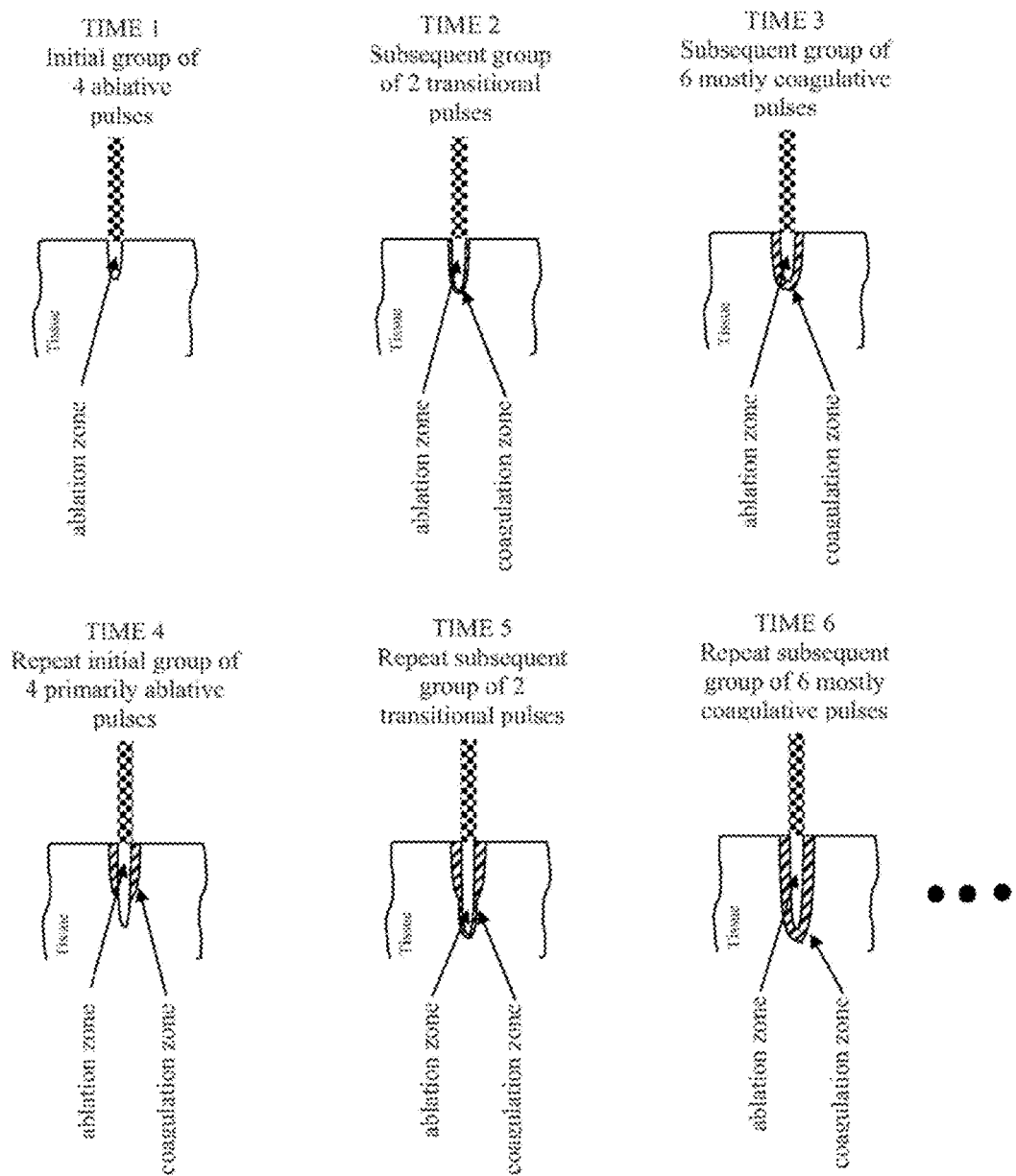
FIG. 48 Pulsed treatment time sequence of dynamic pulse scheme in FIG. 32D, showing the timing sequence of tissue effects for representative dynamic pulse schemes, in accordance with embodiments of the present invention.

FIG. 48 shows the timing sequence of tissue effects for the representative dynamic pulse scheme as shown in FIG. 32d. Time 1 represents the first 4 high amplitude, long period, short duration pulses effective at ablating tissue with no appreciable thermal damage to the remaining tissue. Time 2 represents the transitional pulses with consecutive reductions in amplitude and period and a lengthening of pulse duration. The transitional pulses continue to ablate, but with less efficiency and begin to deposit some heat in the remaining tissue. Time 3 represents the lower amplitude, shorter period, longer duration pulse series that primarily deposit heat in the tissue without appreciable ablation. Time 4 shows the ablative pulse series being repeated creating a deeper ablation zone. Time 5 shows the transitional pulse series being repeated modestly increasing the ablation zone depth and creating an additional thin coagulation zone. Time 6 shows the primarily thermal pulse series being repeated adding thermal damage to the remaining tissue. The periodic sequence may continue repeating throughout the duration of the exposure.

The diverse range of tissue interactions and surgical capabilities coupled with the portability and a self contained power source, such as a battery, make the system advantageous for field use. Surgical interventions can be performed in emergency, rescue and military field situations. Additionally the advantages of a Flash Vaporization system are well suited for robotic surgery.

It should be appreciated that the processor described above may comprise a processor system having one or more processors, and that the tangible medium of the processor may comprise a computer program configured to implement the methods of tissue treatment illustrated above, for example in accordance with the pulse sequences described above.

It should be appreciated that the specific steps illustrated in the flow diagrams above provide a particular methods of treating a patient, according to embodiments of the present invention. Other sequences of steps may also be performed according to alternative embodiments. For example, alternative embodiments of the present invention may perform the steps outlined above in a different order. Moreover, the individual steps illustrated in the figures may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

We claim:

1. A system for treating tissue, the system comprising:
a laser to generate a laser beam;
a controller which controls the laser in response to parameters including pulse length and pulse energy; and
a user interface connected to controller, said interface comprising a user selectable adjustment to select first and second modes;
wherein the controller adjusts the laser to operate successively in the first mode with a first set of adjustable parameters and the second mode with a second set of adjustable parameters, and wherein the controller causes dynamic transition between the first and second modes during an exposure; and
a beam delivery device coupled to the laser to deliver the laser beam to target tissue during the exposure;
wherein the controller controls both a q-switch and a pump source, and the first set of parameters includes a first set of q-switch parameters and a first set of pump pulse parameters which cause generation of one or more pulses each having both a pulse width between 1 ns and 500 ns and a fluence at the treatment site between 5 J/cm2 and 500 J/cm2 and the second set of parameters includes a second set of q-switch parameters and a second set of pump pulse parameters, wherein the q-switch is in the off mode, which cause generation of an average irradiance at a treatment site between 500 W/cm2 and 1 MW/cm2.

2. The system of claim 1, wherein a pulse period between each pulse of said first mode is between 200 us and 200 ms.

3. The system of claim 1, wherein the laser beam has a treatment spot size between 10 μm and 300 μm.

4. The system of claim 1, wherein the laser beam has a wavelength between 1.8 μm and 2.2 μm.

5. The system of claim 1, wherein the laser beam has a wavelength in a range of 1.92 to 2.01 μm.

6. The system of claim 1, wherein the laser has a gain medium comprising Tm doped host.

7. The system of claim 1, wherein the laser has a gain medium comprising Ho doped host.

8. The system of claim 1, wherein the laser gain medium is end pumped.

9. The system of claim 1, wherein the laser beam has an M2, which is less than 10.

10. The system of claim 1, wherein the system further comprises a silica core waveguide to deliver the laser energy to the treatment site.

11. The system of claim 10, wherein the waveguide core diameter is between 25 μm and 150 μm.

12. The system of claim 1, wherein the user selectable adjustment is presented on the user interface in terms of an adjustable depth of thermal damage.

13. The system of claim 12 wherein the adjustable depth of thermal damage represented on the user interface ranges between 0 μm and 2 mm.

14. The system of claim 1, wherein in one of the first and second modes the laser beam causes a depth of thermal damage in the target tissue during the exposure of less than 50 μm.

15. The system of claim 1, wherein, the dynamic pulse sequence comprises periodic repetition of a pulsing pattern that intermixes cutting pulses according to a first set of pulse parameters and coagulating pulses according to a second set of pulse parameters.

16. The system of claim 15, wherein the laser beam has a wavelength between 1.8 μm and 2.2 μm.

17. The system of claim 15, wherein the laser has a gain medium comprising Tm doped host.

18. A system for treating tissue, the system comprising:
a laser to generate a laser beam;
a controller which controls the laser in response to parameters including pulse length and pulse energy; and
a user interface connected to controller, said interface comprising a user selectable adjustment to select first and second modes;
wherein the controller adjusts the laser to operate successively in the first mode with a first set of adjustable parameters and the second mode with a second set of adjustable parameters, and wherein the controller causes dynamic transition between the first and second modes during an exposure; and
a beam delivery device coupled to the laser to deliver the laser beam to target tissue during the exposure;
wherein the controller controls both a q-switch and a pump source, and the first set of parameters includes a first set of q-switch parameters and a first set of pump pulse parameters generating one or more pulses each having both a pulse width between 1 ns and 500 ns and a fluence at a treatment site between 5 J/cm2 and 500 J/cm2, and the second set of parameters includes a second set of q-switch parameters and a second set of pump pulse parameters with one or more pulses each having both a pulse width of at least 1.2× greater than the pulse width of the first mode and a fluence at a treatment site of at least 0.8× less than the fluence at the treatment site of the first mode.

19. The system of claim 18, wherein, the dynamic pulse sequence comprises periodic repetition of a pulsing pattern that intermixes cutting pulses according to a first set of pulse parameters and coagulating pulses according to a second set of pulse parameters.

20. The system of claim 18, wherein the laser beam has a wavelength between 1.8 μm and 2.2 μm.

21. The system of claim 18, wherein the laser has a gain medium comprising Tm doped host.

\* \* \* \* \*